(12) United States Patent
Maier et al.

(10) Patent No.: US 7,569,574 B2
(45) Date of Patent: Aug. 4, 2009

(54) PURINE DERIVATIVES, THE PREPARATION THEREOF AND THEIR USE AS PHARMACEUTICAL COMPOSITIONS

(75) Inventors: Roland Maier, Biberach (DE); Frank Himmelsbach, Mittelbiberach (DE); Matthias Eckhardt, Biberach (DE); Elke Langkopf, Warthausen (DE); Michael Mark, Biberach (DE); Ralf R. H. Lotz, Schemmerhofen (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 50 days.

(21) Appl. No.: 10/634,047

(22) Filed: Aug. 4, 2003

(65) Prior Publication Data

US 2004/0122228 A1   Jun. 24, 2004

Related U.S. Application Data

(60) Provisional application No. 60/408,021, filed on Sep. 4, 2002.

(30) Foreign Application Priority Data

Aug. 22, 2002   (DE)   ................. 102 38 477

(51) Int. Cl.
*C07D 473/30* (2006.01)
*C07D 473/18* (2006.01)
*C07D 473/04* (2006.01)
*C07D 473/06* (2006.01)
*A61K 31/522* (2006.01)
*A61P 3/10* (2006.01)
*A61P 3/04* (2006.01)

(52) U.S. Cl. ............................ 514/263.22; 514/217.06; 514/218; 514/230.5; 514/248; 514/234.2; 514/263.2; 514/263.23; 514/263.24; 514/263.3; 514/263.37; 514/263.38; 514/252.16; 540/575; 540/600; 544/105; 544/118; 544/237; 544/271; 544/272; 544/276; 546/210

(58) Field of Classification Search ............ 514/217.06, 514/218, 230.5, 248, 234.2, 263.21, 263.22, 514/263.24, 263.3, 263.37, 263.38, 263.2, 514/263.23, 252.16; 544/105, 237, 276, 544/118, 271, 272; 540/575, 600

See application file for complete search history.

(56) References Cited

U.S. PATENT DOCUMENTS

| | | | |
|---|---|---|---|
| 2,928,833 | A | 3/1960 | Leake et al. |
| 4,005,208 | A | 1/1977 | Bender |
| 4,599,338 | A | 7/1986 | Regnier et al. |
| 5,041,448 | A | 8/1991 | Janssens et al. |
| 5,051,517 | A | 9/1991 | Findeisen |
| 5,223,499 | A | 6/1993 | Greenlee |
| 5,234,897 | A | 8/1993 | Findeisen et al. |
| 5,258,380 | A | * 11/1993 | Janssens et al. .......... 514/233.2 |
| 5,266,555 | A | 11/1993 | Findeisen et al. |
| 5,389,642 | A | 2/1995 | Dorsch |
| 5,470,579 | A | 11/1995 | Bonte et al. |
| 5,719,279 | A | 2/1998 | Kufner-Muhl et al. |
| 5,753,635 | A | 5/1998 | Buckman |
| 6,303,661 | B1 | 10/2001 | Demuth |
| 6,342,601 | B1 | 1/2002 | Bantick |
| 6,548,481 | B1 | 4/2003 | Demuth et al. |
| 6,579,868 | B1 | 6/2003 | Asano et al. |
| 6,784,195 | B2 | 8/2004 | Hale et al. |
| 6,821,978 | B2 | 11/2004 | Chackalamannil |
| 6,869,947 | B2 | 3/2005 | Kanstrup |
| 7,060,722 | B2 | 6/2006 | Kitajima |
| 7,074,794 | B2 | 7/2006 | Kitajima |
| 7,074,798 | B2 | 7/2006 | Yoshikawa |
| 7,074,923 | B2 | 7/2006 | Dahanukar |
| 7,109,192 | B2 | 9/2006 | Hauel |

(Continued)

FOREIGN PATENT DOCUMENTS

CA   2136288 A1   5/1995

(Continued)

OTHER PUBLICATIONS

Busso et al., American Journal of Pathology 166:433-442 (2005).*

(Continued)

*Primary Examiner*—Mark L Berch
(74) *Attorney, Agent, or Firm*—Michael P. Morris; David L. Kershner; Philip I. Datlow

(57) ABSTRACT

The invention relates to new purine derivatives of general formula

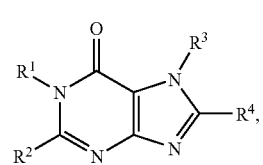

(I)

wherein $R^1$ to $R^4$ are defined as in the claims, the tautomers, the stereoisomers, the mixtures, the prodrugs thereof and the salts thereof, particularly the physiologically acceptable salts thereof with inorganic or organic acids or bases which have valuable pharmacological properties, particularly an inhibiting effect on the activity of the enzyme dipeptidylpeptidase-IV (DPP-IV), the preparation thereof, the use thereof for the prevention or treatment of diseases or conditions associated with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof as well as processes for the preparation thereof.

14 Claims, No Drawings

U.S. PATENT DOCUMENTS

| | | |
|---|---|---|
| 7,179,809 B2 | 2/2007 | Eckhardt |
| 7,183,280 B2 | 2/2007 | Himmelsbach |
| 7,192,952 B2 | 3/2007 | Kanstrup |
| 7,217,711 B2 | 5/2007 | Eckhardt |
| 7,235,538 B2 | 6/2007 | Kanstrup et al. |
| 2002/0161001 A1 | 10/2002 | Kanstrup |
| 2002/0169174 A1 | 11/2002 | Chackalamannil et al. |
| 2002/0198205 A1 | 12/2002 | Himmelsbach |
| 2003/0105077 A1 | 6/2003 | Kanstrup et al. |
| 2003/0199528 A1 | 10/2003 | Kanstrup |
| 2003/0232987 A1 | 12/2003 | Dahanukar et al. |
| 2003/0236272 A1 | 12/2003 | Carr |
| 2004/0034014 A1 | 2/2004 | Kanstrup et al. |
| 2004/0077645 A1 | 4/2004 | Himmelsbach et al. |
| 2004/0082570 A1 | 4/2004 | Yoshikawa |
| 2004/0087587 A1 | 5/2004 | Himmelsbach |
| 2004/0097510 A1 | 5/2004 | Himmelsbach et al. |
| 2004/0116328 A1* | 6/2004 | Yoshikawa et al. ............ 514/2 |
| 2004/0122228 A1 | 6/2004 | Maier |
| 2004/0138214 A1 | 7/2004 | Himmelsbach et al. |
| 2004/0138215 A1 | 7/2004 | Eckhardt |
| 2004/0166125 A1 | 8/2004 | Himmelsbach |
| 2005/0020574 A1 | 1/2005 | Hauel et al. |
| 2005/0026921 A1 | 2/2005 | Eckhardt |
| 2005/0130985 A1 | 6/2005 | Himmelsbach |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt |
| 2005/0234108 A1 | 10/2005 | Himmelsbach et al. |
| 2005/0261352 A1 | 11/2005 | Eckhardt |
| 2006/0004074 A1 | 1/2006 | Eckhardt |
| 2006/0058323 A1 | 3/2006 | Eckhardt et al. |
| 2006/0063787 A1 | 3/2006 | Yoshikawa |
| 2006/0079541 A1 | 4/2006 | Langkopf |
| 2006/0094722 A1* | 5/2006 | Yasuda et al. ............... 514/248 |
| 2006/0100199 A1 | 5/2006 | Yoshikawa et al. |
| 2006/0142310 A1 | 6/2006 | Pfrengle et al. |
| 2006/0173056 A1 | 8/2006 | Kitajima |
| 2006/0205711 A1 | 9/2006 | Himmelsbach |
| 2006/0247226 A1 | 11/2006 | Himmelsbach |
| 2007/0027168 A1 | 2/2007 | Pfrengle et al. |
| 2007/0088038 A1 | 4/2007 | Eckhardt |
| 2007/0093659 A1 | 4/2007 | Bonfanti |
| 2007/0142383 A1 | 6/2007 | Eckhardt |
| 2007/0219178 A1* | 9/2007 | Muramoto ............ 514/210.21 |
| 2007/0281940 A1 | 12/2007 | Dugi |

FOREIGN PATENT DOCUMENTS

| | | |
|---|---|---|
| CA | 2418656 A1 | 2/2002 |
| CA | 2496325 A1 | 3/2004 |
| CA | 2496249 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2590912 A1 | 6/2006 |
| DE | 10109021 A1 | 9/2002 |
| DE | 10117803 A1 | 10/2002 |
| EP | 0149578 A2 | 7/1985 |
| EP | 0400974 A2 | 5/1990 |
| EP | 0399285 A1 | 11/1990 |
| EP | 0412358 A1 | 2/1991 |
| EP | 0524482 A1 | 1/1993 |
| EP | 0657454 A1 | 6/1995 |
| EP | 1 054 012 A1 | 11/2000 |
| EP | 1338456 A2 | 8/2003 |
| EP | 1514552 A1 | 3/2005 |
| EP | 1537880 A1 | 8/2005 |
| ES | 385302 A1 | 4/1973 |
| FR | 2707641 A1 | 1/1995 |
| JP | S37-4895 | 6/1962 |
| JP | 2003/300977 | 10/2003 |
| JP | 2006/045156 | 2/2006 |
| WO | 91/07945 A1 | 6/1991 |
| WO | 94/03456 A1 | 2/1994 |
| WO | 99/29695 A1 | 6/1999 |
| WO | 02/02560 A2 | 1/2002 |
| WO | 02/14271 A1 | 2/2002 |
| WO | 02/24698 A1 | 3/2002 |
| WO | 02/068420 A1 | 9/2002 |
| WO | 03/004496 A1 | 1/2003 |
| WO | 03/024965 A2 | 3/2003 |
| WO | 03/057200 A2 | 7/2003 |
| WO | 03/104229 A1 | 12/2003 |
| WO | 2004/018467 A2 | 3/2004 |
| WO | 2004/018468 A2 | 3/2004 |
| WO | 2004/033455 A2 | 4/2004 |
| WO | WO 2004/096806 A1 | 4/2004 |
| WO | WO 2004028524 A1 * | 4/2004 |
| WO | 2004/041820 A1 | 5/2004 |
| WO | 2004/046148 A1 | 6/2004 |
| WO | 2004/048379 A1 | 6/2004 |
| WO | WO 2004096806 A1 * | 11/2004 |
| WO | 2004/108730 A1 | 12/2004 |
| WO | 2004/050658 A1 | 6/2005 |
| WO | 2005/058901 A1 | 6/2005 |
| WO | 2005/082906 A1 | 9/2005 |
| WO | 2005/085246 A1 | 9/2005 |
| WO | 2004/111051 A1 | 12/2005 |
| WO | 2006/029769 A1 | 3/2006 |
| WO | 2006/048427 A1 | 5/2006 |
| WO | 2006/068163 A1 | 6/2006 |
| WO | 2007/017423 A2 | 2/2007 |
| WO | WO 2008/017670 A1 | 2/2008 |

OTHER PUBLICATIONS

K. Augustyns, et al., "The Unique Properties of Dipeptidyl-peptidase IV (DPP IV / CD26) and the Therapeutic Potential of DPP IV Inhibitors", Curr. Med. Chem. 1999, vol. 6, pp. 311-327.

U.S. Appl. No. 11/744,700, filed May 5, 2007, Sieger.

U.S. Appl. No. 11/744,701, filed May 5, 2007, Kohlrausch.

Beljean-Leymarie et al., Hydrazines et hydrazones hétérocycliques. IV. Synthéses dérivés de l'hydrazine dans la série des imidazo[4,5-d]pyridazinones-4, Can. J. Chem., vol. 61, No. 11, 1983, pp. 2563-2566.

Bollag, R.J. et al; "Osteoblast-Derived Cells Express Functional Glucose-Dependent Insulinotropic Peptide Receptors," Endocrinology, vol. 141, No. 3, 2000, pp. 1228-1235.

Brittain, H.G., "Methods for the Characterization of Polymorphys: X-Ray Powder Diffraction," Polymorphism in Pharmaceutical Solids, 1999, p. 235-238.

Caira, M.R., "Crystalline polymorphism of organic compounds" Topics in Current Chemistry, Springer, Berlin, vol. 198, 1998, p. 163-208.

Conarello, S.L. et al; "Mice lacking dipetidyl peptidase IV are protected against obesity and insulin resistance," PNAS 2003; 100:6825-6830; originally published online May 14, 2003; information current as of Dec. 2006. www.pnas.org/cgi/content/full/100/11/6825.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

DeMeester, I. et al.; "CD26, let it cut or cut it down", Review: Immunology Today; Aug. 1999, vol. 20, No. 8 pp. 367-375.

Korom, S. et al; Inhibition of CD26/dipeptidyl peptidase IV activity in vivo prolongs cardiac allograft survival in rat recipients[1,2], Transplantation, May 27, 1997, vol. 63, No. 10, pp. 1495-1500.

Pospisilik, et al; Dipeptidyl Peptidase IV Inhibitor Treatment Stimulates β-Cell Survival and Islet Neogenesis in Streptozotocin-Induced Diabetic Rats; Diabetes, vol. 52, Mar. 2003 pp. 741-750.

Rhee et al.: "Nitrogen-15-Labeled Deoxynucleosides. 3. Synthesis of [3-$^{15}$N]-2'-Deoxyadenosine" J. Am. Chem. Soc. 1990, 112, 8174-8175.

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Tanaka, S.. et al; "Suppression of Arthritis by the Inhibitors of Dipeptidyl Peptidase IV," In. J. Immunopharmac., vol. 19, No. 1, pp. 15-24, 1997.

Wolff, M.E.: "Burger's Medicinal Chemistry and Drug Discovery" Fifth Edition, vol. 1: Principles and Practice, pp. 975-977, 1994, John Wiley & Sons, Inc.

Zhong, Qing et al; "Glucose-dependent insulinotropic peptide stimulates proliferation and TGF-β release from MG-63 cells," Peptides 24 (2003) 611-616.

Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Farmatsevtichnii Zhurnal, 1986, (Kiev), vol. 5, 1986, pp. 41-44.

Chemical Abstracts Accession No. 106:95577 Romanenko et al., "Synthesis and biological activity of 3-methyl, 7-or 8-alkyl-7,8-dialkyl, heterocyclic, and cyclohexylaminoxanthines," Zaporozh. Med. Institute (1986).

Yoshikawa, Seiji et al.: Chemical Abstract of Japanese Patent No. WO 2003/104229 Preparation of purinone derivatives as dipeptidylpeptidase IV (DPP-IV) inhibitors.

International Search Report for PCT/EP03/09127 mailed Nov. 28, 2003.

International Search Report for PCT/EP03/12821 mailed Mar. 30, 2004.

International Search Report for PCT/EP03/13648 mailed Apr. 5, 2004.

International Search Report for PCT/EP2007/054270 mailed Aug. 14, 2007.

International Search Report for PCT/EP2007/058181 mailed Nov. 28, 2007.

International Search Report for PCT/EP2007/054204 mailed Aug. 3, 2007.

International Search Report for PCT/EP2007/054201 mailed Aug. 29, 2007.

Januvia; Patient Information; Oct. 2007.

Patani George A. et al.: "Bioisoterism : A Rational Approach in Drug Design", Chemical Reviews, 1996, vol. 96, No. 8, pp. 3147-3176.

Zejc, Alfred et al; Badania Nad Piperazynowymi Pochodnymi Dwumetyloksantyn; Acta Polon. Pharm. XXXV. Nr 4, 1976, pp. 417-421.

Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.

* cited by examiner

ND THEIR USE AS
PURINE DERIVATIVES, THE PREPARATION THEREOF AND THEIR USE AS PHARMACEUTICAL COMPOSITIONS

RELATED APPLICATIONS

Benefit of U.S. Provisional Application Ser. No. 60/408,021, filed on Sep. 4, 2002 and German application DE 102 38 477 filed Aug. 22, 2002 is hereby claimed.

FIELD OF THE INVENTION

The present invention relates to substituted purines of general formula

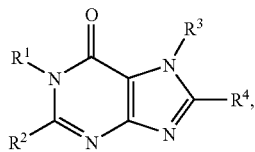

(I)

the tautomers, the stereoisomers, the mixtures, the prodrugs thereof and the salts thereof, particularly the physiologically acceptable salts thereof with inorganic or organic acids or bases which have valuable pharmacological properties, particularly an inhibiting effect on the activity of the enzyme dipeptidylpeptidase-IV (DPP-IV), the preparation thereof, the use thereof for the prevention or treatment of diseases or conditions associated with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof as well as processes for the preparation thereof.

In the above formula I $R^1$ denotes a hydrogen atom, a $C_{1-8}$-alkyl group, a $C_{3-8}$-alkenyl group, a $C_{3-4}$-alkenyl group which is substituted by a $C_{1-2}$-alkyloxy-carbonyl, aminocarbonyl, $C_{1-3}$-alkylamino-carbonyl, di-($C_{1-3}$-alkyl)-amino-carbonyl, pyrrolidin-1-ylcarbonyl, piperidin-1-ylcarbonyl or morpholin-4-ylcarbonyl group, a $C_{3-8}$-alkynyl group, a $C_{1-6}$-alkyl group substituted by a group $R_a$, where $R_a$ denotes a $C_{3-7}$-cycloalkyl, heteroaryl, cyano, carboxy, $C_{1-3}$-alkyloxy-carbonyl, aminocarbonyl, $C_{1-3}$-alkylamino-carbonyl, di-($C_{1-3}$-alkyl)-amino-carbonyl, pyrrolidin-1-ylcarbonyl, piperidin-1-ylcarbonyl, morpholin-4-ylcarbonyl, piperazin-1-ylcarbonyl, 4-methylpiperazin-1-ylcarbonyl or 4-ethylpiperazin-1-ylcarbonyl group, a $C_{1-6}$-alkyl group substituted by a phenyl group, where the phenyl ring is substituted by the groups $R^{10}$ to $R^{14}$ and $R^{10}$ denotes a hydrogen atom, a fluorine, chlorine, bromine or iodine atom, a $C_{1-4}$-alkyl, hydroxy or $C_{1-4}$-alkyloxy group, a nitro, amino, $C_{1-3}$-alkylamino, di-($C_{1-3}$-alkyl)-amino, cyan-$C_{1-3}$-alkylamino, N-(cyan-$C_{1-3}$-alkyl)-N—($C_{1-3}$-alkyl)-amino, $C_{1-3}$-alkyloxy-carbonyl-$C_{1-3}$-alkylamino, pyrrolidin-1-yl, piperidin-1-yl, morpholin-4-yl, piperazin-1-yl or 4-($C_{1-3}$-alkyl)-piperazin-1-yl group, a formylamino, $C_{1-3}$-alkyl-carbonylamino, $C_{3-6}$-cycloalkyl-carbonylamino, $C_{3-6}$-cycloalkyl-$C_{1-3}$-alkyl-carbonylamino, arylcarbonylamino, aryl-$C_{1-3}$-alkylcarbonyl-amino, $C_{1-3}$-alkyloxy-carbonylamino, aminocarbonylamino, $C_{1-3}$-alkyl-amino-carbonylamino, di-($C_{1-3}$-alkyl)-aminocarbonylamino, pyrrolidin-1-yl-carbonylamino, piperidin-1-yl-carbonylamino, morpholin-4-yl-carbonylamino, piperazin-1-yl-carbonylamino or 4-($C_{1-3}$-alkyl)-piperazin-1-yl-carbonylamino, $C_{1-3}$-alkyl-sulphonylamino, bis-($C_{1-3}$-alkylsulphonyl)-amino, aminosulphonylamino, $C_{1-3}$-alkyl-amino-sulphonylamino, di-($C_{1-3}$-alkyl)-aminosulphonylamino, pyrrolidin-1-yl-sulphonylamino, piperidin-1-yl-sulphonylamino, morpholin-4-yl-sulphonylamino, piperazin-1-yl-sulphonylamino or 4-($C_{1-3}$-alkyl)-piperazin-1-yl-sulphonylamino, ($C_{1-3}$-alkylamino)-thiocarbonylamino, ($C_{1-3}$-alkyloxy-carbonylamino)-carbonylamino, arylsulphonylamino or aryl-$C_{1-3}$-alkyl-sulphonylamino group, an N—($C_{1-3}$-alkyl)-formylamino, N—($C_{1-3}$-alkyl)-N—($C_{1-3}$-alkyl-carbonyl)-amino, N—($C_{1-3}$-alkyl)-N—($C_{3-6}$-cycloalkyl-carbonyl)-amino, N—($C_{1-3}$-alkyl)-N—($C_{3-6}$-cycloalkyl-$C_{1-3}$-alkyl-carbonyl)-amino, N—($C_{1-3}$-alkyl)-N-(arylcarbonyl)-amino, N—($C_{1-3}$-alkyl)-N-(aryl-$C_{1-3}$-alkyl-carbonyl)-amino, N—($C_{1-3}$-alkyl)-N—($C_{1-3}$-alkyloxy-carbonyl)-amino, N-(aminocarbonyl)-N—($C_{1-3}$-alkyl)-amino, N—($C_{1-3}$-alkyl-aminocarbonyl)-N—($C_{1-3}$-alkyl)-amino, N-[di-($C_{1-3}$-alkyl)aminocarbonyl]-N—($C_{1-3}$-alkyl)-amino, N—($C_{1-3}$-alkyl)-N—($C_{1-3}$-alkyl-sulphonyl)-amino, N—($C_{1-3}$-alkyl)-N-(arylsulphonyl)-amino or N—($C_{1-3}$-alkyl)-N-(aryl-$C_{1-3}$-alkyl-sulphonyl)-amino group, a 2-oxo-imidazolidin-1-yl, 2,4-dioxo-imidazolidin-1-yl, 2,5-dioxo-imidazolidin-1-yl or 2-oxo-hexahydropyrimidin-1-yl group wherein the nitrogen atom in the 3 position may be substituted in each case by a methyl or ethyl group, a cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl or 4-($C_{1-3}$-alkyl)-piperazin-1-yl-carbonyl group, a $C_{1-3}$-alkyl-carbonyl or an arylcarbonyl group, a carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl or 4-($C_{1-3}$-alkyl)-piperazin-1-yl-carbonyl-$C_{1-3}$-alkyl group, a carboxy-$C_{1-3}$-alkyloxy, $C_{1-3}$-alkyloxy-carbonyl-$C_{1-3}$-alkyloxy, cyano-$C_{1-13}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyloxy, piperazin-1-yl-carbonyl-$C_{1-3}$-alkyloxy or 4-($C_{1-3}$-alkyl)-piperazin-1-yl-carbonyl-$C_{1-3}$-alkyloxy group, a hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, piperidin-1-yl-$C_{1-3}$-alkyl, morpholin-4-yl-$C_{1-3}$-alkyl, piperazin-1-yl-$C_{1-3}$-alkyl, 4-($C_{1-3}$-alkyl)-piperazin-1-yl-$C_{1-3}$-alkyl group, a hydroxy-$C_{1-3}$-alkyloxy, $C_{1-3}$-alkyloxy-$C_{1-3}$-alkyloxy, $C_{1-3}$-alkylsulphanyl-$C_{1-3}$-alkyloxy, $C_{1-3}$-alkylsulphinyl-$C_{1-3}$-alkyloxy, $C_{1-3}$-alkylsulphonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, piperidin-1-yl-$C_{1-3}$-alkyloxy, morpholin-4-yl-$C_{1-3}$-alkyloxy, piperazin-1-yl-$C_{1-3}$-alkyloxy, 4-($C_{1-3}$-alkyl)-piperazin-1-yl-$C_{1-3}$-alkyloxy group, a mercapto, $C_{1-3}$-alkylsulphanyl, $C_{1-3}$-alkysulphinyl, $C_{1-3}$-alkylsulphonyl, $C_{1-3}$-alkylsulphonyloxy, arylsulphonyloxy, trifluoromethylsulphanyl, trifluoromethylsulphinyl or trifluoromethylsulphonyl group, a sulpho, aminosulphonyl, $C_{1-3}$-alkyl-aminosulphonyl, di-($C_{1-3}$-alkyl)-amino-sulphonyl, pyrrolidin-1-yl-sulphonyl, piperidin-1-yl-sulphonyl, morpholin-4-yl-sulphonyl, piperazin-1-yl-sulphonyl or 4-($C_{1-3}$-alkyl)-piperazin-1-yl-sulphonyl group, a methyl or methoxy group substituted by 1 to 3 fluorine atoms, an ethyl or ethyloxy group substituted by 1 to 5 fluorine atoms, a $C_{2-4}$-alkenyl or $C_{2-4}$-alkynyl group, a $C_{3-4}$-alkenyloxy or $C_{3-4}$-alkynyloxy group, a $C_{3-6}$-cycloalkyl or $C_{3-6}$-cycloalkyloxy group, a $C_{3-6}$-cycloalkyl-$C_{1-3}$-alkyl or $C_{3-6}$-cycloalkyl-$C_{1-3}$-alkyloxy group or an aryl, aryloxy, aryl-$C_{1-3}$-alkyl or aryl-$C_{1-3}$-alkyloxy group, $R^{11}$ and $R^{12}$, which may be identical or different, in each case represent a hydrogen atom, a fluorine, chlorine, bromine or iodine atom, a $C_{1-3}$-alkyl, trifluoromethyl, hydroxy, $C_{1-3}$-alkyloxy or cyano group, or $R^{11}$ together with $R^{12}$, if they are bound to adjacent carbon atoms, also represent a methylenedioxy, difluoromethylenedioxy or a straight-chain $C_{3-5}$-alkylene group and $R^{13}$ and $R^{14}$, which may be identical or different, in each case represent a hydrogen atom, a fluorine, chlorine or bromine atom, a trifluoromethyl, $C_{1-3}$-alkyl or $C_{1-3}$-alkyloxy group, a phenyl-$C_{1-4}$-alkyl group wherein the alkyl moiety is substituted by a cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl-group and the phenyl moiety is substituted by the groups $R^{10}$ to $R^{14}$, while $R^{10}$ to $R^{14}$ are as hereinbefore defined, a phenyl group substituted by the groups $R^{10}$ to $R^{14}$, where $R^{10}$ to $R^{14}$ are as hereinbefore defined, a phenyl-$C_{2-3}$-alkenyl group wherein the phenyl moiety is substituted by the groups $R^{10}$ to $R^{14}$, where $R^{10}$ to $R^{14}$ are as hereinbefore defined, a phenyl-$(CH_2)_m$-A-$(CH_2)_n$— group wherein the phenyl moiety is substituted by $R^{10}$ to $R^{14}$, where $R^{10}$ to $R^{14}$ are as hereinbefore defined and A represents a carbonyl group, m represents the number 0, 1 or 2 and n represents the number 1, 2 or 3, a phenylcarbonylmethyl group wherein the phenyl moiety is substituted by $R^{10}$ to $R^{14}$, where $R^{10}$ to $R^{14}$ are as hereinbefore defined and the methyl moiety is substituted by a $C_{1-3}$-alkyl group, a phenyl-$(CH_2)_m$—B—$(CH_2)_n$— group wherein the phenyl moiety is substituted by $R^{10}$ to $R^{14}$, where $R^{10}$ to $R^{14}$, m and n are as hereinbefore defined and B denotes a methylene group which is substituted by a hydroxy, $C_{1-3}$-alkyloxy, amino, $C_{1-3}$-alkylamino, di-($C_{1-3}$-alkyl)-amino, mercapto, $C_{1-3}$-alkylsulphanyl, $C_{1-3}$-alkylsulphinyl or $C_{1-3}$-alkylsulphonyl group and is optionally additionally substituted by a methyl or ethyl group, a naphthyl-$C_{1-3}$-alkyl group wherein the naphthyl moiety is substituted by the groups $R^{10}$ to $R^{14}$, where $R^{10}$ to $R^{14}$ are as hereinbefore defined, a naphthyl-$(CH_2)_m$-A-$(CH_2)_n$— group wherein the naphthyl moiety is substituted by $R^{10}$ to $R^{14}$, where $R^{10}$ to $R^{14}$, A, m and n are as hereinbefore defined, a naphthyl-$(CH_2)_m$—B—$(CH_2)_n$— group wherein the naphthyl moiety is substituted by $R^{10}$ to $R^{14}$, where $R^{10}$ to $R^{14}$, B, m and n are as hereinbefore defined, a [1,4]naphthoquinon-2-yl, chromen-4-on-3-yl, 1-oxoindan-2-yl, 1,3-dioxoindan-2-yl or 2,3-dihydro-3-oxo-benzofuran-2-yl group, a heteroaryl-$(CH_2)_m$-A-$(CH_2)_n$ group where A, m and n are as hereinbefore defined, a heteroaryl-$(CH_2)_m$—B—$(CH_2)_n$ group where B, m and n are as hereinbefore defined, a $C_{1-6}$-alkyl-A-$(CH_2)_n$ group where A and n are as hereinbefore defined, a $C_{3-7}$-cycloalkyl-$(CH_2)_m$-A-$(CH_2)_n$ group where A, m and n are as hereinbefore defined, a $C_{3-7}$-cycloalkyl-$(CH_2)_m$—B—$(CH_2)_n$ group where B, m and n are as hereinbefore defined, an $R^{21}$-A-$(CH_2)_n$— group wherein $R^{21}$ denotes a $C_{1-3}$-alkyloxycarbonyl, aminocarbonyl, $C_{1-3}$-alkylaminocarbonyl, di-($C_{1-3}$-alkyl)aminocarbonyl, pyrrolidin-1-yl-carbonyl, piperidin-1-yl-carbonyl or morpholin-4-yl-carbonyl, piperazin-1-yl-carbonyl, 4-methylpiperazin-1-yl-carbonyl or 4-ethylpiperazin-1-yl-carbonyl group and A and n are as hereinbefore defined, a phenyl-$(CH_2)_m$-D-$C_{1-3}$-alkyl group wherein the phenyl moiety is substituted by the groups $R^{10}$ to $R^{14}$, where $R^{10}$ to $R^{14}$ and m are as mentioned hereinbefore and D denotes an oxygen or sulphur atom, an imino, $C_{1-3}$-alkylimino, sulphinyl or sulphonyl group, a naphthyl-$(CH_2)_m$-D-$C_{1-3}$-alkyl group wherein the naphthyl moiety is substituted by the groups $R^{10}$ to $R^{14}$, where $R^{10}$ to $R^{14}$, D and m are as mentioned hereinbefore, a $C_{2-6}$-alkyl group substituted by a group $R_b$, where $R_b$ is isolated from the cyclic nitrogen atom in the 1 position of the purine skeleton by at least two carbon atoms and $R_b$ denotes a hydroxy, $C_{1-3}$-alkyloxy, mercapto, $C_{1-3}$-alkylsulphanyl, $C_{1-3}$-alkylsulphinyl, $C_{1-3}$-alkylsulphonyl, amino, $C_{1-3}$-alkyl-carbonylamino, $C_{3-6}$-cycloalkyl-carbonyl-amino, arylcarbonylamino, $C_{1-3}$-alkylamino, di-($C_{1-3}$-alkyl)-amino, pyrrolidin-1-yl, piperidin-1-yl, morpholin-4-yl, piperazin-1-yl or 4-($C_{1-3}$-alkyl)-piperazin-1-yl group, a $C_{3-6}$-cycloalkyl group, or an amino or arylcarbonylamino group, $R^2$ denotes a hydrogen atom, a $C_{1-8}$-alkyl group, a $C_{3-8}$-alkenyl group, a $C_{3-4}$-alkenyl group which is substituted by a $C_{1-2}$-alkyloxy-carbonyl, aminocarbonyl, $C_{1-3}$-alkylamino-carbonyl, di-($C_{1-3}$-alkyl)-amino-carbonyl, pyrrolidin-1-ylcarbonyl, piperidin-1-ylcarbonyl or morpholin-4-ylcarbonyl group, a $C_{3-8}$-alkynyl group, a $C_{3-6}$-cycloalkyl group, a $C_{1-6}$-alkyl group substituted by a group $R_a$, where $R_a$ is as hereinbefore defined, a phenyl group which is substituted by $R^{10}$ to $R^{14}$, where $R^{10}$ to $R^{14}$ are as hereinbefore defined, a $C_{1-6}$-alkyl group substituted by a phenyl group, wherein the phenyl ring is substituted by the groups $R^{10}$ to $R^{14}$ and $R^{10}$ to $R^{14}$ are as hereinbefore defined, a phenyl-$C_{1-4}$-alkyl group wherein the alkyl moiety is substituted by a cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl group and the phenyl moiety is substituted by the groups $R^{10}$ to $R^{14}$, where $R^{10}$ to $R^{14}$ are as hereinbefore defined, a phenyl-$C_{2-3}$-alkenyl group wherein the phenyl moiety is substituted by $R^{10}$ to $R^{14}$, where $R^{10}$ to $R^{14}$ are as hereinbefore defined, a heteroaryl group, a phenyl-$(CH_2)_m$-A or phenyl-$(CH_2)_m$-A-$(CH_2)_n$ group wherein the phenyl moiety is substituted in each case by $R^{10}$ to $R^{14}$, while A, $R^{10}$ to $R^{14}$, m and n are as hereinbefore defined, a phenylcarbonylmethyl group wherein the phenyl moiety is substituted by $R^{10}$ to $R^{14}$, where $R^{10}$ to $R^{14}$ are as hereinbefore defined and the methyl moiety is substituted by a $C_{1-3}$-alkyl group, a phenyl-$(CH_2)_m$—B or phenyl-$(CH_2)_m$—B—$(CH_2)_n$ group wherein the phenyl moiety is substituted in each case by $R^{10}$ to $R^{14}$, while B, $R^{10}$ to $R^{14}$, m and n are as hereinbefore defined, a naphthyl-$C_{1-3}$-alkyl group wherein the naphthyl moiety is substituted by the groups $R^{10}$ to $R^{14}$, where $R^{10}$ to $R^{14}$ are as hereinbefore defined, a naphthyl-$(CH_2)_m$-A or naphthyl-$(CH_2)_m$-A-$(CH_2)_n$ group wherein the naphthyl moiety is substituted in each case by $R^{10}$ to $R^{14}$, where $R^{10}$ to $R^{14}$, A, m and n are as hereinbefore defined, a naphthyl-$(CH_2)_m$—B or naphthyl-$(CH_2)_m$—B—$(CH_2)_n$ group wherein the naphthyl moiety is substituted in each case by $R^{10}$ to $R^{14}$, where $R^{10}$ to $R^{14}$, B, m and n are as hereinbefore defined, a heteroaryl-$(CH_2)_m$-A or heteroaryl-$(CH_2)_m$-A-$(CH_2)_n$ group where A, m and n are as hereinbefore defined, a heteroaryl-$(CH_2)_m$—B or heteroaryl-$(CH_2)_m$—B—$(CH_2)_n$ group where B, m and n are as hereinbefore defined, a $C_{1-6}$-alkyl-A or $C_{1-6}$-alkyl-A—$(CH_2)_n$ group where A and n are as hereinbefore defined, a $C_{3-7}$-cycloalkyl-$(CH_2)_m$-A or $C_{3-7}$-cycloalkyl-$(CH_2)_m$-A-$(CH_2)_n$ group where A, m and n are as hereinbefore defined, a $C_{3-7}$-cycloalkyl-$(CH_2)_m$—B or $C_{3-7}$-cycloalkyl-$(CH_2)_m$—B—$(CH_2)_n$ group where B, m and n are as hereinbefore defined, an $R^{21}$-A-$(CH_2)_n$ group wherein $R^{21}$, A and n are as hereinbefore defined, a phenyl-$(CH_2)_m$-D-$C_{1-3}$-alkyl group wherein the phenyl moiety is substituted by the groups $R^{10}$ to $R^{14}$, where $R^{10}$ to $R^{14}$, D and m are as mentioned hereinbefore, a naphthyl-$(CH_2)_m$-D-$C_{1-3}$-alkyl group wherein the naphthyl moiety is substituted by the groups $R^{10}$ to $R^{14}$, where $R^{10}$ to $R^{14}$, D and m are as mentioned hereinbefore, a $C_{1-6}$-alkyl group substituted by a group $R_b$, where $R_b$ is as hereinbefore defined, a cyano, carboxy, $C_{1-3}$-alkyloxy-carbonyl, aminocarbonyl, $C_{1-3}$-alkylamino-carbonyl, di-($C_{1-3}$-alkyl)-amino-carbonyl, pyrrolidin-1-ylcarbonyl, piperidin-1-ylcarbonyl, morpholin-4-ylcarbonyl, piperazin-1-ylcarbonyl, 4-methylpiperazin-1-ylcarbonyl or 4-ethylpiperazin-1-ylcarbonyl group, an amino, $C_{1-6}$-alkylamino or di-($C_{1-6}$-alkyl)-amino group, an amino group substituted by the groups $R^{15}$ and $R^{16}$ wherein $R^{15}$ denotes a hydrogen atom or a $C_{1-6}$-alkyl group and $R^{16}$ denotes a $C_{1-6}$-alkyl group which is substituted by $R_a$, where $R_a$ is as hereinbefore defined, an amino group substituted by the groups $R^{15}$ and $R^{17}$ wherein $R^{15}$ is as hereinbefore defined and $R^{17}$ denotes a $C_{2-6}$-alkyl group which is substituted by a hydroxy, $C_{1-3}$-alkyloxy, aryloxy, mercapto, $C_{1-3}$-alkylsulphanyl, $C_{1-3}$-alkylsulphinyl, $C_{1-3}$-alkylsulphonyl, $C_{1-3}$-alkylsulphonylamino, arylsulphanyl, arylsulphinyl, arylsulphonyl, arylsulphonylamino, $C_{1-3}$-alkyl-carbonylamino, $C_{3-6}$-cycloalkyl-carbonylamino, arylcarbonylamino, $C_{1-3}$-alkyl-oxycarbonylamino, aminocarbonylamino, $C_{1-3}$-alkyl-aminocarbonylamino, di-($C_{1-3}$-alkyl)-aminocarbonylamino, amino, $C_{1-3}$-alkylamino, di-($C_{1-3}$-alkyl)-amino, pyrrolidin-1-yl, piperidin-1-yl, morpholin-4-yl, piperazin-1-yl or 4-($C_{1-3}$-alkyl)-piperazin-1-yl group, a $C_{3-6}$-cycloalkylamino or N—($C_{3-6}$-cycloalkyl)-N—($C_{1-3}$-alkyl)-amino group, a phenylamino or N-(phenyl)-N—($C_{1-3}$-alkyl)-amino group wherein the phenyl moiety is substituted in each case by $R^{10}$ to $R^{14}$, where $R^{10}$ to $R^{14}$ are as hereinbefore defined, a phenyl-$C_{1-6}$-alkylamino or N-(phenyl-$C_{1-6}$-alkyl)-N—($C_{1-3}$-alkyl)-amino group wherein the phenyl moiety is substituted in each case by $R^{10}$ to $R^{14}$, where $R^{10}$ to $R^{14}$ are as hereinbefore defined, a naphthylamino or N-(naphthyl)-N—($C_{1-3}$-alkyl)-amino group, a naphthyl-$C_{1-6}$-alkylamino or N-(naphthyl-$C_{1-6}$-alkyl)-N—($C_{1-3}$-alkyl)-amino group, a heteroarylamino or N-(heteroaryl)-N—($C_{1-3}$-alkyl)-amino group, a pyrrolidin-1-yl, piperidin-1-yl, homopiperidin-1-yl, morpholin-4-yl, homomorpholin-4-yl, piperazin-1-yl, 4-($C_{1-3}$-alkyl)-piperazin-1-yl, homopiperazin-1-yl or 4-($C_{1-3}$-alkyl)-homopiperazin-1-yl group, or a $C_{1-6}$-alkyloxy, $C_{3-6}$-cycloalkyloxy or $C_{3-6}$-cycloalkyl-$C_{1-6}$-alkyloxy group, a $C_{1-6}$-alkylsulphanyl, $C_{3-6}$-cycloalkylsulphanyl or $C_{3-6}$-cycloalkyl-$C_{1-6}$-alkylsulphanyl group, a phenyloxy or phenylsulphanyl group wherein the phenyl moiety is substituted in each case by $R^{10}$ to $R^{14}$, where $R^{10}$ to $R^{14}$ are as hereinbefore defined, a phenyl-$C_{1-16}$-alkyloxy or phenyl-$C_{1-16}$-alkylsulphanyl group wherein the phenyl moiety is substituted in each case by $R^{10}$ to $R^{14}$, where $R^{10}$ to $R^{14}$ are as hereinbefore defined, a naphthyloxy or a naphthylsulphanyl group wherein the naphthyl moiety is substituted in each case by $R^{10}$ to $R^{14}$, where $R^{10}$ to $R^{14}$ are as hereinbefore defined, a naphthyl-$C_{1-6}$-alkyloxy or naphthyl-$C_{1-6}$-alkylsulphanyl group wherein the naphthyl moiety is substituted in each case by $R^{10}$ to $R^{14}$, where $R^{10}$ to $R^{14}$ are as hereinbefore defined, a heteroaryloxy or heteroarylsulphanyl group or a heteroaryl-$C_{1-6}$-alkyloxy or heteroaryl-$C_{1-6}$-alkylsulphanyl group, $R^3$ denotes a $C_{1-8}$-alkyl group, a $C_{1-14}$-alkyl group substituted by the group $R_c$, where $R_c$ denotes a $C_{3-7}$-cycloalkyl group optionally substituted by one or two $C_{1-3}$-alkyl groups, a $C_{5-7}$-cycloalkenyl group optionally substituted by one or two $C_{1-3}$-alkyl groups, an aryl group or a furanyl, thienyl, oxazolyl, isoxazolyl, thiazolyl, isothiazolyl, pyridyl, pyridazinyl, pyrimidyl or pyrazinyl group, while the above-mentioned heterocyclic groups may each be substituted by one or two $C_{1-3}$-alkyl groups or by a fluorine, chlorine, bromine or iodine atom or by a trifluoromethyl, cyano or $C_{1-3}$-alkyloxy group, a $C_{3-8}$-alkenyl group, a C$_{3-6}$-alkenyl group substituted by a fluorine, chlorine or bromine atom or a trifluoromethyl group, a C$_{3-8}$-alkynyl group, an aryl group or an aryl-C$_{2-4}$-alkenyl group, and R$^4$ denotes an azetidin-1-yl or pyrrolidin-1-yl group which is substituted in the 3 position by an amino, C$_{1-3}$-alkylamino or di-(C$_{1-3}$-alkyl)-amino group and may additionally be substituted by one or two C$_{1-3}$-alkyl groups, a piperidin-1-yl or hexahydroazepin-1-yl group which is substituted in the 3 position or in the 4 position by an amino, C$_{1-3}$-alkylamino or di-(C$_{1-3}$-alkyl)amino group and may additionally be substituted by one or two C$_{1-3}$-alkyl groups, a 3-amino-piperidin-1-yl group wherein the piperidin-1-yl-moiety is additionally substituted by an aminocarbonyl, C$_{1-2}$-alkyl-aminocarbonyl, di-(C$_{1-2}$-alkyl)-aminocarbonyl, pyrrolidin-1-yl-carbonyl, (2-cyano-pyrrolidin-1-yl-)carbonyl, thiazolidin-3-yl-carbonyl, (4-cyano-thiazolidin-3-yl) carbonyl, piperidin-1-ylcarbonyl or morpholin-4-ylcarbonyl group, a 3-amino-piperidin-1-yl group wherein the piperidin-1-yl moiety is additionally substituted in the 4 position or 5 position by a hydroxy or methoxy group, a 3-amino-piperidin-1-yl group wherein the methylene group is replaced in the 2 position or 6 position by a carbonyl group, a piperidin-1-yl or hexahydroazepin-1-yl-group substituted in the 3 position by an amino, C$_{1-3}$-alkylamino or di-(C$_{1-3}$-alkyl)-amino group, wherein two hydrogen atoms on the carbon skeleton of the piperidin-1-yl or hexahydroazepin-1-yl group are each replaced by a straight-chain alkylene bridge, this bridge containing 2 to 5 carbon atoms if the two hydrogen atoms are on the same carbon atom, or 1 to 4 carbon atoms if the hydrogen atoms are on adjacent carbon atoms, or 1 to 4 carbon atoms if the hydrogen atoms are on carbon atoms which are separated by one atom, or 1 to 3 carbon atoms if the hydrogen atoms are on carbon atoms which are separated by two atoms, an azetidin-1-yl, pyrrolidin-1-yl, piperidin-1-yl or hexahydroazepin-1-yl group which is substituted by an amino-C$_{1-3}$-alkyl, C$_{1-3}$-alkylamino-C$_{1-3}$-alkyl or a di-(C$_{1-3}$-alkyl)amino-C$_{1-3}$-alkyl group, a piperazin-1-yl or [1,4]diazepan-1-yl group optionally substituted on the carbon skeleton by one or two C$_{1-3}$-alkyl groups, a 3-imino-piperazin-1-yl, 3-imino-[1,4]diazepan-1-yl or 5-imino-[1,4]diazepan-1-yl group optionally substituted on the carbon skeleton by one or two C$_{1-3}$-alkyl groups, a [1,4]diazepan-1-yl group optionally substituted by one or two C$_{1-3}$-alkyl groups, which is substituted in the 6 position by an amino group, a C$_{3-7}$-cycloalkyl group which is substituted by an amino, C$_{1-3}$-alkylamino or di-(C$_{1-3}$-alkyl)-amino group, a C$_{3-7}$-cycloalkyl group which is substituted by an amino-C$_{1-3}$-alkyl, C$_{1-3}$-alkylamino-C$_{1-3}$-alkyl or a di-(C$_{1-3}$-alkyl) amino-C$_{1-3}$-alkyl group, a C$_{3-7}$-cycloalkyl-C$_{1-2}$-alkyl group wherein the cycloalkyl moiety is substituted by an amino, C$_{1-3}$-alkylamino or di-(C$_{1-3}$-alkyl)-amino group, a C$_{3-7}$-cycloalkyl-C$_{1-2}$-alkyl group wherein the cycloalkyl moiety is substituted by an amino-C$_{1-3}$-alkyl, C$_{1-3}$-alkylamino-C$_{1-3}$-alkyl or a di-(C$_{1-3}$-alkyl)amino-C$_{1-3}$-alkyl group, a C$_{3-7}$-cycloalkylamino group wherein the cycloalkyl moiety is substituted by an amino, C$_{1-3}$-alkylamino or di-(C$_{1-3}$-alkyl)-amino group, while the two nitrogen atoms on the cycloalkyl moiety are separated from one another by at least two carbon atoms, an N—(C$_{3-7}$-cycloalkyl)-N—(C$_{1-3}$-alkyl)-amino group wherein the cycloalkyl moiety is substituted by an amino, C$_{1-3}$-alkylamino or di-(C$_{1-3}$-alkyl)-amino group, while the two nitrogen atoms on the cycloalkyl moiety are separated from one another by at least two carbon atoms, a C$_{3-7}$-cycloalkylamino group wherein the cycloalkyl moiety is substituted by an amino-C$_{1-3}$-alkyl, C$_{1-3}$-alkylamino-C$_{1-3}$-alkyl or a di-(C$_{1-3}$-alkyl)amino-C$_{1-3}$-alkyl group, an N—(C$_{3-7}$-cycloalkyl)-N—(C$_{1-3}$-alkyl)-amino group wherein the cycloalkyl moiety is substituted by an amino-C$_{1-3}$-alkyl, C$_{1-3}$-alkylamino-C$_{1-3}$-alkyl or a di-(C$_{1-3}$-alkyl) amino-C$_{1-3}$-alkyl group, a C$_{3-7}$-cycloalkyl-C$_{1-2}$-alkyl-amino group wherein the cycloalkyl moiety is substituted by an amino, C$_{1-3}$-alkylamino or di-(C$_{1-3}$-alkyl)-amino group, an N—(C$_{3-7}$-cycloalkyl-C$_{1-2}$-alkyl)-N—(C$_{1-2}$-alkyl)-amino group wherein the cycloalkyl moiety is substituted by an amino, C$_{1-3}$-alkylamino or di-(C$_{1-3}$-alkyl)-amino group, a C$_{3-7}$-cycloalkyl-C$_{1-2}$-alkyl-amino group wherein the cycloalkyl moiety is substituted by an amino-C$_{1-3}$-alkyl, C$_{1-3}$-alkylamino-C$_{1-3}$-alkyl or a di-(C$_{1-3}$-alkyl)amino-C$_{1-3}$-alkyl group, an N—(C$_{3-7}$-cycloalkyl-C$_{1-2}$-alkyl)-N—(C$_{1-2}$-alkyl)-amino group wherein the cycloalkyl moiety is substituted by an amino-C$_{1-3}$-alkyl, C$_{1-3}$-alkylamino-C$_{1-3}$-alkyl or a di-(C$_{1-3}$-alkyl)amino-C$_{1-3}$-alkyl group, an R$^{19}$-C$_{2-4}$-alkylamino group wherein R$^{19}$ is separated from the nitrogen atom of the C$_{2-4}$-alkylamino moiety by at least two carbon atoms and R$^{19}$ denotes an amino, C$_{1-3}$-alkylamino or di-(C$_{1-3}$-alkyl)-amino group, an R$^{19}$-C$_{2-4}$-alkylamino group wherein the nitrogen atom of the C$_{2-4}$-alkylamino moiety is substituted by a C$_{1-3}$-alkyl group and R$^{19}$ is separated from the nitrogen atom of the C$_{2-4}$-alkylamino moiety by at least two carbon atoms, where R$^{19}$ is as hereinbefore defined, an amino group substituted by the group R$^{20}$ wherein R$^{20}$ denotes an azetidin-3-yl, azetidin-2-ylmethyl, azetidin-3-ylmethyl, pyrrolidin-3-yl, pyrrolidin-2-ylmethyl, pyrrolidin-3-ylmethyl, piperidin-3-yl, piperidin-4-yl, piperidin-2-ylmethyl, piperidin-3-ylmethyl or piperidin-4-ylmethyl group, while the groups mentioned for R$^{20}$ may each be substituted by one or two C$_{1-3}$-alkyl groups, an amino group substituted by the group R$^{20}$ and a C$_{1-3}$-alkyl group wherein R$^{20}$ is as hereinbefore defined, while the groups mentioned for R$^{20}$ may each be substituted by one or two C$_{1-3}$-alkyl groups, an R$^{19}$—C$_{3-4}$-alkyl group wherein the C$_{3-4}$-alkyl moiety is straight-chained and may additionally be substituted by one or two C$_{1-3}$-alkyl groups, where R$^{19}$ is as hereinbefore defined, a 3-amino-2-oxo-piperidin-5-yl or 3-amino-2-oxo-1-methyl-piperidin-5-yl group, a pyrrolidin-3-yl, piperidin-3-yl, piperidin-4-yl, hexahydroazepin-3-yl or hexahydroazepin-4-yl group which is substituted in the 1 position by an amino, C$_{1-3}$-alkylamino or di-(C$_{1-3}$-alkyl)amino group, or an azetidin-2-yl-C$_{1-2}$-alkyl, azetidin-3-yl-C$_{1-2}$-alkyl, pyrrolidin-2-yl-C$_{1-2}$-alkyl, pyrrolidin-3-yl, pyrrolidin-3-yl-C$_{1-2}$-alkyl, piperidin-2-yl-C$_{1-2}$-alkyl, piperidin-3-yl, piperidin-3-yl-C$_{1-2}$-alkyl, piperidin-4-yl or piperidin-4-yl-C$_{1-2}$-alkyl group, while the above-mentioned groups may each be substituted by one or two C$_{1-3}$-alkyl groups, while by the aryl groups mentioned in the definition of the above groups are meant phenyl or naphthyl groups, which may be mono- or disubstituted by $R_h$ independently of one another, where the substituents are identical or different and $R_h$ denotes a fluorine, chlorine, bromine or iodine atom, a trifluoromethyl, cyano, nitro, amino, aminocarbonyl, aminosulphonyl, methylsulphonyl, acetylamino, methylsulphonylamino, $C_{1-3}$-alkyl, cyclopropyl, ethenyl, ethynyl, hydroxy, $C_{1-3}$-alkyloxy, difluoromethoxy or trifluoromethoxy group, by the heteroaryl groups mentioned in the definitions of the above-mentioned groups are meant a pyrrolyl, furanyl, thienyl, pyridyl, indolyl, benzofuranyl, benzothiophenyl, quinolinyl or isoquinolinyl group, or a pyrrolyl, furanyl, thienyl or pyridyl group wherein one or two methyne groups are replaced by nitrogen atoms, or an indolyl, benzofuranyl, benzothiophenyl, quinolinyl or isoquinolinyl group wherein one to three methyne groups are replaced by nitrogen atoms, or a 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dihydro-2-oxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 3,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, cumarinyl, 2,3-dihydro-benzo[1,4]dioxinyl or 3,4-dihydro-3-oxo-2H-benzo[1,4]oxazinyl group, while the above-mentioned heteroaryl groups may be substituted by $R^{10}$ to $R^{14}$ where $R^{10}$ to $R^{14}$ are as hereinbefore defined, and, unless otherwise stated, the above-mentioned alkyl, alkenyl and alkynyl groups may be straight-chain or branched, as well as the derivatives which are N-oxidised or methylated or ethylated at the cyclic nitrogen atom in the 3 position or 9 position of the hypoxanthine skeleton, as well as the derivatives wherein the 6-oxo group of the hypoxanthine skeleton is replaced by a thioxo group, with the proviso that the compounds 8-(piperidin-4-ylmethyl)-7-(4-fluorobenzyl)-1,7-dihydro-purin-6-one and 8-(1-methyl-piperidin-4-ylmethyl)-7-(4-fluorobenzyl)-1,7-dihydro-purin-6-one are excluded, the tautomers, enantiomers, diastereomers, the mixtures thereof, the prodrugs thereof and the salts thereof.

Compounds which contain a group that can be cleaved in vivo are prodrugs of the corresponding compounds wherein this group that can be cleaved in vivo has been cleaved.

The carboxy groups mentioned in the definition of the above-mentioned groups may be replaced by a group which can be converted into a carboxy group in vivo or by a group which is negatively charged under physiological conditions, and furthermore the amino and imino groups mentioned in the definition of the above-mentioned groups may be substituted by a group which can be cleaved in vivo. Such groups are described for example in WO 98/46576 and by N. M. Nielsen et al. in International Journal of Pharmaceutics 39, 75-85 (1987).

By a group which can be converted in vivo into a carboxy group is meant, for example, a hydroxymethyl group, a carboxy group esterified with an alcohol wherein the alcohol moiety is preferably a $C_{1-6}$-alkanol, a phenyl-$C_{1-3}$-alkanol, a $C_{3-9}$-cycloalkanol, while a $C_{5-8}$-cycloalkanol may additionally be substituted by one or two $C_{1-3}$-alkyl groups, a $C_{5-8}$-cycloalkanol wherein a methylene group in the 3 or 4 position is replaced by an oxygen atom or by an imino group optionally substituted by a $C_{1-3}$-alkyl, phenyl-$C_{1-3}$-alkyl, phenyl-$C_{1-3}$-alkyloxycarbonyl or $C_{2-6}$-alkanoyl group and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or phenyl-$C_{3-5}$-alkynol with the proviso that no bonds to the oxygen atom start from a carbon atom which carries a double or triple bond, a $C_{3-8}$-cycloalkyl-$C_{1-3}$-alkanol, a bicycloalkanol with a total of 8 to 10 carbon atoms which may additionally be substituted in the bicycloalkyl moiety by one or two $C_{1-3}$-alkyl groups, a 1,3-dihydro-3-oxo-1-isobenzofuranol or an alcohol of formula

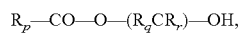

wherein $R_p$ denotes a $C_{1-8}$-alkyl, $C_{5-7}$-cycloalkyl, $C_{1-8}$-alkyloxy, $C_{5-7}$-cycloalkyloxy, phenyl or phenyl-$C_{1-3}$-alkyl group, $R_q$ denotes a hydrogen atom, a $C_{1-3}$-alkyl, $C_{5-7}$-cycloalkyl or phenyl group and $R_r$ denotes a hydrogen atom or a $C_{1-3}$-alkyl group, by a group which is negatively charged under physiological conditions is meant, for example, a tetrazol-5-yl, phenylcarbonylaminocarbonyl, trifluoromethylcarbonylaminocarbonyl, $C_{1-6}$-alkylsulphonylamino, phenylsulphonylamino, benzylsulphonylamino, trifluoromethylsulphonylamino, $C_{1-6}$-alkylsulphonylaminocarbonyl, phenylsulphonylaminocarbonyl, benzylsulphonylaminocarbonyl or perfluoro-$C_{1-6}$-alkylsulphonylaminocarbonyl group and by a group which can be cleaved in vivo from an imino or amino group is meant, for example, a hydroxy group, an acyl group such as a phenylcarbonyl group optionally mono- or disubstituted by fluorine, chlorine, bromine or iodine atoms, by $C_{1-3}$-alkyl or $C_{1-3}$-alkyloxy groups, while the substituents may be identical or different, a pyridinoyl group or a $C_{1-16}$-alkanoyl group such as the formyl, acetyl, propionyl, butanoyl, pentanoyl or hexanoyl group, a 3,3,3-trichloropropionyl or allyloxycarbonyl group, a $C_{1-16}$-alkyloxycarbonyl or $C_{1-16}$-alkylcarbonyloxy group, wherein hydrogen atoms may be wholly or partially replaced by fluorine or chlorine atoms such as the methoxycarbonyl, ethoxycarbonyl, propoxycarbonyl, isopropoxycarbonyl, butoxycarbonyl, tert.butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl, hexadecyloxycarbonyl, methylcarbonyloxy, ethylcarbonyloxy, 2,2,2-trichloroethylcarbonyloxy, propylcarbonyloxy, isopropylcarbonyloxy, butylcarbonyloxy, tert.butylcarbonyloxy, pentylcarbonyloxy, hexylcarbonyloxy, octylcarbonyloxy, nonylcarbonyloxy, decylcarbonyloxy, undecylcarbonyloxy, dodecylcarbonyloxy or hexadecylcarbonyloxy group, a phenyl-$C_{1-6}$-alkyloxycarbonyl group such as the benzyloxycarbonyl, phenylethoxycarbonyl or phenylpropoxycarbonyl group, a 3-amino-propionyl group wherein the amino group may be mono- or disubstituted by $C_{1-6}$-alkyl or $C_{3-7}$-cycloalkyl groups and the substituents may be identical or different, a $C_{1-3}$-alkylsulphonyl-$C_{2-4}$-alkyloxycarbonyl, $C_{1-3}$-alkyloxy-$C_{2-4}$-alkyloxy-$C_{2-4}$-alkyloxycarbonyl, $R_p$—CO—O—($R_qCR_r$)—O—CO, $C_{1-6}$-alkyl-CO—NH—($R_sCR_t$)—

O—CO— or $C_{1-6}$-alkyl-CO—O—$(R_sCR_t)$—$(R_sCR_t)$—O—CO— group, wherein $R_p$ to $R_r$ are as hereinbefore defined, $R_s$ and $R_t$, which may be identical or different, denote hydrogen atoms or $C_{1-3}$-alkyl groups.

Moreover, the saturated alkyl and alkyloxy moieties which contain more than 2 carbon atoms mentioned in the foregoing definitions and those that follow, unless otherwise stated, also include the branched isomers thereof such as, for example, the isopropyl, tert.butyl, isobutyl group, etc.

One sub-group deserving special mention relates to those compounds of general formula I wherein $R^1$, $R^2$ and $R^3$ are as hereinbefore defined and $R^4$ denotes a pyrrolidin-1-yl group which is substituted in the 3 position by an amino group, a piperidin-1-yl group which is substituted in the 3 position by an amino group, a piperidin-3-yl or piperidin-4-yl group, a hexahydroazepin-1-yl group which is substituted in the 3 position or 4 position by an amino group, a piperazin-1-yl or [1,4]diazepan-1-yl group, a (2-aminocyclohexyl)amino group, a cyclohexyl group which is substituted in the 3 position by an amino group, or an N-(2-aminoethyl)-methylamino or an N-(2-aminoethyl)-ethylamino group, the tautomers, enantiomers, diastereomers, the mixtures thereof, the prodrugs and the salts thereof.

Preferred compounds of the above general formula I are those wherein $R^1$ denotes a hydrogen atom,
a $C_{1-6}$-alkyl group,
a $C_{3-6}$-alkenyl group,
a $C_{3-4}$-alkynyl group,
a $C_{3-6}$-cycloalkylmethyl group,
a phenyl-$C_{1-3}$-alkyl group wherein the phenyl moiety is substituted by $R^{10}$ and $R^{11}$, where $R^{10}$ denotes a hydrogen atom, a fluorine, chlorine or bromine atom,
a methyl or trifluoromethyl group,
a cyano, aminocarbonyl, dimethylaminocarbonyl or methylsulphonyl group,
an amino, acetylamino or methylsulphonylamino group,
a hydroxy, methoxy, difluoromethoxy, trifluoromethoxy, carboxymethoxy, methoxycarbonylmethoxy, ethyloxycarbonylmethoxy, aminocarbonylmethoxy, methylaminocarbonylmethoxy, ethylaminocarbonylmethoxy or dimethylaminocarbonylmethoxy group and $R^{11}$ denotes a hydrogen atom, a fluorine or chlorine atom, or a methyl or methoxy group, a naphthylmethyl group wherein the naphthyl moiety is substituted by $R^{10}$ and $R^{11}$, where $R^{10}$ and $R^{11}$ are as hereinbefore defined, a heteroarylmethyl group where the term
heteroaryl denotes a furanyl, thienyl, oxazolyl, isoxazolyl, thiazolyl, pyridyl, pyrimidinyl, pyrazinyl, quinolinyl, isoquinolinyl or quinazolinyl group and the above-mentioned heteroaryl groups are substituted by $R^{10}$ and $R^{11}$, where $R^{10}$ and $R^{11}$ are as hereinbefore defined, a phenylcarbonylmethyl group wherein the phenyl moiety is substituted by $R^{10}$ and $R^{11}$, where $R^{10}$ and $R^{11}$ are as hereinbefore defined, a furanylcarbonylmethyl, thienylcarbonylmethyl or pyridylcarbonylmethyl group, or a 2-oxo-propyl or cyclohexylcarbonylmethyl group, $R^2$ denotes a hydrogen atom,
a $C_{1-6}$-alkyl group,
a $C_{3-6}$-alkenyl group,
a $C_{3-4}$-alkynyl group,
a $C_{3-6}$-cycloalkyl or $C_{3-6}$-cycloalkyl-$C_{1-3}$-alkyl group,
a phenyl group which is substituted by $R^{10}$ and $R^{11}$, where $R^{10}$ and $R^{11}$ are as hereinbefore defined,
a phenyl-$C_{1-3}$-alkyl group wherein the phenyl moiety is substituted by $R^{10}$ and $R^{11}$, where $R^{10}$ and $R^{11}$ are as hereinbefore defined,
a phenyl-$C_{2-3}$-alkenyl group wherein the phenyl moiety is substituted by $R^{10}$ and $R^{11}$, where $R^{10}$ and $R^{11}$ are as hereinbefore defined,
a phenylcarbonylmethyl group wherein the phenyl moiety is substituted by $R^{10}$ and $R^{11}$, where $R^{10}$ and $R^{11}$ are as hereinbefore defined,
a furanyl, thienyl or pyridyl group,
a furanyl-$C_{1-3}$-alkyl, thienyl-$C_{1-3}$-alkyl or pyridyl-$C_{1-3}$-alkyl group,
a cyano group,
an amino, $C_{1-4}$-alkylamino or di-($C_{1-4}$-alkyl)-amino group,
an amino group substituted by the groups $R^{15}$ and $R^{16}$ wherein
$R^{15}$ denotes a hydrogen atom or a methyl or ethyl group and
$R^{16}$ denotes a $C_{1-4}$-alkyl group which is substituted by a cyano, carboxy, methoxycarbonyl, ethyloxycarbonyl, aminocarbonyl, methylaminocarbonyl, dimethylaminocarbonyl, ethylaminocarbonyl, diethylaminocarbonyl, pyrrolidin-1-ylcarbonyl or morpholin-4-ylcarbonyl group,
an amino group substituted by the groups $R^{15}$ and $R^{17}$ wherein
$R^{15}$ is as hereinbefore defined and
$R^{17}$ denotes a straight-chain $C_{2-4}$-alkyl group which is terminally substituted in each case by an amino, methylamino, dimethylamino, acetylamino, ethyloxy-carbonylamino, phenylcarbonylamino, methylsulphonylamino, phenylsulphonylamino, hydroxy, methoxy, phenyloxy, methylsulphanyl or phenylsulphanyl group,
a pyrrolidin-1-yl, piperidin-1-yl, morpholin-4-yl, piperazin-1-yl or 4-methyl-piperazin-1-yl group,
a $C_{3-6}$-cycloalkylamino or $C_{3-6}$-cycloalkyl-$C_{1-3}$-alkylamino group,
a phenylamino group,
a phenyl-$C_{1-3}$-alkylamino group wherein the phenyl moiety is substituted by $R^{10}$ and $R^{11}$, where $R^{10}$ and $R^{11}$ are as hereinbefore defined,
a naphthylmethylamino group,
a heteroaryl-$C_{1-2}$-alkylamino group, where the term heteroaryl is as hereinbefore defined, or
a methylsulphanyl, benzylsulphanyl or (2-phenylethyl)sulphanyl group, $R^3$ denotes a $C_{4-6}$-alkenyl group,
a $C_{3-4}$-alkenyl group which is substituted by a fluorine, chlorine or bromine atom or a trifluoromethyl group,
a 2-butyn-1-yl group or
a methyl group substituted by the group $R_c$, where
$R_c$ denotes a 1-cyclopenten-1-yl-or 1-cyclohexen-1-yl group,
a phenyl group optionally substituted by a fluorine, chlorine, bromine or iodine atom, by a methyl, trifluoromethyl, cyano, methoxy, difluoromethoxy or trifluoromethoxy group,
a phenyl group which is substituted by two fluorine atoms,
a naphthyl group or
a furanyl, thienyl, or pyridyl group,
and R⁴ denotes a piperidin-1-yl group which is substituted in the 3 position by an amino group,
a hexahydroazepin-1-yl group which is substituted in the 3 position or 4 position by an amino group,
a (2-aminocyclohexyl)amino group,
a cyclohexyl group which is substituted in the 3 position by an amino group, or
an N-(2-aminoethyl)-methylamino or an N-(2-aminoethyl)-ethylamino group,
while unless otherwise stated, the above-mentioned alkyl alkenyl and alkynyl groups may be straight-chain or branched,
the tautomers, enantiomers, diastereomers, the mixtures thereof and the salts thereof.

Particularly preferred compounds of the above general formula I are those wherein
$R^1$ denotes a hydrogen atom,
a methyl, benzyl or 2-phenylethyl group,
a naphthylmethyl or methoxynaphthylmethyl group or
a phenylcarbonylmethyl group,
$R^2$ denotes a hydrogen atom,
a methyl or 2-phenylethyl group,
a phenylcarbonylmethyl group,
a cyano group,
an amino, methylamino, dimethylamino, isopropylamino, cyclohexylamino- or (cyclohexylmethyl)amino group,
a benzylamino, fluorobenzylamino or (2-phenylethyl) amino group or
a piperidin-1-yl group,
$R^3$ denotes a benzyl or 3-methyl-but-2-en-1-yl group and
$R^4$ denotes a (3-amino-piperidin-1-yl) group,
the tautomers, enantiomers, diastereomers, the mixtures thereof and the salts thereof,
but particularly the compounds
(1) 8-(3-amino-piperidin-1-yl)-7-benzyl-2-benzylamino-1-methyl-1,7-dihydro-purin-6-one,
(2) 8-(3-amino-piperidin-1-yl)-7-benzyl-2-(4-fluoro-benzylamino)-1-methyl-1,7-dihydro-purin-6-one,
(3) 8-(3-amino-piperidin-1-yl)-7-benzyl-1-methyl-2-[(2-phenylethyl)amino]-1,7-dihydro-purin-6-one,
(4) 8-(3-amino-piperidin-1-yl)-7-benzyl-2-isopropylamino-1-methyl-1,7-dihydro-purin-6-one,
(5) 8-(3-amino-piperidin-1-yl)-7-benzyl-1-methyl-2-methylamino-1,7-dihydro-purin-6-one,
(6) 8-(3-amino-piperidin-1-yl)-7-benzyl-2-cyclohexylamino-1-methyl-1,7-dihydro-purin-6-one,
(7) 8-(3-amino-piperidin-1-yl)-7-benzyl-2-[(cyclohexylmethyl)amino]-1-methyl-1,7-dihydro-purin-6-one,
(8) 8-(3-amino-piperidin-1-yl)-7-benzyl-1-methyl-2-(piperidin-1-yl)-1,7-dihydro-purin-6-one,
(9) 8-(3-amino-piperidin-1-yl)-7-benzyl-2-dimethylamino-1-methyl-1,7-dihydro-purin-6-one,
(10) 2-amino-8-(3-amino-piperidin-1-yl)-7-benzyl-1-methyl-1,7-dihydro-purin-6-one,
(11) 8-(3-amino-piperidin-1-yl)-2-benzylamino-1-methyl-7-(3-methyl-but-2-en-1-yl)-1,7-dihydro-purin-6-one,
(12) 8-(3-amino-piperidin-1-yl)-7-benzyl-1-methyl-2-methyl-1,7-dihydro-purin-6-one,
(13) 8-(3-amino-piperidin-1-yl)-1-methyl-7-(3-methyl-but-2-en-1-yl)-2-(2-phenyl-ethyl)-1,7-dihydro-purin-6-one,
(14) 8-(3-amino-piperidin-1-yl)-7-benzyl-1-methyl-1,7-dihydro-purin-6-one,
(15) 8-(3-amino-piperidin-1-yl)-7-benzyl-1-(2-oxo-2-phenyl-ethyl)-1,7-dihydro-purin-6-one,
(16) 8-(3-amino-piperidin-1-yl)-2-methyl-7-(3-methyl-but-2-en-1-yl)-1-[(naphthalen-1-yl)methyl]-1,7-dihydro-purin-6-one,
(17) 8-(3-amino-piperidin-1-yl)-7-(3-methyl-but-2-en-1-yl)-1-[(naphthalen-1-yl)methyl]-1,7-dihydro-purin-6-one and
(18) 8-(3-amino-piperidin-1-yl)-7-(3-methyl-but-2-en-1-yl)-1-[(4-methoxy-naphthalen-1-yl)methyl]-1,7-dihydro-purin-6-one as well as the tautomers, enantiomers, diastereomers, the mixtures thereof and the salts thereof.

The compounds of general formula I can be prepared by deprotecting a compound of general formula (II)

wherein $R^1$, $R^2$ and $R^3$ are as hereinbefore defined and
$R^{4'}$ denotes one of the groups mentioned hereinbefore for $R^4$ which contain an imino, amino or alkylamino group, while the imino, amino or alkylamino group is substituted by a protective group, optionally followed by subsequent alkylation of the imino, amino or $C_{1-3}$-alkylamino group.

The liberating of an amino group from a protected precursor is a standard reaction in synthetic organic chemistry. There are many examples of suitable protective groups. A summary of the chemistry of protective groups can be found in Theodora W. Greene and Peter G. M. Wuts, Protective Groups in Organic Synthesis, Second Edition, 1991, published by John Wiley and Sons, and in Philip J. Kocienski, Protecting Groups, published by Georg Thieme, 1994.

The following are examples of protective groups:
the tert.-butyloxycarbonyl group which can be cleaved by treating with an acid such as for example trifluoroacetic acid or hydrogen chloride in the presence of a solvent such as for example methylene chloride, ethyl acetate or dioxane at temperatures between 0° C. and the boiling temperature of the solvent used, the 2,2,2-trichloroethoxycarbonyl group which can be cleaved by treating with metals such as for example zinc or cadmium in a solvent such as acetic acid or a mixture of tetrahydrofuran and a weak aqueous acid at temperatures between 0° C. and the boiling temperature of the solvent used and the carbobenzyloxycarbonyl group which can be cleaved for example by hydrogenolysis in the presence of a noble metal catalyst such as for example palladium-charcoal and a solvent such as for example alcohols, ethyl acetate, dioxane, tetrahydrofuran or mixtures of these solvents at temperatures between 0° C. and the boiling point of the solvent, by treating with boron tribromide in methylene chloride at temperatures between −20° C. and ambient temperature, or by treating with aluminum chloride/anisol at temperatures between 0° C. and ambient temperature.

The optional subsequent introduction of a $C_{1-3}$-alkyl group may be done by alkylation or reductive alkylation.

The subsequent alkylation is optionally carried out in a solvent or mixture of solvents such as methylene chloride, dimethylformamide, benzene, toluene, chlorobenzene, tetrahydrofuran, benzene/tetrahydrofuran or dioxane with an alkylating agent such as a corresponding halide or sulphonic acid ester, e.g. with methyl iodide, ethyl bromide, dimethyl sulphate, optionally in the presence of a tertiary organic base or in the presence of an inorganic base, conveniently at temperatures between 0 and 150° C., preferably at temperatures between 0 and 100° C.

The subsequent reductive alkylation is carried out with a corresponding carbonyl compound such as formaldehyde, acetaldehyde, propionaldehyde or acetone in the presence of a complex metal hydride such as sodium borohydride, lithium borohydride, sodium triacetoxyborohydride or sodium cyanoborohydride, conveniently at a pH of 6-7 and at ambient temperature or in the presence of a hydrogenation catalyst, e.g. with hydrogen in the presence of palladium/charcoal, under a hydrogen pressure of 1 to 5 bar. The methylation may also be carried out in the presence of formic acid as reducing agent at elevated temperatures, e.g. at temperatures between 60 and 120° C.

The compounds of general formula I obtained may be resolved into their enantiomers and/or diastereomers. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, methane sulphonic acid, phosphoric acid, fumaric acid, succinic acid, lactic acid, citric acid, tartaric acid or maleic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The starting compounds of general formula II may be prepared by generally known methods and according to processes described for example in Examples 1 to XIV.

Thus, compounds of general formula II wherein $R^1$, $R^3$ and $R^{4'}$ are as hereinbefore defined and $R^2$ denotes a hydrogen atom, may be prepared for example by reacting a compound of formula

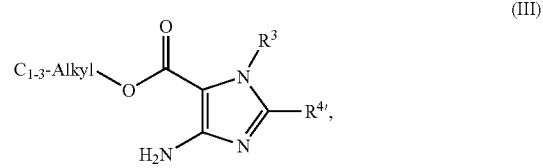

(III)

with a formimido-$C_{1-3}$-alkyl ester, optionally followed by alkylation at N–1 with a suitable alkylating agent.

Compounds of general formula II wherein $R^1$, $R^3$ and $R^{4'}$ are as hereinbefore defined and $R^2$ denotes an alkylsulphanyl, an alkenylsulphanyl or alkynylsulphanyl group may be obtained for example by reacting compounds of general formula III with a suitable isothiocyanate and subsequently cyclising them to form compounds of general formula

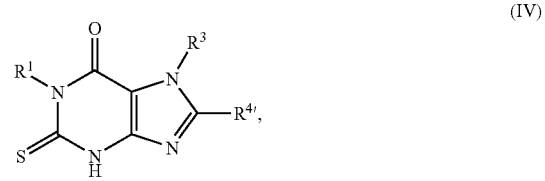

(IV)

followed by alkylation of the sulphur atom.

If an acyl mustard oil is used, such as for example ethoxycarbonylisothiocyanate, first of all compounds of general formula IV, wherein $R^1$ denotes a hydrogen atom are obtained, which can be converted into the desired compounds by subsequent alkylation at the sulphur atom and at N–1.

Compounds of general formula II wherein $R^1$, $R^3$ and $R^{4'}$ are as hereinbefore defined and $R^2$ denotes an alkylsulphanyl group can be oxidised to form compounds of formula II' wherein $R^{2'}$ denotes an alkylsulphinyl or an alkylsulphonyl group.

The above-mentioned compounds of general formula II' are starting materials for preparing the following compounds of formula II.

Reaction with alcohols and phenols yields compounds wherein the group $R^2$ is linked to the purine system via an oxygen atom, Reaction with thiols and thiophenols leads to compounds wherein $R^2$ is linked to the purine system via a sulphur atom, Reaction with amines leads to compounds wherein $R^2$ is bound to the purine system via a nitrogen atom and Reaction with organometallic compounds such as for example Grignard reagents, alkyl- or aryl-lithium compounds or reaction with CH-acid compounds such as for example esters, nitrites or ketones leads to compounds wherein $R^2$ is linked to the purine system via a carbon atom.

Another method of obtaining compounds of general formula II consists, for example, in converting compounds of general formula

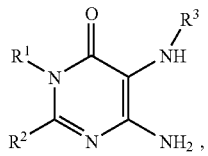

(V)

wherein $R^1$, $R^2$ and $R^3$ are as hereinbefore defined, into compounds of general formula II.

For example, compounds of general formula V are converted into compounds of general formula II wherein the group $R^{4'}$ is bound to the purine system via a nitrogen atom, by reacting with an orthoformate, subsequently brominating the resulting purine at C-8 and then reacting with a corresponding amine.

For example, compounds of general formula V are converted into compounds of general formula II wherein the group $R^{4'}$ is bound to the C-8 atom of the purine via a C-atom by reaction with a reactive derivative of a carboxylic acid $R^{4'}$—COOH, where R4' is as hereinbefore defined, and subsequent cyclisation.

As already mentioned hereinbefore, the compounds of general formula I according to the invention and the physiologically acceptable salts thereof have valuable pharmacological properties, particularly an inhibiting effect on the enzyme DPP-IV.

The biological properties of the new compounds were investigated as follows:

The ability of the substances and their corresponding salts to inhibit the DPP-IV activity can be demonstrated in a test set-up in which an extract of human colon carcinoma cell line Caco-2 is used as the DPP IV source. The differentiation of the cells in order to induce the DPP-IV expression was carried out as described by Reiher et al. in an article entitled "Increased expression of intestinal cell line Caco-2", which appeared in Proc. Natl. Acad. Sci. Vol. 90, pages 5757-5761 (1993). The cell extract was obtained from cells solubilised in a buffer (10 mM Tris HCl, 0.15 M NaCl, 0.04 t.i.u. aprotinin, 0.5% Nonidet-P40, pH 8.0) by centrifuging at 35,000 g for 30 minutes at 4° C. (to remove cell debris).

The DPP-IV assay was carried out as follows:

50 µl substrate solution (AFC; AFC is amido-4-trifluoromethylcoumarin), final concentration 100 µM, were placed in black microtitre plates. 20 µl of assay buffer (final concentrations 50 mM Tris HCl pH 7.8, 50 mM NaCl, 1% DMSO) was pipetted in. The reaction was started by adding 30 µl of solubilised Caco-2 protein (final concentration 0.14 µg of protein per well). The test substances to be investigated were typically added prediluted in 20 µl, and the volume of assay buffer was then reduced accordingly. The reaction was carried out at ambient temperature, incubating for 60 minutes. Then the fluorescence was measured in a Victor 1420 Multilabel Counter, the excitation wavelength being 405 nm and the emission wavelength being 535 nm. Blank readings (corresponding to 0% activity) were obtained in mixtures without any Caco-2 protein (volume replaced by assay buffer), control values (corresponding to 100% activity) were obtained in mixtures with no substance added. The potency of the test substances in question, expressed as $IC_{50}$ values, was calculated from dosage/activity curves consisting of 11 measuring points in each case.

The results obtained are shown in the following Table:

| Compound (Example No.) | DPP IV inhibition $IC_{50}$ (nM) |
|---|---|
| 1 | 11 |
| 1(1) | 24 |
| 1(2) | 42 |
| 1(3) | 110 |
| 1(4) | 58 |
| 1(5) | 134 |
| 1(6) | 48 |
| 1(7) | 434 |
| 1(8) | 213 |
| 1(9) | 61 |
| 1(11) | 54 |
| 1(12) | 18 |
| 1(13) | 152 |
| 1(14) | 158 |
| 1(15) | 58 |
| 1(22) | 48 |
| 1(23) | 157 |
| 1(24) | 113 |
| 1(25) | 275 |
| 1(26) | 40 |
| 1(27) | 19 |
| 1(28) | 57 |

The compounds prepared according to the invention are well tolerated, as for example when 30 mg/kg of the compound of Example 1 were administered to rats by oral route no toxic side effects or changes in the animals' behaviour could be detected.

In view of their ability to inhibit DPP-IV activity, the compounds of general formula I according to the invention and the corresponding pharmaceutically acceptable salts thereof are suitable for treating all those conditions or illnesses which can be influenced by the inhibition of the DPP-IV activity. It is therefore to be expected that the compounds according to the invention will be suitable for the prevention or treatment of diseases or conditions such as type 1 and type 2 diabetes mellitus, diabetic complications (such as e.g. retinopathy, nephropathy or neuropathies), metabolic acidosis or ketosis, reactive hypoglycaemia, insulin resistance, metabolic syndrome, dyslipidaemias of various origins, arthritis, atherosclerosis and related diseases, obesity, allograft transplantation and calcitonin-induced osteoporosis. In addition these substances are capable of preventing B-cell degeneration such as e.g. apoptosis or necrosis of pancreatic B-cells. The substances are also suitable for improving or restoring the function of pancreatic cells and also increasing the number and size of pancreatic B-cells. Additionally, and on the basis of the role of the Glucagon-Like Peptides, such as e.g. GLP-1 and GLP-2 and their link with DPP-IV inhibition, it is likely that the compounds according to the invention are suitable for achieving, inter alia, a sedative or anxiety-relieving effect and also of favourably affecting catabolic states after operations or hormonal stress responses or of reducing mortality or morbidity after myocardial infarct. They are also suitable for treating all conditions which are connected with the above-mentioned effects and which are mediated by GLP-1 or GLP-2. The compounds according to the invention may also be used as diuretics or antihypertensives and are suitable for preventing and treating acute renal failure. Furthermore, the compounds according to the invention may be used to treat inflammatory diseases of the respiratory tract. They are also suitable for the prevention and treatment of chronic inflammatory intestinal diseases such as e.g. irritable bowel syndrome (IBS), Crohn's disease or ulcerative colitis and also pancreatitis. It is also likely that they can be used for all kinds of damage to or impairment of the gastrointestinal tract such as colitis and enteritis, for example. It is also expected that DPP-IV inhibitors and hence also the compounds according to the invention may be used to treat infertility or to improve fertility in humans or mammals, particularly when the infertility is connected with insulin resistance or polycystic ovary syndrome. On the other hand these substances are suitable for affecting sperm motility and can thus be used as male contraceptives. The substances are also suitable for treating deficiencies of growth hormone which are associated with reduced stature, and may also be used to advantage in any indications in which growth hormone may be used. The compounds according to the invention are also suitable, on the basis of their inhibitory effect on DPP IV, for treating various autoimmune diseases such as e.g. rheumatoid arthritis, multiple sclerosis, thyroiditis and Basedow's disease, etc. They may also be used to treat viral diseases and also, for example, in HIV infections, for stimulating blood production, in benign prostatic hyper-plasia, gingivitis, as well as for the treatment of neuronal defects and neurodegenerative diseases such as Alzheimer's disease, for example. The compounds described may also be used for the treatment of tumours, particularly for modifying tumour invasion and also metastasisation; examples here are their use in treating T-cell lymphomas, acute lymphoblastic leukaemia, cell-based pancreatic carcinomas, basal cell carcinomas or breast cancers. Other indications are stroke, ischaemia of various origins, Parkinson's disease and migraine. In addition, further indications include follicular and epidermal hyperkeratoses, increased keratinocyte proliferation, psoriasis, encephalomyelitis, glomerulonephritis, lipodystrophies, as well as psychosomatic, depressive and neuropsychiatric diseases of all kinds.

The compounds according to the invention may also be used in conjunction with other active substances. Therapeutic agents which are suitable for such combinations include, for example, antidiabetics, such as metformin, sulphonylureas (e.g. glibenclamid, tolbutamide, glimepiride), nateglinide, repaglinide, thiazolidinedione (e.g. rosiglitazone, pioglitazone), PPAR-gamma agonists (e.g. GI 262570) and antagonists, PPAR-gamma/alpha modulators (e.g. KRP 297), alpha-glucosidase inhibitors (e.g. acarbose, voglibose), other DPPIV inhibitors, alpha2 antagonists, insulin and insulin analogues, GLP-1 and GLP-1 analogues (e.g. exendin-4) or amylin. Also, inhibitors of protein tyrosine phosphatase 1, substances which influence deregulated glucose production in the liver, such as e.g. inhibitors of glucose-6-phosphatase, or fructose-1,6-bisphosphatase, glycogen phosphorylase, glucagon receptor antagonists and inhibitors of phosphoenol—pyruvate carboxykinase, glycogen synthase kinase or pyruvate dehydrokinase, lipid lowering agents, such as HMG-CoA-reductase inhibitors (e.g. simvastatin, atorvastatin), fibrates (e.g. bezafibrate, fenofibrate), nicotinic acid and its derivatives, PPAR-alpha agonists, PPAR-delta agonists, ACAT inhibitors (e.g. avasimibe) or cholesterol—resorption inhibitors such as for example ezetimibe, bile acid-binding substances such as for example cholestyramine, inhibitors of ileac bile acid transport, HDL-raising compounds such as for example inhibitors of CETP or regulators of ABC 1 or active substances for the treatment of obesity such as e.g. sibutramine or tetrahydrolipostatin, dexfenfluramine, axokine, antagonists of the cannabinoid1 receptor, MCH-1 receptor antagonists, $MC_4$ receptor agonists, NPY5 or NPY2 antagonists or $\beta_3$-agonists such as SB-418790 or AD-9677 as well as agonists of the 5HT2c receptor.

It is also possible to combine the compounds with drugs for treating high blood pressure such as e.g. All antagonists or ACE inhibitors, diuretics, β-blockers, Ca-antagonists, etc., or combinations thereof.

The dosage required to achieve such an effect is expediently, by intravenous route, 1 to 100 mg, preferably 1 to 30 mg, and by oral route 1 to 1000 mg, preferably 1 to 100 mg, in each case 1 to 4 a day. For this purpose, the compounds of formula I prepared according to the invention, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The Examples that follow are intended to illustrate the invention:

Preparation of the starting compounds:

EXAMPLE I

Ethyl 5-amino-3-benzyl-2-(3-tert.-butyloxycarbony-lamino-piperidin-1-yl)-3H-imidazol-4-carboxylate 50 g (0.199 mol) of N-benzyl-N'-cyano-O-phenyl-isourea and 40.056 g (0.2 mol) of 3-tert.-butyloxycarbonylamino-piperidine are heated to 80° C. in 50 ml of dimethylformamide (DMF) for 4 hours. After standing overnight 250 ml of ethyl acetate are added, the precipitate is suction filtered, washed with ethyl acetate and ether and dried. More product is obtained from the mother liquor after evaporation and treatment of the residue with ethyl acetate and ether. Total yield: 48.0 g (67.5% of theory) of N-benzyl-N'-cyano-(3-tert.-butyloxy-carbonylamino-piperidin)-1-carboxamidine.

$R_f$ value: 0.56 (aluminium oxide, methylene chloride/methanol=40:1)

10.008 g (28 mmol) of this substance are dissolved in 15 ml DMF. After the addition of 4.256 g (30.8 mmol) of potassium carbonate the mixture is treated with ultrasound for three minutes, then 3.416 ml (30.8 mmol) of ethyl bromoacetate are added in one go and the mixture is stirred for 36 hours at ambient temperature, adding another 10 ml of DMF after 8 hours for ease of stirring. The reaction mixture is stirred with water, extracted with ethyl acetate, the organic phase is dried and concentrated by evaporation. The resin obtained is purified by column chromatography (silica gel, ethyl acetate/petroleum ether=3:1 to 9:1)

5.4 g (43.5% of theory) of N-benzyl-N'-cyano-N-ethoxy-carbonylmethyl-(3-tert.-butyloxy-carbonylamino-piperidin)-1-carboxamidine are obtained.

$R_f$ value: 0.7 (silica gel, ethyl acetate/petroleum ether=4:1)

5.1 g (11.498 mmol) of this compound are added batchwise to a solution of 0.785 g (11.536 mmol) of sodium ethoxide in 25 ml of ethanol. The mixture is stirred for 40 minutes at 60° C., then combined with 50 ml of ethanol and 10 ml of water and cooled. The precipitate is suction filtered and dissolved in methylene chloride. After drying and evaporation of the solvent, 4.8 g (94.1% of theory) of the title compound is obtained.

$R_f$ value: 0.4 (silica gel, ethyl acetate/petroleum ether=4:1)

The following was obtained analogously to Example I:

(1) ethyl5-amino-3-(3-methyl-but-2-enyl)-2-(3-tert.-butyloxycarbonylamino-piperidin-1-yl)-3H-imidazol-4-carboxylate prepared from diphenyl-N-cyanocarbonimidate, glycinethylester, (3-tert.-butyloxy-carbonylamino)-piperidine and 3-methyl-but-2-en-1-yl-bromide.

$R_f$ value: 0.1-0.2 (silica gel, ethyl acetate/petroleum ether=1:1)

EXAMPLE II tert.butyl[1-(7-benzyl-6-oxo-6,7-dihydro-1H-purin-8-yl)-piperidin-3-yl]carbaminate 360 mg (0.812 mmol) of ethyl 5-amino-3-benzyl-2-(3-tert.-butyloxy-carbonylamino-piperidin-1-yl)-3H-imidazol-4-carboxylate and 131.472 (1.2 mmol) of ethylformidate hydrochloride are placed in 1.3 g phenol. A solution of 141.667 mg (2mmol) of sodiumethoxide in 2 ml of tetrahydrofuran (THF) is added dropwise with stirring, the THF is evaporated off and the mixture is kept for 2 hours at 150° C. The brown reaction mixture is purified through a silica gel column. 50 mg (15.7% of theory) of the title compound were obtained.

melting point: 208° C. $R_f$ value: 0.15 (silica gel, methylene chloride/methanol=15:1)

EXAMPLE III tert.butyl[1-(7-benzyl-1-methyl-6-oxo-6,7-dihydro-1H-purin-8-yl)-piperidin-3-yl]carbaminate 19 mg (0.138 mmol) of potassium carbonate and then 16 mg (0.113 mmol) of methyl iodide are added to a solution of 42 mg (0.099 mmol) of the compound of Example II in 0.3 ml DMF. The mixture is stirred for 2 hours at ambient temperature, then triturated with water and extracted with ethyl acetate. The organic phase is washed with water and dried with activated charcoal and magnesium sulphate. After evaporation 29 mg (66.8% of theory) of the title compound is obtained.

$R_f$ value: 0.3 (silica gel, methylene chloride/methanol=15:1)

The following was obtained analogously to Example III:
(1) tert.butyl[1-(7-benzyl-1-{2-oxo-2-phenyl-ethyl}-6-oxo-6,7-dihydro-1H-purin-8-yl)-piperidin-3-yl]-carbaminate
prepared from Example II and phenacylbromide.

$R_f$ value: 0.4 (silica gel, methylene chloride/methanol=15:1)

EXAMPLE IV tert.butyl[1-(7-benzyl-2-methylsulphanyl-6-oxo-6,7-dihydro-1H-purin-8-yl)-piperidin-3-yl]-carbaminate 3.186 ml (27 mmol) of ethyloxycarbonyl isothiocyanate are added dropwise to a solution of 10.8 g (24.345 mmol) of the compound of Example 1 in 45 ml THF. The mixture is heated to boiling for one hour, concentrated by evaporation and the residue is brought to crystallisation by treating with diisopropylether.

13.5 g (96.5% of theory) of ethyl 3-benzyl-2-(3-tert.-butyloxycarbonylamino-piperidin-1-yl)-5-(N'-ethyloxycarbonyl-thioureido)-3H-imidazol-4-carboxylate are obtained.

13 g (22.620 mmol) of this compound are placed in 21 ml of n-butanol. After the addition of 2.536 (22.6 mmol) of potassium-tert.-butoxide the mixture is stirred for 45 minutes at 100° C., during which time a precipitate settles out. After standing overnight at ambient temperature the mixture is combined with ether, suction filtered and dried. 10.6 g (94.7% of theory) of tert.butyl[1-(7-benzyl-2-mercapto-6-oxo-6,7-dihydro-1H-purin-8-yl)-piperidin-3-yl]-carbaminate potassium salt are obtained.

10.5 g (21.225 mmol) of this compound are suspended in 25 ml of water, and ethanol is added to the solution. After the addition of 2.135 ml (21.515 mmol) of dimethylsulphate the mixture is stirred for 4 hours at ambient temperature. The precipitate is suction filtered, washed with cold ethanol and dried. 8.8 g (88.1% of theory) of the title compound are obtained.

$R_f$ value: 0.3 (silica gel, methylene chloride/methanol=20:1)

The following compounds were obtained analogously to Example IV:
(1) tert.butyl[1-(7-benzyl-2-benzylsulphanyl-6-oxo-6,7-dihydro-1H-purin-8-yl)-piperidin-3-yl]-carbaminate
prepared from compound I, ethyloxycarbonyl isothiocyanate and benzylbromide.

$R_f$ value: 0.65 (silica gel, ethyl acetate/petroleum ether=2:1)
(2) tert.butyl[1-(7-allyl-2-methylsulphanyl-6-oxo-6,7-dihydro-1H-purin-8-yl)-piperidin-3-yl]-carbaminate
prepared from compound I.1, ethyloxycarbonyl isothiocyanate and methyl iodide.

$R_f$ value: 0.6 (silica gel, methylene chloride/methanol=10:1)
(3) tert.butyl[1-(7-benzyl-2-[2-phenylethyl]sulphanyl-6-oxo-6,7-dihydro-1H-purin-8-yl)-piperidin-3-yl]-carbaminate
prepared from compound I, ethyloxycarbonyl isothiocyanate and 2-phenylethylbromide.

$R_f$ value: 0.65 (silica gel, ethyl acetate/petroleum ether=2:1)

EXAMPLE V tert-butyl[1-(7-benzyl-1-methyl-2-methylsulphanyl-6-oxo-6,7-dihydro-1H-purin-8-yl)-piperidin-3-yl]-carbaminate A suspension of 2.5 g (5.312 mmol) of compound IV in 15 ml DMF is combined with 645.15 mg (5.75mmol) of potassium-tert.-butoxide. 922.605 mg (6.5 mmol) of methyl iodide are added to the resulting solution and the mixture is stirred overnight at ambient temperature. Water is added and the mixture is extracted with methylene chloride. The organic phase is washed with water, dried and concentrated by evaporation. The residue is crystallised with diisopropylether. 2 g (77.7% of theory) of the title compound are obtained.

$R_f$ value: 0.55 (silica gel, methylene chloride/methanol=20:1)

The following compounds were obtained analogously to Example V:
(1) tert.butyl[1-(7-benzyl-2-methylsulphanyl-1-phenacyl-6-oxo-6,7-dihydro-1H-purin-8-yl)-piperidin-3-yl]-carbaminate
prepared from compound IV and phenacylbromide.

$R_f$ value: 0.7 (aluminium oxide, methylene chloride/methanol=40:1)
(2) tert.butyl[1-(1-methyl-7-(3-methyl-butenyl)-2-methylsulphanyl-6-oxo-6,7-dihydro-1H-purin-8-yl)-piperidin-3-yl]-carbaminate
prepared from compound IV.1 and methyl iodide.

$R_f$ value: 0.4 (silica gel, methylene chloride/methanol=20:1)

(3)  tert.butyl[1-(1-benzyl-7-benzyl-2-methylsulphanyl-6-oxo-6,7-dihydro-1H-purin-8-yl)-piperidin-3-yl]-carbaminate prepared from compound IV and benzylbromide.

$R_f$ value: 0.75 (silica gel, ethyl acetate/petroleum ether=4:1)

(4)  tert.butyl[1-(7-benzyl-2-methylsulphanyl-1-(2-phenylethyl)-6-oxo-6,7-dihydro-1H-purin-8-yl)-piperidin-3-yl]-carbaminate prepared from compound IV and 2-phenylethylbromide.

$R_f$ value: 0.75 (silica gel, ethyl acetate/petroleum ether=4:1)

(5)  tert.butyl[1-(7-benzyl-2-benzylsulphanyl-1-methyl-6-oxo-6,7-dihydro-1H-purin-8-yl)-piperidin-3-yl]-carbaminate prepared from compound IV.1 and methyl iodide.

$R_f$ value: 0.85 (silica gel, ethyl acetate/petroleum ether=1:2)

(6) tert.butyl[1-(7-benzyl-2-[2-phenylethyl]sulphanyl-1-methyl-6-oxo-6,7-dihydro-1H-purin-8-yl)-piperidin-3-yl]-carbaminate prepared from compound IV.3 and methyl iodide.

$R_f$ value: 0.65 (silica gel, ethyl acetate/petroleum ether=1:2)

EXAMPLE VI tert.butyl[1-(7-benzyl-1-methyl-2-methylsulphinyl-6-oxo-6,7-dihydro-1H-purin-8-yl)-piperidin-3-yl]-carbaminate and tert.butyl[1-(7-benzyl-1-methyl-2-methylsulphonyl-6-oxo-6,7-dihydro-1H-purin-8-yl)-piperidin-3-yl]-carbaminate A solution of 250 mg (0.516 mmol) of compound V in 5 ml of dichloromethane and 0.5 ml of methanol is combined with 120.789 mg (0.7 mmol) of m-chloro-perbenzoic acid with stirring and cooling with ice. After 30 minutes the ice bath is removed and the mixture is stirred overnight at ambient temperature. 50 ml of methylene chloride are added and the mixture is extracted with 10% soda solution. The organic phase is washed with water, dried and concentrated by evaporation. 220 mg of the two title compounds are obtained in the ratio 45:55.

$R_f$ value: 0.1 (sulphoxide) and 0.8 (sulphone) (silica gel, ethyl acetate)

The following compounds were obtained analogously to Example VI:

(1)  tert.butyl[1-methyl-7-(3-methyl-but-2-enyl)-2-methylsulphinyl-6-oxo-6,7-dihydro-1H-purin-8-yl]-piperidin-3-yl)-carbaminate and tert.butyl[1-methyl-7-(3-methyl-but-2-enyl)-2-methylsulphonyl-6-oxo-6,7-dihydro-1H-purin-8-yl-]-piperidin-3-yl)-carbaminate prepared from compound V.2 and m-chloro-perbenzoic acid. The product obtained after a reaction time of 80 minutes is the sulphoxide, which contains a maximum of 10% sulphone.

$R_f$ value: 0.5 (silica gel, methylene chloride/methanol=10:1)

(2)  tert.butyl[1-(7-benzyl-2-methanesulphonyl-1-methyl-6-oxo-6,7-dihydro-1H-purin-8-yl)-piperidin-3-yl]-carbaminate prepared from compound V.

$R_f$ value: 0.75 (silica gel, ethyl acetate) Mass spectrum (ESI$^+$): m/z=517 [M+H]$^+$

EXAMPLE VII

Tert.butyl[1-(7-benzyl-2-benzylamino-1-methyl-6-oxo-6,7-dihydro-1H-purin-8-yl)-piperidin-3-yl]-carbaminate 258.312 mg of the mixture obtained in Example VI and 214.313 mg of benzylamine are stirred for 16 hours at ambient temperature. The mixture is triturated with 20 ml of diisopropylether, the precipitate is suction filtered, dissolved in a little methylene chloride and crystallised with diisopropylether. 250 mg of the title compound are obtained.

$R_f$ value: 0.55 (silica gel, ethyl acetate)

The following compounds were prepared analogously to Example VII:

(1)  tert.butyl[1-(7-benzyl-2-[4-fluoro-benzyl]amino-1-methyl-6-oxo-6,7-dihydro-1H-purin-8-yl)-piperidin-3-yl]-carbaminate prepared from Example VI and 4-fluoro-benzylamine $R_f$ value: 0.49 (silica gel, ethyl acetate)

(2)  tert.butyl[1-(7-benzyl-1-methyl-2-(2-phenylethyl)amino-6-oxo-6,7-dihydro-1H-purin-8-yl)-piperidin-3-yl]-carbaminate prepared from Example VI and 2-(2-phenylethyl)amine.

$R_f$ value: 0.5 (silica gel, ethyl acetate)

(3)  tert.butyl[1-(7-benzyl-2-isopropylamino-1-methyl-6-oxo-6,7-dihydro-1H-purin-8-yl)-piperidin-3-yl-]-carbaminate prepared from Example VI and isopropylamine.

$R_f$ value: 0.6 (silica gel, methylene chloride/methanol=9:1)

(4)  tert.butyl[1-(7-benzyl-1-methyl-2-methylamino-6-oxo-6,7-dihydro-1H-purin-8-yl)-piperidin-3-yl]-carbaminate prepared from Example VI and methylamine gas.

$R_f$ value: 0.27 (silica gel, methylene chloride/methanol=19:1)

(5)  tert.butyl[1-(7-benzyl-2-cyclohexylamino-1-methyl-6-oxo-6,7-dihydro-1H-purin-8-yl)-piperidin-3-yl]-carbaminate prepared from Example VI and cyclohexylamine $R_f$ value: 0.65 (silica gel, methylene chloride/methanol=9:1)

(6)  tert.butyl[1-(7-benzyl-2-cyclohexylmethylamino-1-methyl-6-oxo-6,7-dihydro-1H-purin-8-yl)-piperidin-3-yl]-carbaminate prepared from Example VI and cyclohexylmethylamine.

$R_f$ value: 0.54 (silica gel, ethyl acetate)

(7) tert.butyl[1-(7-benzyl-1-methyl-2-piperidino-6-oxo-6,7-dihydro-1H-purin-8-yl)-piperidin-3-yl]-carbaminate prepared from Example VI and piperidine.

$R_f$ value: 0.45 (silica gel, methylene chloride/methanol=20:1)

(8)  tert.butyl[1-(7-benzyl-2-dimethylamino-1-methyl-6-oxo-6,7-dihydro-1H-purin-8-yl)-piperidin-3-yl]-carbaminate prepared from Example VI and dimethylamine $R_f$ value: 0.65 (silica gel, methylene chloride/methanol=9:1)

(9)  tert.butyl[1-(2-amino-7-benzyl-1-methyl-6-oxo-6,7-dihydro-1H-purin-8-yl)-piperidin-3-yl]-carbaminate prepared from Example VI and ammonia gas.

$R_f$ value: 0.4 (silica gel, methylene chloride/methanol=10:1)

(10) tert.butyl[1-(2-benzylamino-1-methyl-7-[3-methylbut-2-enyl]-6-oxo-6,7-dihydro-1H-purin-8-yl)-piperidino-3-yl]-carbaminate
prepared from Example VI. 1 and benzylamine
$R_f$ value: 0.6 (silica gel, ethyl acetate)

EXAMPLE VIII

Tert.butyl[1-(7-benzyl-1-methyl-2-methyl-6-oxo-6,7-dihydro-1H-purin-8-yl)-piperidin-3-yl]-carbaminate A solution of 258.32 mg of Example VI in 3 ml of THF is combined with 0.2 ml of a 3-molar solution of methylmagnesium bromide in ether and the mixture is stirred for 48 hours at ambient temperature. 50 ml of ether were added and the mixture was extracted with water at pH 4. The organic phase was dried and concentrated by evaporation. The product obtained was purified through a silica gel column. 55 mg of the title compound are obtained.
$R_f$ value: 0.55 (silica gel, methylene chloride/methanol=10:1)
The following compound was obtained analogously to Example VIII:
(1) tert.butyl[1-(1-methyl-7-[3-methyl-but-2-enyl]-2-[2-phenylethyl]-6-oxo-6,7-dihydro-1H-purin-8-yl)-piperidin-3-yl]-carbaminate
prepared from Example VI.1 and (2-phenylethyl)magnesium bromide.
$R_f$ value: 0.5 (silica gel; methylene chloride/methanol=10:1)

EXAMPLE IX

Tert.butyl{1-[7-benzyl-1-methyl-6-oxo-2-(2-oxo-2-phenyl-ethyl)-6,7-dihydro-1H-purin-8-yl]-piperidin-3-yl}-carbaminate A solution of 132 mg of acetophenone in 1 ml of tetrahydrofuran is added dropwise at 0° C. to a solution of 0.63 ml of n-butyllithium (1.6 M in n-hexane) and 119 mg diisopropylamine in 2 ml of tetrahydrofuran. After 15 minutes a solution of 500 mg of tert.butyl[1-(7-benzyl-2-methanesulphonyl-1-methyl-6-oxo-6,7-dihydro-1H-purin-8-yl)-piperidin-3-yl]-carbaminate in 2 ml of tetrahydrofuran is added dropwise. Then the cooling bath is removed and the reaction mixture is stirred overnight at ambient temperature. As the thin layer chromatograph shows that there is still some starting material present, a further 0.94 ml of n-butyllithium (1.6 M in n-hexane) are added. After another 24 hours the reaction solution is diluted with 50 ml of water, adjusted to pH 6 with 2 N hydrochloric acid and extracted with ethyl acetate. The combined organic phases are washed with water, dried over magnesium sulphate and evaporated down. The crude product is purified by chromatography over a silica gel column with methylene chloride as eluant. 54 mg of the title compound are obtained.
$R_f$ value: 0.55 (aluminium oxide, methylene chloride)
Mass spectrum (ESI$^+$): m/z=557 [M+H]$^+$

EXAMPLE X

Tert.butyl[1-(7-benzyl-2-cyano-1-methyl-6-oxo-6,7-dihydro-1H-purin-8-yl)-piperidin-3-yl]-carbaminate 268 mg of tetrabutylammonium cyanide are added to 258 mg of tert.butyl[1-(7-benzyl-2-methanesulphonyl-1-methyl-6-oxo-6,7-dihydro-1H-purin-8-yl)-piperidin-3-yl]-carbaminate in 1 ml of methylene chloride and the reaction mixture is stirred for two days at ambient temperature. The reaction solution is chromatographed through a silica gel column with methylene chloride/methanol (97:3 to 90: 1) as eluant. The product thus obtained is crystallised from diisopropylether. 126 mg of the title compound are obtained.
$R_f$ value: 0.75 (silica gel, methylene chloride/methanol=10:1) Mass spectrum (ESI$^+$): m/z=464 [M+H]$^+$

EXAMPLE XI

Tert.butyl{1-[1-benzyl-2-methyl-7-(3-methyl-but-2-enyl)-6-oxo-6,7-dihydro-1H-purin-8-yl]-piperidin-3-yl}-carbaminate A mixture of 105 mg of tert.butyl{1-[5-methyl-i-(3-methyl-but-2-enyl)-7-oxo-1,7-dihydro-imidazo[4,5-d][1,3]oxazin-2-yl]-piperidin-3-yl}-carbaminate and 40 µl benzylamine in 1.5 ml of methylene chloride is stirred for two days at 40° C. Then 57 µl triethylamine and 37 µl phosphorus oxychloride are added and the reaction mixture is stirred for a further six hours at 40° C. For working up the reaction mixture is combined with aqueous potassium carbonate solution and extracted with ethyl acetate. The combined organic phases are dried over magnesium sulphate and evaporated down. The crude product is purified by chromatography over a silica gel column with methylene chloride/methanol (1:0 to 20:1) as eluant. 30 mg of the title compound are obtained.
Mass spectrum (ESI$^+$): m/z=507 [M+H]$^+$
The following is obtained analogously to Example XI:
(1) tert.butyl(1-{1-[(naphthalen-1-yl)methyl]-2-methyl-7-(3-methyl-but-2-enyl)-6-oxo-6,7-dihydro-1H-purin-8-yl}-piperidin-3-yl)-carbaminate
prepared from Example XII and 1-aminomethyl-naphthalene.
Mass spectrum (ESI$^+$): m/z=557 [M+H]$^+$

EXAMPLE XII

Tert.butyl{1-[5-methyl-1-(3-methyl-but-2-enyl)-7-oxo-1,7-dihydro-imidazo[4,5-d][1,3]oxazin-2-yl]-piperidin-3-yl}-carbaminate A mixture of 1.0 g of ethyl 5-acetylamino-2-(3-tert.-butyloxycarbonylamino-piperidin-1-yl)-3-(3-methyl-but-2-enyl)-3H-imidazol-4-carboxylate, 566 mg of triphenylphosphine and 0.97 ml of triethylamine in 16 ml of toluene is heated to 80° C. and combined with a solution of 702 mg of 1,2-dibromo-tetrachloroethane in 8 ml of toluene. The reaction mixture is stirred for four hours at 80° C., then the precipitate formed is filtered off and washed with toluene. The filtrate is evaporated down in vacuo and chromatographed through a silica gel column with cyclohexane/ethyl acetate as eluant. 804 mg of the title compound are obtained.
Mass spectrum (ESI$^+$): m/z=418 [M+H]$^+$
The following compound is obtained from Example XIII.1 under the same reaction conditions:
(1) ethyl2-(3-tert.-butyloxycarbonylamino-piperidin-1-yl)-5-isocyano-3-(3-methyl-but-2-enyl)-3H-imidazol-4-carboxylate
Mass spectrum (ESI$^+$): m/z=432 [M+H]$^+$

EXAMPLE XIII

Ethyl 5-acetylamino-2-(3-tert.-butyloxycarbonylamino-piperidin-1-yl)-3-(3-methyl-but-2-enyl)-3H-imidazol-4-carboxylate prepared from Example I.1 by reaction with acetylchloride in the presence of pyridine in methylene chloride.

Mass spectrum (ESI$^+$): m/z=464 [M+H]$^+$

The following compound is obtained analogously to Example XIII:
(1) ethyl2-(3-tert.-butyloxycarbonylamino-piperidin-1-yl)-5-formylamino-3-(3-methyl-but-2-enyl)-3H-imidazol-4-carboxylate prepared from Example I.1 by reaction with formic acid and acetic anhydride in the presence of pyridine in methylene chloride.

Mass spectrum (ESI$^+$): m/z=450 [M+H]$^+$

EXAMPLE XIV

Tert.butyl(1-{1-[(naphthalen-1-yl)methyl]-7-(3-methyl-but-2-enyl)-6-oxo-6,7-dihydro-1H-purin-8-yl}-piperidin-3-yl)-carbaminate 210 mg of 1-aminomethyl-naphthalene and 30 mg of copper(I)oxide are added to 295 mg of ethyl 2-(3-tert.-butyloxycarbonylamino-piperidin-1-yl)-5-isocyano-3-(3-methyl-but-2-enyl)-3H-imidazol-4-carboxylate in 7 ml of toluene. The reaction mixture is stirred for 10 hours at 120° C. After cooling to ambient temperature it is diluted with ethyl acetate and filtered through Celite. The filtrate is combined with water and extracted with ethyl acetate. The combined extracts are dried over magnesium sulphate and evaporated down. The crude product is chromatographed through a silica gel column with methylene chloride/methanol (1:0 to 10:1) as eluant. 306 mg of the title compound are obtained, contaminated with ethyl 5-amino-2-(3-tert.-butoxycarbonylamino-piperidin-1-yl)-3-(3-methyl-but-2-enyl)-3H-imidazol-4-carboxylate.

Mass spectrum (ESI$^+$): m/z=543 [M+H]$^+$

The following compound is obtained analogously to Example XIV:
(1) tert.butyl(1-{1-[(4-methoxy-naphthalen-1-yl)methyl]-7-(3-methyl-but-2-enyl)-6-oxo-6,7-dihydro-1H-purin-8-yl}-piperidin'-3-yl)-carbaminate prepared from Example XII.1 and 1-aminomethyl-4-methoxy-naphthalene.

$R_f$ value: 0.17 (silica gel, cyclohexane/ethyl acetate=1:9)
Mass spectrum (ESI$^+$): m/z=573 [M+H]$^+$ Examples of the preparation of the end products:

EXAMPLE 1

8-(3-amino-piperidin-1-yl)-7-benzyl-2-benzylamino-1-methyl-1,7-dihydro-purin-6-one A solution of 200 mg of Example VII in 2 ml of dichloromethane is combined with 3 ml of trifluoroacetic acid with stirring and cooling with ice. After 30 minutes the ice bath is removed and stirring is continued for 2 hours. The solvent is evaporated at low temperature, the residue is triturated with ether, suction filtered and dried in vacuo. 150 mg (73.1% of theory) of the trifluoroacetate of the title compound are obtained.

$R_f$ value: 0.45 (aluminium oxide, methylene chloride/methanol=20:1) $^1$H-NMR spectrum (400 MHz, DMSO-d$_6$): 1.5 (m,2H), 1,7 (m,1H), 1.95 (m,1H), 2.8 (m,1H), 3.0 (m,1H), 3.15 (d,1H), 3.4 (s+m,4H), 3.5(d,1H), 4.55 (d,2H), 5.35(s, 2H), 7.1-7.5 (m,12H), 8.0 (s,3H), 8.1-8.3 (m,1H)

The following compounds were obtained analogously to Example 1:
(1) 8-(3-amino-piperidin-1-yl)-7-benzyl-2-(4-fluoro-benzylamino)-1-methyl-1,7-dihydro-purin-6-one trifluoroacetate
    prepared from Example VII.1 and trifluoroacetic acid
    $R_f$ value: 0.69 (aluminium oxide, methylene chloride/methanol=9:1)
(2) 8-(3-amino-piperidin-1-yl)-7-benzyl-1-methyl-2-[(2-phenylethyl)amino]-1,7-dihydro-purin-6-one trifluoroacetate
    prepared from Example VII.2 and trifluoroacetic acid.
    $R_f$ value: 0.75 (aluminium oxide, methylene chloride/methanol=9:1)
(3) 8-(3-amino-piperidin-1-yl)-7-benzyl-2-isopropylamino-1-methyl-1,7-dihydro-purin-6-one trifluoroacetate
    prepared from Example VII.3 and trifluoroacetic acid.
    $R_f$ value: 0.68 (aluminium oxide, methylene chloride/methanol=9:1)
(4) 8-(3-amino-piperidin-1-yl)-7-benzyl-1-methyl-2-methylamino-1,7-dihydro-purin-6-one trifluoroacetate
    prepared from Example VII.4 and trifluoroacetic acid.
    $R_f$ value: 0.26 (aluminium oxide, methylene chloride/methanol=9:1)
(5) 8-(3-amino-piperidin-1-yl)-7-benzyl-2-cyclohexylamino-1-methyl-1,7-dihydro-purin-6-one trifluoroacetate
    prepared from Example VII.5 and trifluoroacetic acid.
    $R_f$ value: 0.65 (aluminium oxide, methylene chloride/methanol=9:1)
(6) 8-(3-amino-piperidin-1-yl)-7-benzyl-2-cyclohexylmethylamino-1-methyl-1,7-dihydro-purin-6-one trifluoroacetate
    prepared from Example VII.6 and trifluoroacetic acid.
    $R_f$ value: 0.69 (aluminium oxide, methylene chloride/methanol=9:1)
(7) 8-(3-amino-piperidin-1-yl)-7-benzyl-1-methyl-2-(piperidin-1-yl)-1,7-dihydro-purin-6-one hydrochloride
    prepared from Example VII.7 and hydrogen chloride in dioxane.
    $R_f$ value: 0.3-0.5 (aluminium oxide, methylene chloride/methanol=20:1)
(8) 8-(3-amino-piperidin-1-yl)-7-benzyl-2-dimethylamino-1-methyl-1,7-dihydro-purin-6-one trifluoroacetate
    prepared from Example VII.8 and trifluoroacetic acid.
    $R_f$ value: 0.69 (aluminium oxide, methylene chloride/methanol=9:1)
(9) 2-amino-8-(3-amino-piperidin-1-yl)-7-benzyl-1-methyl-1,7-dihydro-purin-6-one trifluoroacetate
    prepared from Example VII.9 and trifluoroacetic acid.
    $R_f$ value: 0.2 (aluminium oxide, methylene chloride/methanol=10:1)
(10) 8-(3-amino-piperidin-1-yl)-2-benzylamino-1-methyl-7-(3-methyl-but-2-en-1-yl)-1,7-dihydro-purin-6-one trifluoroacetate
    prepared from Example VII.10 and trifluoroacetic acid.
    $R_f$ value: 0.55 (aluminium oxide, methylene chloride/methanol=10:1)
(11) 8-(3-amino-piperidin-1-yl)-7-benzyl-1-methyl-2-methyl-1,7-dihydro-purin-6-one trifluoroacetate
    prepared from Example VIII and trifluoroacetic acid.
    $R_f$ value: 0.6 (aluminium oxide, methylene chloride/methanol=10:1)

(12) 8-(3-amino-piperidin-1-yl)-1-methyl-7-(3-methyl-but-2-en-1-yl)-2-(2-phenylethyl)-1,7-dihydro-purin-6-one trifluoroacetate
prepared from Example VIII.1 and trifluoroacetic acid.
$R_f$ value: 0.4 (aluminium oxide, methylene chloride/methanol=20:1)

(13) 8-(3-amino-piperidin-1-yl)-7-benzyl-1-methyl-1,7-dihydro-purin-6-one hydrochloride
prepared from Example III and hydrogen chloride in dioxane.
$R_f$ value: 0.2-0.5 (aluminium oxide, methylene chloride/methanol=20:1)

(14) 8-(3-amino-piperidin-1-yl)-7-benzyl-2-methylsulphanyl-1,7-dihydro-purin-6-one hydrochloride
prepared from Example IV and hydrogen chloride in dioxane.
$R_f$ value: 0.5 (aluminium oxide, methylene chloride/methanol=10:1)

(15) 8-(3-amino-piperidin-1-yl)-7-benzyl-2-benzylsulphanyl-1,7-dihydro-purin-6-one trifluoroacetate
prepared from Example IV.1 and trifluoroacetic acid.
$R_f$ value: 0.5-0.6 (aluminium oxide, methylene chloride/methanol=10:1)

(16) 8-(3-amino-piperidin-1-yl)-7-benzyl-1-methyl-2-methylsulphanyl-1,7-dihydro-purin-6-one hydrochloride
prepared from Example V and hydrogen chloride in dioxane.
$R_f$ value: 0.5 (aluminium oxide, methylene chloride/methanol=20:1)

(17) 8-(3-amino-piperidin-1-yl)-7-benzyl-2-methylsulphanyl-1-(2-phenyl-2-oxo-ethyl)-1,7-dihydro-purin-6-one hydrochloride
prepared from Example V.1 and hydrogen chloride in dioxane.
$R_f$ value: 0.4 (aluminium oxide, methylene chloride/methanol=20:1)

(18) 8-(3-amino-piperidin-1-yl)-1-benzyl-7-benzyl-2-methylsulphanyl-1,7-dihydro-purin-6-one hydrochloride
prepared from Example V.3 and hydrogen chloride.
$R_f$ value: 0.4-0.5 (aluminium oxide, methylene chloride/methanol=20:1)

(19) 8-(3-amino-piperidin-1-yl)-7-benzyl-2-methylsulphanyl-1-(2-phenylethyl)-1,7-dihydro-purin-6-one hydrochloride
prepared from Example V.4 and hydrogen chloride.
$R_f$ value: 0.4 (aluminium oxide, methylene chloride/methanol=20:1)

(20) 8-(3-amino-piperidin-1-yl)-7-benzyl-2-benzylsulphanyl-1-methyl-1,7-dihydro-purin-6-one
prepared from Example V.5 and hydrogen chloride.
$R_f$ value: 0.5 (aluminium oxide, methylene chloride/methanol=20:1)

(21) 8-(3-amino-piperidin-1-yl)-7-benzyl-2-[(2-phenylethyl)sulphanyl]-1-methyl-1,7-dihydro-purin-6-one
prepared from Example V.6 and hydrogen chloride.
$R_f$ value: 0.55 (aluminium oxide, methylene chloride/methanol=20:1)

(22) 8-(3-amino-piperidin-1-yl)-7-benzyl-1-(2-oxo-2-phenyl-ethyl)-1,7-dihydro-purin-6-one trifluoroacetate
prepared from Example III.1 and trifluoroacetic acid.
$R_f$ value: 0.65 (aluminium oxide, methylene chloride/methanol=10:1)

(23) 8-(3-amino-piperidin-1-yl)-7-benzyl-1-methyl-2-(2-oxo-2-phenyl-ethyl)-1,7-dihydro-purin-6-one
prepared from Example IX and trifluoroacetic acid.
$R_f$ value: 0.20 (silica gel, methylene chloride/methanol=10:1) Mass spectrum (ESI$^+$): m/z=457 [M+H]$^+$

(24) 8-(3-amino-piperidin-1-yl)-7-benzyl-2-cyano-1-methyl-1,7-dihydro-purin-6-one trifluoroacetate
prepared from Example X and trifluoroacetic acid.
$R_f$ value: 0.50 (aluminium oxide, methylene chloride/methanol=20:1) Mass spectrum (ESI$^+$): m/z=364 [M+H]$^+$

(25) 8-(3-amino-piperidin-1-yl)-1-benzyl-2-methyl-7-(3-methyl-but-2-en-1-yl)-1,7-dihydro-purin-6-one
prepared from Example XI and trifluoroacetic acid.
Mass spectrum (ESI$^+$): m/z=407 [M+H]$^+$

(26) 8-(3-amino-piperidin-1-yl)-2-methyl-7-(3-methyl-but-2-en-1-yl)-1-[(naphthalen-1-yl)methyl]-1,7-dihydro-purin-6-one
prepared from Example XI.1 and trifluoroacetic acid.
Mass spectrum (ESI$^+$): m/z=457 [M+H]$^+$

(27) 8-(3-amino-piperidin-1-yl)-7-(3-methyl-but-2-en-1-yl)-1-[(naphthalen-1-yl)methyl]-1,7-dihydro-purin-6-one
prepared from Example XIV and trifluoroacetic acid.
Mass spectrum (ESI$^+$): m/z=443 [M+H]$^+$

(28) 8-(3-amino-piperidin-1-yl)-7-(3-methyl-but-2-en-1-yl)-1-[(4-methoxy-naphthalen-1-yl)methyl]-1,7-dihydro-purin-6-one
prepared from Example XV.1 and trifluoroacetic acid.
Mass spectrum (ESI$^+$): m/z=473 [M+H]$^+$ The following compounds may also be obtained analogously to the preceding Examples and other methods known from the literature:

(1) 8-(3-amino-piperidin-1-yl)-7-benzyl-1-ethyl-2-benzylamino-1,7-dihydro-purin-6-one
(2) 8-(3-amino-piperidin-1-yl)-7-benzyl-1-propyl-2-benzylamino-1,7-dihydro-purin-6-one
(3) 8-(3-amino-piperidin-1-yl)-7-benzyl-1-isopropyl-2-benzylamino-1,7-dihydro-purin-6-one
(4) 8-(3-amino-piperidin-1-yl)-7-benzyl-1-butyl-2-benzylamino-1,7-dihydro-purin-6-one
(5) 8-(3-amino-piperidin-1-yl)-7-benzyl-1-(2-methyl-propyl)-2-benzylamino-1,7-dihydro-purin-6-one
(6) 8-(3-amino-piperidin-1-yl)-7-benzyl-1-pentyl-2-benzylamino-1,7-dihydro-purin-6-one
(7) 8-(3-amino-piperidin-1-yl)-7-benzyl-1-(3-methyl-butyl)-2-benzylamino-1,7-dihydro-purin-6-one
(8) 8-(3-amino-piperidin-1-yl)-7-benzyl-1-hexyl-2-benzylamino-1,7-dihydro-purin-6-one
(9) 8-(3-amino-piperidin-1-yl)-7-benzyl-1-(4-methyl-pentyl)-2-benzylamino-1,7-dihydro-purin-6-one
(10) 8-(3-amino-piperidin-1-yl)-7-benzyl-1-allyl-2-benzylamino-1,7-dihydro-purin-6-one
(11) 8-(3-amino-piperidin-1-yl)-7-benzyl-1-(3-methyl-but-2-en-1-yl)-2-benzylamino-1,7-dihydro-purin-6-one
(12) 8-(3-amino-piperidin-1-yl)-7-benzyl-1-(prop-2-in-1-yl)-2-benzylamino-1,7-dihydro-purin-6-one
(13) 8-(3-amino-piperidin-1-yl)-7-benzyl-1-cyclopropylmethyl-2-benzylamino-1,7-dihydro-purin-6-one
(14) 8-(3-amino-piperidin-1-yl)-7-benzyl-1-cyclohexylmethyl-2-benzylamino-1,7-dihydro-purin-6-one
(15) 8-(3-amino-piperidin-1-yl)-7-benzyl-1-(4-chlorobenzyl)-2-benzylamino-1,7-dihydro-purin-6-one
(16) 8-(3-amino-piperidin-1-yl)-7-benzyl-1-(2-fluorobenzyl)-2-benzylaamino-1,7-dihydro-purin-6-one
(17) 8-(3-amino-piperidin-1-yl)-7-benzyl-1-(4-methylbenzyl)-2-benzylamino-1,7-dihydro-purin-6-one
(18) 8-(3-amino-piperidin-1-yl)-7-benzyl-1-(2,4-dimethylbenzyl)-2-benzylamino-1,7-dihydro-purin-6-one
(19) 8-(3-amino-piperidin-1-yl)-7-benzyl-1-(2,4-dimethoxybenzyl)-2-benzylamino-1,7-dihydro-purin-6-one
(20) 8-(3-amino-piperidin-1-yl)-7-benzyl-1-(3-trifluoromethyl-benzyl)-2-benzylamino-1,7-dihydro-purin-6-one

(21) 8-(3-amino-piperidin-1-yl)-7-benzyl-1-(3-trifluoromethoxy-benzyl)-2-benzylamino-1,7-dihydro-purin-6-one
(22) 8-(3-amino-piperidin-1-yl)-7-benzyl-1-(3-difluoromethoxy-benzyl)-2-benzylamino-1,7-dihydro-purin-6-one
(23) 8-(3-amino-piperidin-1-yl)-7-benzyl-1-(furan-2-yl-methyl)-2-benzylamino-1,7-dihydro-purin-6-one
(24) 8-(3-amino-piperidin-1-yl)-7-benzyl-1-(thien-2-yl-methyl)-2-benzylamino-1,7-dihydro-purin-6-one
(25) 8-(3-amino-piperidin-1-yl)-7-benzyl-1-(3-methyl-isoxazol-5-yl-methyl)-2-benzylamino-1,7-dihydro-purin-6-one
(26) 8-(3-amino-piperidin-1-yl)-7-benzyl-1-(pyridin-4-yl-methyl)-2-benzylamino-1,7-dihydro-purin-6-one
(27) 8-(3-amino-piperidin-1-yl)-7-benzyl-1-[2-(4-methyl-phenyl)-2-oxo-ethyl]-2-benzylamino-1,7-dihydro-purin-6-one
(28) 8-(3-amino-piperidin-1-yl)-7-benzyl-1-[2-(2,4-dichloro-phenyl)-2-oxo-ethyl]-2-benzylamino-1,7-dihydro-purin-6-one
(29) 8-(3-amino-piperidin-1-yl)-7-benzyl-1-[2-(4-methoxyphenyl)-2-oxo-ethyl]-2-benzylamino-1,7-dihydro-purin-6-one
(30) 8-(3-amino-piperidin-1-yl)-7-benzyl-1-[2-(4-trifluoromethyl-phenyl)-2-oxo-ethyl]-2-benzylamino-1,7-dihydro-purin-6-one
(31) 8-(3-amino-piperidin-1-yl)-7-benzyl-1-[2-(4-trifluoromethoxy-phenyl)-2-oxo-ethyl]-2-benzylamino-1,7-dihydro-purin-6-one
(32) 8-(3-amino-piperidin-1-yl)-7-benzyl-1-[2-(4-difluoromethoxy-phenyl)-2-oxo-ethyl]-2-benzylamino-1,7-dihydro-purin-6-one
(33) 8-(3-amino-piperidin-1-yl)-7-benzyl-1-[2-(furan-2-yl)-2-oxo-ethyl]-2-benzylamino-1,7-dihydro-purin-6-one
(34) 8-(3-amino-piperidin-1-yl)-7-benzyl-1-[2-(thien-2-yl)-2-oxo-ethyl]-2-benzylamino-1,7-dihydro-purin-6-one
(35) 8-(3-amino-piperidin-1-yl)-7-benzyl-1-[2-(pyridin-3-yl)-2-oxo-ethyl]-2-benzylamino-1,7-dihydro-purin-6-one
(36) 8-(3-amino-piperidin-1-yl)-7-benzyl-1-(2-oxopropyl)-2-benzylamino-1,7-dihydro-purin-6-one
(37) 8-(3-amino-piperidin-1-yl)-7-benzyl-1-(2-cyclohexyl-2-oxo-ethyl)-2-benzylamino-1,7-dihydro-purin-6-one
(38) 8-(3-amino-piperidin-1-yl)-7-benzyl-1-ethyl-2-(2-phenylethyl)-1,7-dihydro-purin-6-one
(39) 8-(3-amino-piperidin-1-yl)-7-benzyl-1-propyl-2-(2-phenylethyl)-1,7-dihydro-purin-6-one
(40) 8-(3-amino-piperidin-1-yl)-7-benzyl-1-isopropyl-2-(2-phenylethyl)-1,7-dihydro-purin-6-one
(41) 8-(3-amino-piperidin-1-yl)-7-benzyl-1-butyl-2-(2-phenylethyl)-1,7-dihydro-purin-6-one
(42) 8-(3-amino-piperidin-1-yl)-7-benzyl-1-(2-methyl-propyl)-2-(2-phenylethyl)-1,7-dihydro-purin-6-one
(43) 8-(3-amino-piperidin-1-yl)-7-benzyl-1-pentyl-2-(2-phenylethyl)-1,7-dihydro-purin-6-one
(44) 8-(3-amino-piperidin-1-yl)-7-benzyl-1-(3-methyl-butyl)-2-(2-phenylethyl)-1,7-dihydro-purin-6-one
(45) 8-(3-amino-piperidin-1-yl)-7-benzyl-1-hexyl-2-(2-phenylethyl)-1,7-dihydro-purin-6-one
(46) 8-(3-amino-piperidin-1-yl)-7-benzyl-1-(4-methyl-pentyl)-2-(2-phenylethyl)-1,7-dihydro-purin-6-one
(47) 8-(3-amino-piperidin-1-yl)-7-benzyl-1-allyl-2-(2-phenylethyl)-1,7-dihydro-purin-6-one
(48) 8-(3-amino-piperidin-1-yl)-7-benzyl-1-(3-methyl-but-2-en-1-yl)-2-(2-phenylethyl)-1,7-dihydro-purin-6-one
(49) 8-(3-amino-piperidin-1-yl)-7-benzyl-1-(prop-2-in-1-yl)-2-(2-phenylethyl)-1,7-dihydro-purin-6-one
(50) 8-(3-amino-piperidin-1-yl)-7-benzyl-1-cyclopropylmethyl-2-(2-phenylethyl)-1,7-dihydro-purin-6-one
(51) 8-(3-amino-piperidin-1-yl)-7-benzyl-1-cyclohexylmethyl-2-(2-phenylethyl)-1,7-dihydro-purin-6-one
(52) 8-(3-amino-piperidin-1-yl)-7-benzyl-1-(4-chlorobenzyl)-2-(2-phenylethyl)-1,7-dihydro-purin-6-one
(53) 8-(3-amino-piperidin-1-yl)-7-benzyl-1-(2-fluorobenzyl)-2-(2-phenylethyl)-1,7-dihydro-purin-6-one
(54) 8-(3-amino-piperidin-1-yl)-7-benzyl-1-(4-methylbenzyl)-2-(2-phenylethyl)-1,7-dihydro-purin-6-one
(55) 8-(3-amino-piperidin-1-yl)-7-benzyl-1-(2,4-dimethyl-benzyl)-2-(2-phenylethyl)-1,7-dihydro-purin-6-one
(56) 8-(3-amino-piperidin-1-yl)-7-benzyl-1-(2,4-dimethoxybenzyl)-2-(2-phenylethyl)-1,7-dihydro-purin-6-one
(57) 8-(3-amino-piperidin-1-yl)-7-benzyl-1-(3-trifluoromethyl-benzyl)-2-(2-phenylethyl)-1,7-dihydro-purin-6-one
(58) 8-(3-amino-piperidin-1-yl)-7-benzyl-1-(3-trifluoromethoxy-benzyl)-2-(2-phenyl-ethyl)-1,7-dihydro-purin-6-one
(59) 8-(3-amino-piperidin-1-yl)-7-benzyl-1-(3-difluoromethoxy-benzyl)-2-(2-phenyl-ethyl)-1,7-dihydro-purin-6-one
(60) 8-(3-amino-piperidin-1-yl)-7-benzyl-1-(furan-2-yl-methyl)-2-(2-phenylethyl)-7-dihydro-purin-6-one
(61) 8-(3-amino-piperidin-1-yl)-7-benzyl-1-(thien-2-yl-methyl)-2-(2-phenylethyl)-1,7-dihydro-purin-6-one
(62) 8-(3-amino-piperidin-1-yl)-7-benzyl-1-(3-methyl-isoxazol-5-yl-methyl)-2-(2-phenylethyl)-1,7-dihydro-purin-6-one
(63) 8-(3-amino-piperidin-1-yl)-7-benzyl-1-(pyridin-4-yl-methyl)-2-(2-phenylethyl)-1,7-dihydro-purin-6-one
(64) 8-(3-amino-piperidin-1-yl)-7-benzyl-1-[2-(4-methyl-phenyl)-2-oxo-ethyl]-2-(2-phenylethyl)-1,7-dihydro-purin-6-one
(65) 8-(3-amino-piperidin-1-yl)-7-benzyl-1-[2-(2,4-dichloro-phenyl)-2-oxo-ethyl]-2-(2-phenylethyl)-1,7-dihydro-purin-6-one
(66) 8-(3-amino-piperidin-1-yl)-7-benzyl-1-[2-(4-methoxyphenyl)-2-oxo-ethyl]-2-(2-phenylethyl)-1,7-dihydro-purin-6-one
(67) 8-(3-amino-piperidin-1-yl)-7-benzyl-1-[2-(4-trifluoromethyl-phenyl)-2-oxo-ethyl]-2-(2-phenylethyl)-1,7-dihydro-purin-6-one
(68) 8-(3-amino-piperidin-1-yl)-7-benzyl-1-[2-(4-trifluoromethoxy-phenyl)-2-oxo-ethyl]-2-(2-phenylethyl)-1,7-dihydro-purin-6-one
(69) 8-(3-amino-piperidin-1-yl)-7-benzyl-1-[2-(4-difluoromethoxy-phenyl)-2-oxo-ethyl]-2-(2-phenylethyl)-1,7-dihydro-purin-6-one
(70) 8-(3-amino-piperidin-1-yl)-7-benzyl-1-[2-(furan-2-yl)-2-oxo-ethyl]-2-(2-phenyl-ethyl)-1,7-dihydro-purin-6-one
(71) 8-(3-amino-piperidin-1-yl)-7-benzyl-1-[2-(thien-2-yl)-2-oxo-ethyl]-2-(2-phenylethyl)-1,7-dihydro-purin-6-one
(72) 8-(3-amino-piperidin-1-yl)-7-benzyl-1-[2-(pyridin-3-yl)-2-oxo-ethyl]-2-(2-phenyl-ethyl)-1,7-dihydro-purin-6-one
(73) 8-(3-amino-piperidin-1-yl)-7-benzyl-1-(2-oxo-propyl)-2-(2-phenylethyl)-1,7-dihydro-purin-6-one
(74) 8-(3-amino-piperidin-1-yl)-7-benzyl-1-(2-cyclohexyl-2-oxo-ethyl)-2-(2-phenyl-ethyl)-1,7-dihydro-purin-6-one
(75) 8-(3-amino-piperidin-1-yl)-7-benzyl-1-methyl-2-ethylamino-1,7-dihydro-purin-6-one
(76) 8-(3-amino-piperidin-1-yl)-7-benzyl-1-methyl-2-propylamino-1,7-dihydro-purin-6-one
(77) 8-(3-amino-piperidin-1-yl)-7-benzyl-1-methyl-2-butylamino-1,7-dihydro-purin-6-one

(78) 8-(3-amino-piperidin-1-yl)-7-benzyl-1-methyl-2-(2-methyl-propylamino)-1,7-dihydro-purin-6-one
(79) 8-(3-amino-piperidin-1-yl)-7-benzyl-1-methyl-2-(N-ethyl-N-methyl-amino)-1,7-dihydro-purin-6-one
(80) 8-(3-amino-piperidin-1-yl)-7-benzyl-1-methyl-2-diethylamino-1,7-dihydro-purin-6-one
(81) 8-(3-amino-piperidin-1-yl)-7-benzyl-1-methyl-2-(N-methyl-N-propyl-amino)-1,7-dihydro-purin-6-one
(82) 8-(3-amino-piperidin-1-yl)-7-benzyl-1-methyl-2-(N-butyl-N-methyl-amino)-1,7-dihydro-purin-6-one
(83) 8-(3-amino-piperidin-1-yl)-7-benzyl-1-methyl-2-(2-hydroxyethyl-amino)-1,7-dihydro-purin-6-one
(84) 8-(3-amino-piperidin-1-yl)-7-benzyl-1-methyl-2-[N-methyl-N-(2-hydroxyethyl)-amino]-1,7-dihydro-purin-6-one
(85) 8-(3-amino-piperidin-1-yl)-7-benzyl-1-methyl-2-(2-methoxy-ethylamino)-1,7-dihydro-purin-6-one
(86) 8-(3-amino-piperidin-1-yl)-7-benzyl-1-methyl-2-(3-methoxy-propylamino)-1,7-dihydro-purin-6-one
(87) 8-(3-amino-piperidin-1-yl)-7-benzyl-1-methyl-2-[N-methyl-N-(2-methoxy-ethyl)-amino]-1,7-dihydro-purin-6-one
(88) 8-(3-amino-piperidin-1-yl)-7-benzyl-1-methyl-2-[(2-phenoxyethyl)-amino]-1,7-dihydro-purin-6-one
(89) 8-(3-amino-piperidin-1-yl)-7-benzyl-1-methyl-2-[(2-aminoethyl)-amino]-1,7-dihydro-purin-6-one
(90) 8-(3-amino-piperidin-1-yl)-7-benzyl-1-methyl-2-[(3-aminopropyl)-amino]-1,7-dihydro-purin-6-one
(91) 8-(3-amino-piperidin-1-yl)-7-benzyl-1-methyl-2-[(2-methylamino-ethyl)-amino]-1,7-dihydro-purin-6-one
(92) 8-(3-amino-piperidin-1-yl)-7-benzyl-1-methyl-2-[(3-dimethylamino-propyl)amino]-1,7-dihydro-purin-6-one
(93) 8-(3-amino-piperidin-1-yl)-7-benzyl-1-methyl-2-[(2-acetylamino-ethyl)amino]-1,7-dihydro-purin-6-one
(94) 8-(3-amino-piperidin-1-yl)-7-benzyl-1-methyl-2-[(2-benzoylamino-ethyl)amino]-1,7-dihydro-purin-6-one
(95) 8-(3-amino-piperidin-1-yl)-7-benzyl-1-methyl-2-[(2-ethoxycarbonylamino-ethyl)amino]-1,7-dihydro-purin-6-one
(96) 8-(3-amino-piperidin-1-yl)-7-benzyl-1-methyl-2-[(2-methylsulphanyl-ethyl)amino]-1,7-dihydro-purin-6-one
(97) 8-(3-amino-piperidin-1-yl)-7-benzyl-1-methyl-2-[(2-phenylsulphanyl-ethyl)amino]-1,7-dihydro-purin-6-one
(98) 8-(3-amino-piperidin-1-yl)-7-benzyl-1-methyl-2-[(2-cyano-ethyl)amino]-1,7-dihydro-purin-6-one
(99) 8-(3-amino-piperidin-1-yl)-7-benzyl-1-methyl-2-[(carboxymethyl)amino]-1,7-dihydro-purin-6-one
(100) 8-(3-amino-piperidin-1-yl)-7-benzyl-1-methyl-2-[(ethoxycarbonylmethyl)amino]-1,7-dihydro-purin-6-one
(101) 8-(3-amino-piperidin-1-yl)-7-benzyl-1-methyl-2-[(aminocarbonylmethyl)amino]-1,7-dihydro-purin-6-one
(102) 8-(3-amino-piperidin-1-yl)-7-benzyl-1-methyl-2-[(ethylaminocarbonylmethyl)-amino]-1,7-dihydro-purin-6-one
(103) 8-(3-amino-piperidin-1-yl)-7-benzyl-1-methyl-2-[(dimethylaminocarbonylmethyl)-amino]-1,7-dihydro-purin-6-one
(104) 8-(3-amino-piperidin-1-yl)-7-benzyl-1-methyl-2-[(pyrrolidin-1-yl-carbonylmethyl)-amino]-1,7-dihydro-purin-6-one
(105) 8-(3-amino-piperidin-1-yl)-7-benzyl-1-methyl-2-[(piperidin-1-yl-carbonyl-methyl)amino]-1,7-dihydro-purin-6-one
(106) 8-(3-amino-piperidin-1-yl)-7-benzyl-1-methyl-2-[(morpholin-4-ylcarbonylmethyl)amino]-1,7-dihydro-purin-6-one
(107) 8-(3-amino-piperidin-1-yl)-7-benzyl-1-methyl-2-[(cyclopentylmethyl)amino]-1,7-dihydro-purin-6-one
(108) 8-(3-amino-piperidin-1-yl)-7-benzyl-1-methyl-2-[(cyclobutylmethyl)amino]-1,7-dihydro-purin-6-one
(109) 8-(3-amino-piperidin-1-yl)-7-benzyl-1-methyl-2-[(cyclopropylmethyl)amino]-1,7-dihydro-purin-6-one
(110) 8-(3-amino-piperidin-1-yl)-7-benzyl-1-methyl-2-[(2-cyclohexyl-ethyl)amino]-1,7-dihydro-purin-6-one
(111) 8-(3-amino-piperidin-1-yl)-7-benzyl-1-methyl-2-[(3-cyclohexyl-propyl)amino]-1,7-dihydro-purin-6-one
(112) 8-(3-amino-piperidin-1-yl)-7-benzyl-1-methyl-2-(cyclobutylamino)-1,7-dihydro-purin-6-one
(113) 8-(3-amino-piperidin-1-yl)-7-benzyl-1-methyl-2-(cyclopentylamino)-1,7-dihydro-purin-6-one
(114) 8-(3-amino-piperidin-1-yl)-7-benzyl-1-methyl-2-(phenylamino)-1,7-dihydro-purin-6-one
(115) 8-(3-amino-piperidin-1-yl)-7-benzyl-1-methyl-2-(3,4-dichlorobenzyl-amino)-1,7-dihydro-purin-6-one
(116) 8-(3-amino-piperidin-1-yl)-7-benzyl-1-methyl-2-(4-methylbenzyl-amino)-1,7-dihydro-purin-6-one
(117) 8-(3-amino-piperidin-1-yl)-7-benzyl-1-methyl-2-(4-methoxybenzyl-amino)-1,7-dihydro-purin-6-one
(118) 8-(3-amino-piperidin-1-yl)-7-benzyl-1-methyl-2-(4-trifluoromethylbenzyl-amino)-1,7-dihydro-purin-6-one
(119) 8-(3-amino-piperidin-1-yl)-7-benzyl-1-methyl-2-(4-trifluoromethoxybenzyl-amino)-1,7-dihydro-purin-6-one
(120) 8-(3-amino-piperidin-1-yl)-7-benzyl-1-methyl-2-(4-difluoromethoxybenzyl-amino)-1,7-dihydro-purin-6-one
(121) 8-(3-amino-piperidin-1-yl)-7-benzyl-1-methyl-2-(3,4-methylenedioxybenzyl-amino)-1,7-dihydro-purin-6-one
(122) 8-(3-amino-piperidin-1-yl)-7-benzyl-1-methyl-2-[(furan-2-yl-methyl)amino]-1,7-dihydro-purin-6-one
(123) 8-(3-amino-piperidin-1-yl)-7-benzyl-1-methyl-2-[(thien-2-yl-methyl)amino]-1,7-dihydro-purin-6-one
(124) 8-(3-amino-piperidin-1-yl)-7-benzyl-1-methyl-2-[(pyridine-2-yl-methyl)amino]-1,7-dihydro-purin-6-one
(125) 8-(3-amino-piperidin-1-yl)-7-benzyl-1-methyl-2-[(4-methylthiazol-2-ylmethyl)-amino]-1,7-dihydro-purin-6-one
(126) 8-(3-amino-piperidin-1-yl)-7-benzyl-1-methyl-2-{[2-(pyridine-2-yl)ethyl]amino}-1,7-dihydro-purin-6-one
(127) 8-(3-amino-piperidin-1-yl)-7-benzyl-1-methyl-2-(pyrrolidin-1-yl)-1,7-dihydro-purin-6-one
(128) 8-(3-amino-piperidin-1-yl)-7-benzyl-1-methyl-2-(morpholin-4-yl)-1,7-dihydro-purin-6-one
(129) 8-(3-amino-piperidin-1-yl)-7-benzyl-1-methyl-2-(piperazin-1-yl)-1,7-dihydro-purin-6-one
(130) 8-(3-amino-piperidin-1-yl)-7-benzyl-1-methyl-2-(4-methyl-piperazin-1-yl)-1,7-dihydro-purin-6-one
(131) 8-(3-amino-piperidin-1-yl)-7-benzyl-1-methyl-2-ethyl-1,7-dihydro-purin-6-one
(132) 8-(3-amino-piperidin-1-yl)-7-benzyl-1-methyl-2-propyl-1,7-dihydro-purin-6-one
(133) 8-(3-amino-piperidin-1-yl)-7-benzyl-1-methyl-2-isopropyl-1,7-dihydro-purin-6-one
(134) 8-(3-amino-piperidin-1-yl)-7-benzyl-1-methyl-2-butyl-1,7-dihydro-purin-6-one
(135) 8-(3-amino-piperidin-1-yl)-7-benzyl-1-methyl-2-(2-methyl-propyl)-1,7-dihydro-purin-6-one
(136) 8-(3-amino-piperidin-1-yl)-7-benzyl-1-methyl-2-pentyl-1,7-dihydro-purin-6-one
(137) 8-(3-amino-piperidin-1-yl)-7-benzyl-1-methyl-2-(3-methyl-butyl)-1,7-dihydro-purin-6-one
(138) 8-(3-amino-piperidin-1-yl)-7-benzyl-1-methyl-2-hexyl-1,7-dihydro-purin-6-one
(139) 8-(3-amino-piperidin-1-yl)-7-benzyl-1-methyl-2-(4-methyl-pentyl)-1,7-dihydro-purin-6-one (140) 8-(3-amino-piperidin-1-yl)-7-benzyl-1-methyl-2-allyl-1,7-dihydro-purin-6-one
(141) 8-(3-amino-piperidin-1-yl)-7-benzyl-1-methyl-2-(3-methyl-but-2-en-1-yl)-1,7-dihydro-purin-6-one
(142) 8-(3-amino-piperidin-1-yl)-7-benzyl-1-methyl-2-(hex-5-en-1-yl)-1,7-dihydro-purin-6-one
(143) 8-(3-amino-piperidin-1-yl)-7-benzyl-1-methyl-2-(pent-4-en-1-yl)-1,7-dihydro-purin-6-one
(144) 8-(3-amino-piperidin-1-yl)-7-benzyl-1-methyl-2-(prop-2-yn-1-yl)-1,7-dihydro-purin-6-one
(145) 8-(3-amino-piperidin-1-yl)-7-benzyl-1-methyl-2-(2-phenylethenyl)-1,7-dihydro-purin-6-one
(146) 8-(3-amino-piperidin-1-yl)-7-benzyl-1-methyl-2-[2-(4-methyl-phenyl)ethenyl]-1,7-dihydro-purin-6-one
(147) 8-(3-amino-piperidin-1-yl)-7-benzyl-1-methyl-2-[2-(2-chloro-phenyl)ethenyl]-1,7-dihydro-purin-6-one
(148) 8-(3-amino-piperidin-1-yl)-7-benzyl-1-methyl-2-[2-(3-fluoro-phenyl)ethenyl]-1,7-dihydro-purin-6-one
(149) 8-(3-amino-piperidin-1-yl)-7-benzyl-1-methyl-2-[2-(3,4-dimethoxy-phenyl)-ethenyl]-1,7-dihydro-purin-6-one
(150) 8-(3-amino-piperidin-1-yl)-7-benzyl-1-methyl-2-[2-(3-chloro-phenyl)ethenyl]-1,7-dihydro-purin-6-one
(151) 8-(3-amino-piperidin-1-yl)-7-benzyl-1-methyl-2-[2-(3-trifluoromethyl-phenyl)-ethenyl]-1,7-dihydro-purin-6-one
(152) 8-(3-amino-piperidin-1-yl)-7-benzyl-1-methyl-2-[2-(3-trifluoromethoxy-phenyl)-ethenyl]-1,7-dihydro-purin-6-one
(153) 8-(3-amino-piperidin-1-yl)-7-benzyl-1-methyl-2-(3-phenyl-prop-2-en-1-yl)-1,7-dihydro-purin-6-one
(154) 8-(3-amino-piperidin-1-yl)-7-benzyl-1-methyl-2-benzyl-1,7-dihydro-purin-6-one
(155) 8-(3-amino-piperidin-1-yl)-7-benzyl-1-methyl-2-phenyl-1,7-dihydro-purin-6-one
(156) 8-(3-amino-piperidin-1-yl)-7-benzyl-1-methyl-2-(3-phenyl-propyl)-1,7-dihydro-purin-6-one
(157) 8-(3-amino-piperidin-1-yl)-7-benzyl-1-methyl-2-(4-fluoro-benzyl)-1,7-dihydro-purin-6-one
(158) 8-(3-amino-piperidin-1-yl)-7-benzyl-1-methyl-2-(3-trifluoromethyl-benzyl)-1,7-dihydro-purin-6-one
(159) 8-(3-amino-piperidin-1-yl)-7-benzyl-1-methyl-2-(3-chloro-benzyl)-1,7-dihydro-purin-6-one
(160) 8-(3-amino-piperidin-1-yl)-7-benzyl-1-methyl-2-(3-bromo-benzyl)-1,7-dihydro-purin-6-one
(161) 8-(3-amino-piperidin-1-yl)-7-benzyl-1-methyl-2-(3-trifluoromethoxy-benzyl)-1,7-dihydro-purin-6-one
(162) 8-(3-amino-piperidin-1-yl)-7-benzyl-1-methyl-2-(3-methoxy-benzyl)-1,7-dihydro-purin-6-one
(163) 8-(3-amino-piperidin-1-yl)-7-benzyl-1-methyl-2-[2-(3-chloro-phenyl)ethyl]-1,7-dihydro-purin-6-one
(164) 8-(3-amino-piperidin-1-yl)-7-benzyl-1-methyl-2-[2-(2-fluoro-phenyl)ethyl]-1,7-dihydro-purin-6-one
(165) 8-(3-amino-piperidin-1-yl)-7-benzyl-1-methyl-2-[2-(4-methyl-phenyl)ethyl]-1,7-dihydro-purin-6-one
(166) 8-(3-amino-piperidin-1-yl)-7-benzyl-1-methyl-2-[2-(4-fluoro-phenyl)ethyl]-1,7-dihydro-purin-6-one
(167) 8-(3-amino-piperidin-1-yl)-7-benzyl-1-methyl-2-[2-(3-trifluoromethyl-phenyl)-ethyl]-1,7-dihydro-purin-6-one
(168) 8-(3-amino-piperidin-1-yl)-7-benzyl-1-methyl-2-cyclopentyl-1,7-dihydro-purin-6-one
(169) 8-(3-amino-piperidin-1-yl)-7-benzyl-1-methyl-2-cyclohexyl-1,7-dihydro-purin-6-one
(170) 8-(3-amino-piperidin-1-yl)-7-benzyl-1-methyl-2-(cyclohexylmethyl)-1,7-dihydro-purin-6-one
(171) 8-(3-amino-piperidin-1-yl)-7-benzyl-1-methyl-2-(cyclopentylmethyl)-1,7-dihydro-purin-6-one
(172) 8-(3-amino-piperidin-1-yl)-7-benzyl-1-methyl-2-(2-cyclohexyl-ethyl)-1,7-dihydro-purin-6-one
(173) 8-(3-amino-piperidin-1-yl)-7-benzyl-1-methyl-2-(furan-2-yl)-1,7-dihydro-purin-6-one
(174) 8-(3-amino-piperidin-1-yl)-7-benzyl-1-methyl-2-(thien-2-yl)-1,7-dihydro-purin-6-one
(175) 8-(3-amino-piperidin-1-yl)-7-benzyl-1-methyl-2-(pyridin-2-yl)-1,7-dihydro-purin-6-one
(176) 8-(3-amino-piperidin-1-yl)-7-benzyl-1-methyl-2-(pyridin-4-yl)-1,7-dihydro-purin-6-one
(177) 8-(3-amino-piperidin-1-yl)-7-benzyl-1-methyl-2-(furan-2-yl-methyl)-1,7-dihydro-purin-6-one
(178) 8-(3-amino-piperidin-1-yl)-7-benzyl-1-methyl-2-(thien-2-yl-methyl)-1,7-dihydro-purin-6-one
(179) 8-(3-amino-piperidin-1-yl)-7-benzyl-1-methyl-2-(pyridin-2-yl-methyl)-1,7-dihydro-purin-6-one
(180) 8-(3-amino-piperidin-1-yl)-7-benzyl-1-methyl-2-[2-(furan-2-yl)ethyl]-1,7-dihydro-purin-6-one
(181) 8-(3-amino-piperidin-1-yl)-7-benzyl-1-methyl-2-[2-(pyridin-2-yl)ethyl]-1,7-dihydro-purin-6-one
(182) 8-(3-amino-piperidin-1-yl)-7-benzyl-1-methyl-2-[3-(furan-2-yl)propyl]-1,7-dihydro-purin-6-one
(183) 8-(3-amino-piperidin-1-yl)-7-benzyl-1-methyl-2-[3-(pyridin-2-yl)propyl]-1,7-dihydro-purin-6-one
(184) 8-(3-amino-piperidin-1-yl)-2-benzylamino-1-methyl-7-(3-chloro-but-2-en-1-yl)-1,7-dihydro-purin-6-one
(185) 8-(3-amino-piperidin-1-yl)-2-benzylamino-1-methyl-7-(3-chloro-prop-2-en-1-yl)-1,7-dihydro-purin-6-one
(186) 8-(3-amino-piperidin-1-yl)-2-benzylamino-1-methyl-7-(3-trifluoromethyl-3-chloro-prop-2-en-1-yl)-1,7-dihydro-purin-6-one
(187) 8-(3-amino-piperidin-1-yl)-2-benzylamino-1-methyl-7-(3,3-dichloro-prop-2-en-1-yl)-1,7-dihydro-purin-6-one
(188) 8-(3-amino-piperidin-1-yl)-2-benzylamino-1-methyl-7-(but-2-yn-1-yl)-1,7-dihydro-purin-6-one
(189) 8-(3-amino-piperidin-1-yl)-2-benzylamino-1-methyl-7-(cyclohexyl-1-en-1-yl-methyl)-1,7-dihydro-purin-6-one
(190) 8-(3-amino-piperidin-1-yl)-2-benzylamino-1-methyl-7-(cyclohexylmethyl)-1,7-dihydro-purin-6-one
(191) 8-(3-amino-piperidin-1-yl)-2-benzylamino-1-methyl-7-(4-fluoro-benzyl)-1,7-dihydro-purin-6-one
(192) 8-(3-amino-piperidin-1-yl)-2-benzylamino-1-methyl-7-(2-chloro-benzyl)-1,7-dihydro-purin-6-one
(193) 8-(3-amino-piperidin-1-yl)-2-benzylamino-1-methyl-7-(3-bromo-benzyl)-1,7-dihydro-purin-6-one
(194) 8-(3-amino-piperidin-1-yl)-2-benzylamino-1-methyl-7-(3-methyl-benzyl)-1,7-dihydro-purin-6-one
(195) 8-(3-amino-piperidin-1-yl)-2-benzylamino-1-methyl-7-(3-trifluoromethyl-benzyl)-1,7-dihydro-purin-6-one
(196) 8-(3-amino-piperidin-1-yl)-2-benzylamino-1-methyl-7-(2-cyano-benzyl)-1,7-dihydro-purin-6-one
(197) 8-(3-amino-piperidin-1-yl)-2-benzylamino-1-methyl-7-(2-methoxy-benzyl)-1,7-dihydro-purin-6-one
(198) 8-(3-amino-piperidin-1-yl)-2-benzylamino-1-methyl-7-(3-trifluoromethoxy-benzyl)-1,7-dihydro-purin-6-one
(199) 8-(3-amino-piperidin-1-yl)-2-benzylamino-1-methyl-7-(3-difluoromethoxy-benzyl)-1,7-dihydro-purin-6-one
(200) 8-(3-amino-piperidin-1-yl)-2-benzylamino-1-methyl-7-(3,4-difluoro-benzyl)-1,7-dihydro-purin-6-one
(201) 8-(3-amino-piperidin-1-yl)-2-benzylamino-1-methyl-7-(naphth-1-yl-methyl)-1,7-dihydro-purin-6-one
(202) 8-(3-amino-piperidin-1-yl)-2-benzylamino-1-methyl-7-(furan-2-yl-methyl)-1,7-dihydro-purin-6-one (203) 8-(3-amino-piperidin-1-yl)-2-benzylamino-1-methyl-7-(thien-2-yl-methyl)-1,7-dihydro-purin-6-one
(204) 8-(3-amino-piperidin-1-yl)-2-benzylamino-1-methyl-7-(pyridin-2-yl-methyl)-1,7-dihydro-purin-6-one
(205) 8-(3-amino-piperidin-1-yl)-2-(2-phenylethyl)-1-methyl-7-(3-chloro-but-2-en-1-yl)-1,7-dihydro-purin-6-one
(206) 8-(3-amino-piperidin-1-yl)-2-(2-phenylethyl)-1-methyl-7-(3-chloro-prop-2-en-1-yl)-1,7-dihydro-purin-6-one
(207) 8-(3-amino-piperidin-1-yl)-2-(2-phenylethyl)-1-methyl-7-(3-trifluoromethyl-3-chloro-prop-2-en-1-yl)-1,7-dihydro-purin-6-one
(208) 8-(3-amino-piperidin-1-yl)-2-(2-phenylethyl)-1-methyl-7-(3,3-dichloro-prop-2-en-1-yl)-1,7-dihydro-purin-6-one
(209) 8-(3-amino-piperidin-1-yl)-2-(2-phenylethyl)-1-methyl-7-(but-2-yn-1-yl)-1,7-dihydro-purin-6-one
(210) 8-(3-amino-piperidin-1-yl)-2-(2-phenylethyl)-1-methyl-7-(cyclohexyl-1-en-1-yl-methyl)-1,7-dihydro-purin-6-one
(211) 8-(3-amino-piperidin-1-yl)-2-(2-phenylethyl)-1-methyl-7-(cyclohexylmethyl)-1,7-dihydro-purin-6-one
(212) 8-(3-amino-piperidin-1-yl)-2-(2-phenylethyl)-1-methyl-7-(4-fluoro-benzyl)-1,7-dihydro-purin-6-one
(213) 8-(3-amino-piperidin-1-yl)-2-(2-phenylethyl)-1-methyl-7-(2-chloro-benzyl)-1,7-dihydro-purin-6-one
(214) 8-(3-amino-piperidin-1-yl)-2-(2-phenylethyl)-1-methyl-7-(3-bromo-benzyl)-1,7-dihydro-purin-6-one
(215) 8-(3-amino-piperidin-1-yl)-2-(2-phenylethyl)-1-methyl-7-(3-methyl-benzyl)-1,7-dihydro-purin-6-one
(216) 8-(3-amino-piperidin-1-yl)-2-(2-phenylethyl)-1-methyl-7-(3-trifluoromethyl-benzyl)-1,7-dihydro-purin-6-one
(217) 8-(3-amino-piperidin-1-yl)-2-(2-phenylethyl)-1-methyl-7-(2-cyano-benzyl)-1,7-dihydro-purin-6-one
(218) 8-(3-amino-piperidin-1-yl)-2-(2-phenylethyl)-1-methyl-7-(2-methoxy-benzyl)-1,7-dihydro-purin-6-one
(219) 8-(3-amino-piperidin-1-yl)-2-(2-phenylethyl)-1-methyl-7-(3-trifluoromethoxy-benzyl)-1,7-dihydro-purin-6-one
(220) 8-(3-amino-piperidin-1-yl)-2-(2-phenylethyl)-1-methyl-7-(3-difluoromethoxy-benzyl)-1,7-dihydro-purin-6-one
(221) 8-(3-amino-piperidin-1-yl)-2-(2-phenylethyl)-1-methyl-7-(3,4-difluoro-benzyl)-1,7-dihydro-purin-6-one
(222) 8-(3-amino-piperidin-1-yl)-2-(2-phenylethyl)-1-methyl-7-(naphth-1-yl-methyl)-1,7-dihydro-purin-6-one
(223) 8-(3-amino-piperidin-1-yl)-2-(2-phenylethyl)-1-methyl-7-(furan-2-yl-methyl)-1,7-dihydro-purin-6-one
(224) 8-(3-amino-piperidin-1-yl)-2-(2-phenylethyl)-1-methyl-7-(thien-2-yl-methyl)-1,7-dihydro-purin-6-one
(225) 8-(3-amino-piperidin-1-yl)-2-(2-phenylethyl)-1-methyl-7-(pyridin-2-yl-methyl)-1,7-dihydro-purin-6-one
(226) 8-(3-amino-piperidin-1-yl)-2-($^2$-phenylethyl)-1-methyl-7-benzyl-1,7-dihydro-purin-6-one
(227) 8-(3-amino-pyrrolidin-1-yl)-2-benzylamino-1-methyl-7-benzyl-1,7-dihydro-purin-6-one
(228) 8-(piperidin-3-yl)-2-benzylamino-1-methyl-7-benzyl-1,7-dihydro-purin-6-one
(229) 8-(piperidin-4-yl)-2-benzylamino-1-methyl-7-benzyl-1,7-dihydro-purin-6-one
(230) 8-(3-amino-hexahydroazepin-1-yl)-2-benzylamino-1-methyl-7-benzyl-1,7-dihydro-purin-6-one
(231) 8-(4-amino-hexahydroazepin-1-yl)-2-benzylaamino-1-methyl-7-benzyl-1,7-dihydro-purin-6-one
(232) 8-(piperazin-1-yl)-2-benzylamino-1-methyl-7-benzyl-1,7-dihydro-purin-6-one
(233) 8-(1,4-diazepan-1-yl)-2-benzylamino-1-methyl-7-benzyl-1,7-dihydro-purin-6-one
(234) 8-(2-amino-cyclohexylamino)-2-benzylamino-1-methyl-7-benzyl-1,7-dihydro-purin-6-one
(235) 8-(3-amino-cyclohexyl)-2-benzylamino-1-methyl-7-benzyl-1,7-dihydro-purin-6-one
(236) 8-(3-amino-pyrrolidin-1-yl)-2-(2-phenylethyl)-1-methyl-7-benzyl-1,7-dihydro-purin-6-one
(237) 8-(piperidin-3-yl)-2-(2-phenylethyl)-1-methyl-7-benzyl-1,7-dihydro-purin-6-one
(238) 8-(piperidin-4-yl)-2-(2-phenylethyl)-1-methyl-7-benzyl-1,7-dihydro-purin-6-one
(239) 8-(3-amino-hexahydroazepin-1-yl)-2-(2-phenylethyl)-1-methyl-7-benzyl-1,7-dihydro-purin-6-one
(240) 8-(4-amino-hexahydroazepin-1-yl)-2-(2-phenylethyl)-1-methyl-7-benzyl-1,7-dihydro-purin-6-one
(241) 8-(piperazin-1-yl)-2-(2-phenylethyl)-1-methyl-7-benzyl-1,7-dihydro-purin-6-one
(242) 8-(1,4-diazepan-1-yl)-2-(2-phenylethyl)-1-methyl-7-benzyl-1,7-dihydro-purin-6-one
(243) 8-(2-amino-cyclohexylamino)-2-(2-phenylethyl)-1-methyl-7-benzyl-1,7-dihydro-purin-6-one
(244) 8-(3-amino-cyclohexyl)-2-(2-phenylethyl)-1-methyl-7-benzyl-1,7-dihydro-purin-6-one
(245) 8-(3-amino-piperidin-1-yl)-2-benzylamino-1-methyl-7-(but-2-en-1-yl)-1,7-dihydro-purin-6-one
(246) 8-(3-amino-piperidin-1-yl)-2-benzylamino-1-methyl-7-(2-methyl-but-2-en-1-yl)-1,7-dihydro-purin-6-one
(247) 8-(3-amino-piperidin-1-yl)-2-benzylamino-1-methyl-7-(2,3-dimethyl-but-2-en-1-yl)-1,7-dihydro-purin-6-one
(248) 8-(3-amino-piperidin-1-yl)-2-benzylamino-1-methyl-7-(cyclopent-1-en-1-yl-methyl)-1,7-dihydro-purin-6-one
(249) 8-(3-amino-piperidin-1-yl)-7-benzyl-1-(2-phenyl-2-oxo-ethyl)-1,7-dihydro-purin-6-one
(250) 8-(3-amino-piperidin-1-yl)-7-benzyl-1-[2-(2-amino-phenyl)-2-oxo-ethyl]-1,7-dihydro-purin-6-one
(251) 8-(3-amino-piperidin-1-yl)-7-benzyl-1-[2-(2-acetylamino-phenyl)-2-oxo-ethyl]-1,7-dihydro-purin-6-one
(252) 8-(3-amino-piperidin-1-yl)-7-benzyl-1-[2-(2-methylsulphonylamino-phenyl)-2-oxo-ethyl]-1,7-dihydro-purin-6-one
(253) 8-(3-amino-piperidin-1-yl)-7-benzyl-1-[2-(2-hydroxy-phenyl)-2-oxo-ethyl]-1,7-dihydro-purin-6-one
(254) 8-(3-amino-piperidin-1-yl)-7-benzyl-1-[2-(2-methoxy-phenyl)-2-oxo-ethyl]-1,7-dihydro-purin-6-one
(255) 8-(3-amino-piperidin-1-yl)-7-benzyl-1-{2-[2-(ethoxycarbonylmethoxy)-phenyl]-2-oxo-ethyl}-1,7-dihydro-purin-6-one
(256) 8-(3-amino-piperidin-1-yl)-7-benzyl-1-{2-[2-(aminocarbonylmethoxy)-phenyl]-2-oxo-ethyl}-1,7-dihydro-purin-6-one
(257) 8-(3-amino-piperidin-1-yl)-7-benzyl-1-{2-[2-(methylaminocarbonyl-methoxy)-phenyl]-2-oxo-ethyl}-1,7-dihydro-purin-6-one
(258) 8-(3-amino-piperidin-1-yl)-7-benzyl-1-{2-[2-(ethylaminocarbonyl-methoxy)-phenyl]-2-oxo-ethyl}-1,7-dihydro-purin-6-one
(259) 8-(3-amino-piperidin-1-yl)-7-benzyl-1-{2-[2-(dimethylaminocarbonyl-methoxy)-phenyl]-2-oxo-ethyl}-1,7-dihydro-purin-6-one
(260) 8-(3-amino-piperidin-1-yl)-7-benzyl-1-(naphth-1-yl-methyl)-1,7-dihydro-purin-6-one
(261) 8-(3-amino-piperidin-1-yl)-7-benzyl-1-(isoquinolin-1-yl-methyl)-1,7-dihydro-purin-6-one
(262) 8-(3-amino-piperidin-1-yl)-7-benzyl-1-(quinazolin-2-yl-methyl)-1,7-dihydro-purin-6-one (263) 8-(3-amino-piperidin-1-yl)-7-benzyl-1-(quinolin-4-yl-methyl)-1,7-dihydro-purin-6-one
(264) 8-(3-amino-piperidin-1-yl)-7-benzyl-1-(quinazolin-4-yl-methyl)-1,7-dihydro-purin-6-one
(265) 8-(3-amino-piperidin-1-yl)-7-benzyl-1-(2-phenyl-ethyl)-1,7-dihydro-purin-6-one
(266) 8-[(2-aminoethyl)amino]-7-benzyl-1-methyl-2-benzylamino-1,7-dihydro-purin-6-one
(267) 8-[N-methyl-N-(2-aminoethyl)-amino]-7-benzyl-1-methyl-2-benzylamino-1,7-dihydro-purin-6-one
(268) 8-[N-ethyl-N-(2-aminoethyl)-amino]-7-benzyl-1-methyl-2-benzylamino-1,7-dihydro-purin-6-one
(269) 8-(3-amino-piperidin-1-yl)-7-benzyl-1-methyl-2-[2-(2-cyanophenyl)ethyl]-1,7-dihydro-purin-6-one
(270) 8-(3-amino-piperidin-1-yl)-7-benzyl-1-methyl-2-[2-(2-aminocarbonyl-phenyl)-ethyl]-1,7-dihydro-purin-6-one
(271) 8-(3-amino-piperidin-1-yl)-7-benzyl-1-methyl-2-[2-(2-dimethylaminocarbonyl-phenyl)ethyl]-1,7-dihydro-purin-6-one
(272) 8-(3-amino-piperidin-1-yl)-7-benzyl-1-methyl-2-[2-(2-methylsulphonyl-phenyl)-ethyl]-1,7-dihydro-purin-6-one
(273) 8-(3-amino-piperidin-1-yl)-7-benzyl-1-methyl-2-[2-(2-methylsulphonylamino-phenyl)ethyl]-1,7-dihydro-purin-6-one
(274) 8-(3-amino-piperidin-1-yl)-7-benzyl-1-methyl-2-[(2-methylsulphonylamino-ethyl)-amino]-1,7-dihydro-purin-6-one
(275) 8-(3-amino-piperidin-1-yl)-7-benzyl-1-methyl-2-[(2-phenylsulphonylamino-ethyl)-amino]-1,7-dihydro-purin-6-one
(276) 8-(3-amino-piperidin-1-yl)-7-benzyl-1-methyl-2-[(naphth-1-yl-methyl)amino]-1,7-dihydro-purin-6-one
(277) 8-(3-amino-piperidin-1-yl)-7-benzyl-1-methyl-2-[(quinazolin-2-yl-methyl)amino]-1,7-dihydro-purin-6-one
(278) 8-(3-amino-piperidin-1-yl)-7-benzyl-1-methyl-2-[(isoquinolin-1-yl-methyl)amino]-1,7-dihydro-purin-6-one
(279) 8-(3-amino-piperidin-1-yl)-7-benzyl-1-(4,5-dimethyl-oxazol-2-yl-methyl)-1,7-dihydro-purin-6-one
(280) 8-(3-amino-piperidin-1-yl)-7-benzyl-1-(4,5-dimethyl-thiazol-2-yl-methyl)-1,7-dihydro-purin-6-one
(281) 8-(3-amino-piperidin-1-yl)-7-benzyl-1-(4,6-dimethyl-pyrimidin-2-yl-methyl)-1,7-dihydro-purin-6-one
(282) 8-(3-amino-piperidin-1-yl)-7-benzyl-1-(pyrazin-2-yl-methyl)-1,7-dihydro-purin-6-one
(283) 8-(3-amino-piperidin-1-yl)-7-benzyl-1-methyl-2-[(3-methyl-isoxazol-5-yl-methyl)-amino]-1,7-dihydro-purin-6-one
(284) 8-(3-amino-piperidin-1-yl)-7-benzyl-1-methyl-2-[(4,5-dimethyl-oxazol-2-yl-methyl)-amino]-1,7-dihydro-purin-6-one
(285) 8-(3-amino-piperidin-1-yl)-7-benzyl-1-methyl-2-[(pyrazin-2-yl-methyl)-amino]-1,7-dihydro-purin-6-one

EXAMPLE 2

Coated Tablets Containing 75 mg of Active Substance
1 tablet core contains:

| | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg
die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 3

Tablets Containing 100 mg of Active Substance
Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg
Diameter: 10 mm, biplanar, faceted on both sides and notched on one side.

EXAMPLE 4

Tablets Containing 150 mg of Active Substance
Composition:
1 tablet contains:

| | |
|---|---|
| active substance | 150.0 mg |
| powdered lactose | 89.0 mg |
| corn starch | 40.0 mg |
| colloidal silica | 10.0 mg |

-continued

|  |  |
|---|---|
| polyvinylpyrrolidone | 10.0 mg |
| magnesium stearate | 1.0 mg |
|  | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

EXAMPLE 5

Hard Gelatine Capsules Containing 150 mg of Active Substance 1 capsule contains:

|  |  |
|---|---|
| active substance | 150.0 mg |
| corn starch (dried) approx. | 80.0 mg |
| lactose (powderedapprox. | 87.0 mg |
| magnesium stearate | 3.0 mg |
| approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

EXAMPLE 6

Suppositories Containing 150 mg of Active Substance 1 suppository contains:

|  |  |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
|  | 2,000.0 mg |

Preparation:

After the suppository mass has been melted the active substance is homogeneously distributed therein and the melt is poured into chilled moulds.

EXAMPLE 7

Suspension Containing 50 mg of Active Substance 100 ml of suspension contain:

|  |  |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water ad | 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 8

Ampoules Containing 10 mg Active Substance
Composition:

|  |  |
|---|---|
| active substance | 10.0 mg |
| 0.01 N hydrochloric acid q.s. |  |
| double-distilled water ad | 2.0 ml |

Preparation:

The active substance is dissolved in the necessary amount of 0.01 N HCl, made isotonic with common salt, filtered sterile and transferred into 2 ml ampoules.

EXAMPLE 9

Ampoules Containing 50 mg of Active Substance
Composition:

|  |  |
|---|---|
| active substance | 50.0 mg |
| 0.01 N hydrochloric acid q.s. |  |
| double-distilled water ad | 10.0 ml |

Preparation:

The active substance is dissolved in the necessary amount of 0.01 N HCl, made isotonic with common salt, filtered sterile and transferred into 10 ml ampoules.

The invention claimed is:

1. A compound of the formula (I):

$$\text{(I)}$$

[Structure: imidazo-pyrimidine core with substituents $R^1$ on N, $R^2$ on C, $R^3$ on N, $R^4$ on C, and a carbonyl (=O) group]

wherein
R$^1$ denotes a hydrogen atom,
a C$_{1-8}$-alkyl group,
a C$_{3-8}$-alkenyl group,
a C$_{3-4}$-alkenyl group which is substituted by a C$_{1-2}$-alkyloxy-carbonyl, aminocarbonyl, C$_{1-3}$-alkylamino-carbonyl, di-(C$_{1-3}$-alkyl)-amino-carbonyl, pyrrolidin-1-ylcarbonyl, piperidin-1-ylcarbonyl or morpholin-4-ylcarbonyl group,
a C$_{3-8}$-alkynyl group,
a C$_{1-6}$-alkyl group substituted by a group R$_a$, where
R$_a$ denotes a C$_{3-7}$-cycloalkyl, heteroaryl, cyano, carboxy, C$_{1-3}$-alkyloxy-carbonyl, aminocarbonyl, C$_{1-3}$-alkylamino-carbonyl, di-(C$_{1-3}$-alkyl)-amino-carbonyl, pyrrolidin-1-ylcarbonyl, piperidin-1-ylcarbonyl, morpholin-4-ylcarbonyl, piperazin-1-ylcarbonyl, 4-methylpiperazin-1-ylcarbonyl or 4-ethylpiperazin-1-ylcarbonyl group,
a C$_{1-6}$-alkyl group substituted by a phenyl group, where the phenyl ring is substituted by the groups R$^{10}$ to R$^{14}$ and
R$^{10}$ denotes a hydrogen atom,
a fluorine, chlorine, bromine or iodine atom,
a C$_{1-4}$-alkyl, hydroxy or C$_{1-4}$-alkyloxy group,
a nitro, amino, C$_{1-3}$-alkylamino, di-(C$_{1-3}$-alkyl)-amino, cyan-C$_{1-3}$-alkylamino, N-(cyan-C$_{1-3}$-alkyl)-N—(C$_{1-3}$-alkyl)-amino, C$_{1-3}$-alkyloxy-carbonyl-C$_{1-3}$-alkylamino, pyrrolidin-1-yl, piperidin-1-yl, morpholin-4-yl, piperazin-1-yl or 4-(C$_{1-3}$-alkyl)-piperazin-1-yl group,
a formylamino, C$_{1-3}$-alkyl-carbonylamino, C$_{3-6}$-cycloalkyl-carbonylamino, C$_{3-6}$-cycloalkyl-C$_{1-3}$-alkyl-carbonylamino, arylcarbonylamino, aryl-C$_{1-3}$-alkyl-carbonylamino, C$_{1-3}$-alkyloxy-carbonylamino, aminocarbonylamino, C$_{1-3}$-alkyl-aminocarbonylamino, di-(C$_{1-3}$-alkyl)-aminocarbonylamino, pyrrolidin-1-yl-carbonylamino, piperidin-1-yl-carbonylamino, morpholin-4-yl-carbonylamino, piperazin-1-yl-carbonylamino or 4-(C$_{1-3}$-alkyl)-piperazin-1-yl-carbonylamino, C$_{1-3}$-alkyl-sulphonylamino, bis-(C$_{1-3}$-alkylsulphonyl)-amino, aminosulphonylamino, C$_{1-3}$-alkylamino-sulphonylamino, di-(C$_{1-3}$-alkyl)-amino-sulphonylamino, pyrrolidin-1-yl-sulphonylamino, piperidin-1-yl-sulphonylamino, morpholin-4-yl-sulphonylamino, piperazin-1-yl-sulphonylamino or 4-(C$_{1-3}$-alkyl)-piperazin-1-yl-sulphonylamino, (C$_{1-3}$-alkylamino)-thiocarbonylamino, (C$_{1-3}$-alkyloxy-carbonylamino)-carbonylamino, arylsulphonylamino or aryl-C$_{1-3}$-alkyl-sulphonylamino group,
an N—(C$_{1-3}$-alkyl)-formylamino, N—(C$_{1-3}$-alkyl)-N—(C$_{1-3}$-alkyl-carbonyl)-amino, N—(C$_{1-3}$-alkyl)-N—(C$_{3-6}$-cycloalkyl-carbonyl)-amino, N—(C$_{1-3}$-alkyl)-N—(C$_{3-6}$-cycloalkyl-C$_{1-3}$-alkyl-carbonyl)-amino, N—(C$_{1-3}$-alkyl)-N-(arylcarbonyl)-amino, N—(C$_{1-3}$-alkyl)-N-(aryl-C$_{1-3}$-alkyl-carbonyl)-amino, N—(C$_{1-3}$-alkyl)-N—(C$_{1-3}$-alkyloxy-carbonyl)-amino, N-(aminocarbonyl)-N—(C$_{1-3}$-alkyl)-amino, N—(C$_{1-3}$-alkyl-amino-carbonyl)-N—(C$_{1-3}$-alkyl)-amino, N-[di-(C$_{1-3}$-alkyl)aminocarbonyl]-N—(C$_{1-3}$-alkyl)-amino, N—(C$_{1-3}$-alkyl)-N—(C$_{1-3}$-alkyl-sulphonyl)-amino, N—(C$_{1-3}$-alkyl)-N-(arylsulphonyl)-amino or N—(C$_{1-3}$-alkyl)-N-(aryl-C$_{1-3}$-alkyl-sulphonyl)-amino group,
a 2-oxo-imidazolidin-1-yl, 2,4-dioxo-imidazolidin-1-yl, 2,5-dioxo-imidazolidin-1-yl or 2-oxo-hexahydro-pyrimidin-1-yl group wherein the nitrogen atom in the 3 position may be substituted in each case by a methyl or ethyl group,
a cyano, carboxy, C$_{1-3}$-alkyloxy-carbonyl, aminocarbonyl, C$_{1-3}$-alkyl-aminocarbonyl, di-(C$_{1-3}$-alkyl)-aminocarbonyl, pyrrolidin-1-yl-carbonyl, piperidin-1-yl-carbonyl, morpholin-4-yl-carbonyl, piperazin-1-yl-carbonyl or 4-(C$_{1-3}$-alkyl)-piperazin-1-yl-carbonyl group,
a C$_{1-3}$-alkyl-carbonyl or an arylcarbonyl group,
a carboxy-C$_{1-3}$-alkyl, C$_{1-3}$-alkyloxy-carbonyl-C$_{1-3}$-alkyl, cyano-C$_{1-3}$-alkyl, aminocarbonyl-C$_{1-3}$-alkyl, C$_{1-3}$-alkyl-aminocarbonyl-C$_{1-3}$-alkyl, di-(C$_{1-3}$-alkyl)-aminocarbonyl-C$_{1-3}$-alkyl, pyrrolidin-1-yl-carbonyl-C$_{1-3}$-alkyl, piperidin-1-yl-carbonyl-C$_{1-3}$-alkyl, morpholin-4-yl-carbonyl-C$_{1-3}$-alkyl, piperazin-1-yl-carbonyl-C$_{1-3}$-alkyl or 4-(C$_{1-3}$-alkyl)-piperazin-1-yl-carbonyl-C$_{1-3}$-alkyl group,
a carboxy-C$_{1-3}$-alkyloxy, C$_{1-3}$-alkyloxy-carbonyl-C$_{1-3}$-alkyloxy, cyano-C$_{1-3}$-alkyloxy, aminocarbonyl-C$_{1-3}$-alkyloxy, C$_{1-3}$-alkyl-aminocarbonyl-C$_{1-3}$-alkyloxy, di-(C$_{1-3}$-alkyl)-aminocarbonyl-C$_{1-3}$-alkyloxy, pyrrolidin-1-yl-carbonyl-C$_{1-3}$-alkyloxy, piperidin-1-yl-carbonyl-C$_{1-3}$-alkyloxy, morpholin-4-yl-carbonyl-C$_{1-3}$-alkyloxy, piperazin-1-yl-carbonyl-C$_{1-3}$-alkyloxy or 4-(C$_{1-3}$-alkyl)-piperazin-1-yl-carbonyl-C$_{1-3}$-alkyloxy group,
a hydroxy-C$_{1-3}$-alkyl, C$_{1-3}$-alkyloxy-C$_{1-3}$-alkyl, amino-C$_{1-3}$-alkyl, C$_{1-3}$-alkylamino-C$_{1-3}$-alkyl, di-(C$_{1-3}$-alkyl)-amino-C$_{1-3}$-alkyl, pyrrolidin-1-yl-C$_{1-3}$-alkyl, piperidin-1-yl-C$_{1-3}$-alkyl, morpholin-4-yl-C$_{1-3}$-alkyl, piperazin-1-yl-C$_{1-3}$-alkyl, 4-(C$_{1-3}$-alkyl)-piperazin-1-yl-C$_{1-3}$-alkyl group,
a hydroxy-C$_{1-3}$-alkyloxy, C$_{1-3}$-alkyloxy-C$_{1-3}$-alkyloxy, C$_{1-3}$-alkylsulphanyl-C$_{1-3}$-alkyloxy, C$_{1-3}$-alkylsulphinyl-C$_{1-3}$-alkyloxy, C$_{1-3}$-alkylsulphonyl-C$_{1-3}$-alkyloxy, amino-C$_{1-3}$-alkyloxy, C$_{1-3}$-alkylamino-C$_{1-3}$-alkyloxy, di-(C$_{1-3}$-alkyl)-amino-C$_{1-3}$-alkyloxy, pyrrolidin-1-yl-C$_{1-3}$-alkyloxy, piperidin-1-yl-C$_{1-3}$-alkyloxy, morpholin-4-yl-C$_{1-3}$-alkyloxy, piperazin-1-yl-C$_{1-3}$-alkyloxy, 4-(C$_{1-3}$-alkyl)-piperazin-1-yl-C$_{1-3}$-alkyloxy group,
a mercapto, C$_{1-3}$-alkylsulphanyl, C$_{1-3}$-alkysulphinyl, C$_{1-3}$-alkylsulphonyl, C$_{1-3}$-alkylsulphonyloxy, arylsulphonyloxy, trifluoromethylsulphanyl, trifluoromethylsulphinyl or trifluoromethylsulphonyl group,
a sulpho, aminosulphonyl, C$_{1-3}$-alkyl-aminosulphonyl, di-(C$_{1-3}$-alkyl)-aminosulphonyl, pyrrolidin-1-yl-sulphonyl, piperidin-1-yl-sulphonyl, morpholin-4-yl-sulphonyl, piperazin-1-yl-sulphonyl or 4-(C$_{1-3}$-alkyl)-piperazin-1-yl-sulphonyl group,
a methyl or methoxy group substituted by 1 to 3 fluorine atoms,
an ethyl or ethyloxy group substituted by 1 to 5 fluorine atoms,
a C$_{2-4}$-alkenyl or C$_{2-4}$-alkynyl group,
a C$_{3-4}$-alkenyloxy or C$_{3-4}$-alkynyloxy group,
a C$_{3-6}$-cycloalkyl or C$_{3-6}$-cycloalkyloxy group,
a C$_{3-6}$-cycloalkyl-C$_{1-3}$-alkyl or C$_{3-6}$-cycloalkyl-C$_{1-3}$-alkyloxy group or
an aryl, aryloxy, aryl-C$_{1-3}$-alkyl or aryl-C$_{1-3}$-alkyloxy group,
R$^{11}$ and R$^{12}$, which may be identical or different, in each case represent a hydrogen atom, a fluorine, chlorine, bromine or iodine atom, a C$_{1-3}$-alkyl, trifluoromethyl, hydroxy, C$_{1-3}$-alkyloxy or cyano group, or $R^{11}$ together with $R^{12}$, if they are bound to adjacent carbon atoms, also represent a methylenedioxy, difluoromethylenedioxy or a straight-chain $C_{3-5}$-alkylene group and $R^{13}$ and $R^{14}$, which may be identical or different, in each case represent a hydrogen atom, a fluorine, chlorine or bromine atom, a trifluoromethyl, $C_{1-3}$-alkyl or $C_{1-3}$-alkyloxy group, a phenyl-$C_{1-4}$-alkyl group wherein the alkyl moiety is substituted by a cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl-group and the phenyl moiety is substituted by the groups $R^{10}$ to $R^{14}$, while $R^{10}$ to $R^{14}$ are as hereinbefore defined, a phenyl group substituted by the groups $R^{10}$ to $R^{14}$, where $R^{10}$ to $R^{14}$ are as hereinbefore defined, a phenyl-$C_{2-3}$-alkenyl group wherein the phenyl moiety is substituted by the groups $R^{10}$ to $R^{14}$, where $R^{10}$ to $R^{14}$ are as hereinbefore defined, a phenyl-$(CH_2)_m$-A-$(CH_2)_n$— group wherein the phenyl moiety is substituted by $R^{10}$ to $R^{14}$, where $R^{10}$ to $R^{14}$ are as hereinbefore defined and A represents a carbonyl group, m represents the number 0, 1 or 2 and n represents the number 1, 2 or 3, a phenylcarbonylmethyl group wherein the phenyl moiety is substituted by $R^{10}$ to $R^{14}$, where $R^{10}$ to $R^{14}$ are as hereinbefore defined and the methyl moiety is substituted by a $C_{1-3}$-alkyl group, a phenyl-$(CH_2)_m$—B—$(CH_2)_n$— group wherein the phenyl moiety is substituted by $R^{10}$ to $R^{14}$, where $R^{10}$ to $R^{14}$, m and n are as hereinbefore defined and B denotes a methylene group which is substituted by a hydroxy, $C_{1-3}$-alkyloxy, amino, $C_{1-3}$-alkylamino, di-($C_{1-3}$-alkyl)-amino, mercapto, $C_{1-3}$-alkylsulphanyl, $C_{1-3}$-alkylsulphinyl or $C_{1-3}$-alkylsulphonyl group and is optionally additionally substituted by a methyl or ethyl group, a naphthyl-$C_{1-3}$-alkyl group wherein the naphthyl moiety is substituted by the groups to $R^{10}$ to $R^{14}$, where $R^{10}$ to $R^{14}$ are as hereinbefore defined, a naphthyl-$(CH_2)_m$-A-$(CH_2)_n$— group wherein the naphthyl moiety is substituted by $R^{10}$ to $R^{14}$, where $R^{10}$ to $R^{14}$, A, m and n are as hereinbefore defined, a naphthyl-$(CH_2)_m$—B—$(CH_2)_n$— group wherein the naphthyl moiety is substituted by $R^{10}$ to $R^{14}$, where $R^{10}$ to $R^{14}$, B, m and n are as hereinbefore defined, a [1,4]naphthoquinon-2-yl, chromen-4-on-3-yl, 1-oxoindan-2-yl, 1,3-dioxoindan-2-yl or 2,3-dihydro-3-oxobenzofuran-2-yl group, a heteroaryl-$(CH_2)_m$-A-$(CH_2)_n$ group where A, m and n are as hereinbefore defined, a heteroaryl-$(CH_2)_m$—B—$(CH_2)_n$ group where B, m and n are as hereinbefore defined, a $C_{1-6}$-alkyl-A-$(CH_2)_n$ group where A and n are as hereinbefore defined, a $C_{3-7}$-cycloalkyl-$(CH_2)_m$-A-$(CH_2)_n$ group where A, m and n are as hereinbefore defined, a $C_{3-7}$-cycloalkyl-$(CH_2)_m$—B—$(CH_2)_n$ group where B, m and n are as hereinbefore defined, an $R^{21}$-A-$(CH_2)_n$— group wherein $R^{21}$ denotes a $C_{1-3}$-alkyloxycarbonyl, aminocarbonyl, $C_{1-3}$-alkylaminocarbonyl, di-($C_{1-3}$-alkyl)aminocarbonyl, pyrrolidin-1-ylcarbonyl, piperidin-1-yl-carbonyl or morpholin-4-yl-carbonyl, 4-methylpiperazin-1-yl-carbonyl or 4-ethylpiperazin-1-yl-carbonyl group and A and n are as hereinbefore defined, a phenyl-$(CH_2)_m$-D-$C_{1-3}$-alkyl group wherein the phenyl moiety is substituted by the groups $R^{10}$ to $R^{14}$, where $R^{10}$ to $R^{14}$ and m are as mentioned hereinbefore and D denotes an oxygen or sulphur atom, —NH—, $C_{1-3}$-alkylimino, sulphinyl or sulphonyl group, a naphthyl-$(CH_2)_m$-D-$C_{1-3}$-alkyl group wherein the naphthyl moiety is substituted by the groups $R^{10}$ to $R^{14}$, where $R^{10}$ to $R^{14}$, D and m are as mentioned hereinbefore, a $C_{2-6}$-alkyl group substituted by a group $R_b$, where $R_b$ is isolated from the cyclic nitrogen atom in the 1 position of the purine skeleton by at least two carbon atoms and $R_b$ denotes a hydroxy, $C_{1-3}$-alkyloxy, mercapto, $C_{1-3}$-alkylsulphanyl, $C_{1-3}$-alkylsulphinyl, $C_{1-3}$-alkylsulphonyl, amino, $C_{1-3}$-alkyl-carbonylamino, $C_{3-6}$-cycloalkyl-carbonyl-amino, arylcarbonylamino, $C_{1-3}$-alkylamino, di-($C_{1-3}$-alkyl)-amino, pyrrolidin-1-yl, piperidin-1-yl, morpholin-4-yl, piperazin-1-yl or 4-($C_{1-3}$-alkyl)-piperazin-1-yl group, a $C_{3-6}$-cycloalkyl group, or an amino or arylcarbonylamino group, $R^2$ denotes a hydrogen atom, a $C_{1-8}$-alkyl group, a $C_{3-8}$-alkenyl group, a $C_{3-4}$-alkenyl group which is substituted by a $C_{1-2}$-alkyloxy-carbonyl, aminocarbonyl, $C_{1-3}$-alkylamino-carbonyl, di-($C_{1-3}$-alkyl)-amino-carbonyl, pyrrolidin-1-ylcarbonyl, piperidin-1-ylcarbonyl or morpholin-4-ylcarbonyl group, a $C_{3-8}$-alkynyl group, a $C_{3-6}$-cycloalkyl group, a $C_{1-6}$-alkyl group substituted by a group $R_a$, where $R_a$ is as hereinbefore defined, a phenyl group which is substituted by $R^{10}$ to $R^{14}$, where $R^{10}$ to $R^{14}$ are as hereinbefore defined, a $C_{1-6}$-alkyl group substituted by a phenyl group, wherein the phenyl ring is substituted by the groups $R^{10}$ to $R^{14}$ and $R^{10}$ to $R^{14}$ are as hereinbefore defined, a phenyl-$C_{1-4}$-alkyl group wherein the alkyl moiety is substituted by a cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl group and the phenyl moiety is substituted by the groups $R^{10}$ to $R^{14}$, where $R^{10}$ to $R^{14}$ are as hereinbefore defined, a phenyl-$C_{2-3}$-alkenyl group wherein the phenyl moiety is substituted by $R^{10}$ to $R^{14}$, where $R^{10}$ to $R^{14}$ are as hereinbefore defined, a heteroaryl group, a phenyl-$(CH_2)_m$-A or phenyl-$(CH_2)_m$-A-$(CH_2)_n$ group wherein the phenyl moiety is substituted in each case by $R^{10}$ to $R^{14}$, while A, $R^{10}$ to $R^{14}$, m and n are as hereinbefore defined, a phenylcarbonylmethyl group wherein the phenyl moiety is substituted by $R^{10}$ to $R^{14}$, where $R^{10}$ to $R^{14}$ are as hereinbefore defined and the methyl moiety is substituted by a $C_{1-3}$-alkyl group, a phenyl-$(CH_2)_m$—B or phenyl-$(CH_2)_m$—B—$(CH_2)_n$ group wherein the phenyl moiety is substituted in each case by $R^{10}$ to $R^{14}$, while B, $R^{10}$ to $R^{14}$, m and n are as hereinbefore defined, a naphthyl-$C_{1-3}$-alkyl group wherein the naphthyl moiety is substituted by the groups $R^{10}$ to $R^{14}$, where $R^{10}$ to $R^{14}$ are as hereinbefore defined, a naphthyl-$(CH_2)_m$-A or naphthyl-$(CH_2)_m$-A-$(CH_2)_n$ group wherein the naphthyl moiety is substituted in each case by $R^{10}$ to $R^{14}$, where $R^{10}$ to $R^{14}$, A, m and n are as hereinbefore defined, a naphthyl-$(CH_2)_m$—B or naphthyl-$(CH_2)_m$—B—$(CH_2)_n$ group wherein the naphthyl moiety is substituted in each case by $R^{10}$ to $R^{14}$, where $R^{10}$ to $R^{14}$, B, m and n are as hereinbefore defined, a heteroaryl-$(CH_2)_m$-A or heteroaryl-$(CH_2)_m$-A-$(CH_2)_n$ group where A, m and n are as hereinbefore defined, a heteroaryl-$(CH_2)_m$—B or heteroaryl-$(CH_2)_m$—B—$(CH_2)_n$ group where B, m and n are as hereinbefore defined, a $C_{1-6}$-alkyl-A or $C_{1-6}$-alkyl-A-$(CH_2)_n$ group where A and n are as hereinbefore defined, a $C_{3-7}$-cycloalkyl-$(CH_2)_m$-A or $C_{3-7}$-cycloalkyl-$(CH_2)_m$-A-$(CH_2)_n$ group where A, m and n are as hereinbefore defined, a $C_{3-7}$-cycloalkyl-$(CH_2)_m$—B or $C_{3-7}$-cycloalkyl-$(CH_2)_m$—B—$(CH_2)_n$ group where B, m and n are as hereinbefore defined, an $R^{21}$-A-$(CH_2)_n$ group wherein $R^{21}$, A and n are as hereinbefore defined, a phenyl-$(CH_2)_m$-D-$C_{1-3}$-alkyl group wherein the phenyl moiety is substituted by the groups $R^{10}$ to $R^{14}$, where $R^{10}$ to $R^{14}$, D and m are as mentioned hereinbefore, a naphthyl-$(CH_2)_m$-D-$C_{1-3}$-alkyl group wherein the naphthyl moiety is substituted by the groups $R^{10}$ to $R^{14}$, where $R^{10}$ to $R^{14}$, D and m are as mentioned hereinbefore, a $C_{1-6}$-alkyl group substituted by a group $R_b$, where $R_b$ is as hereinbefore defined, a cyano, carboxy, $C_{1-3}$-alkyloxy-carbonyl, aminocarbonyl, $C_{1-3}$-alkylamino-carbonyl, di-($C_{1-3}$-alkyl)-amino-carbonyl, pyrrolidin-1-ylcarbonyl, piperidin-1-ylcarbonyl, morpholin-4-ylcarbonyl, piperazin-1-ylcarbonyl, 4-methylpiperazin-1-ylcarbonyl or 4-ethylpiperazin-1-ylcarbonyl group, an amino, $C_{1-6}$-alkylamino or di-($C_{1-6}$-alkyl)-amino group, an amino group substituted by the groups $R^{15}$ and $R^{16}$ wherein
$R^{15}$ denotes a hydrogen atom or a $C_{1-6}$-alkyl group and
$R^{16}$ denotes a $C_{1-6}$-alkyl group which is substituted by $R_a$, where $R_a$ is as hereinbefore defined, an amino group substituted by the groups $R^{15}$ and $R^{17}$ wherein
$R^{15}$ is as hereinbefore defined and
$R^{17}$ denotes a $C_{2-6}$-alkyl group which is substituted by a hydroxy, $C_{1-3}$-alkyloxy, aryloxy, mercapto, $C_{1-3}$-alkylsulphanyl, $C_{1-3}$-alkylsulphinyl, $C_{1-3}$-alkylsulphonyl, $C_{1-3}$-alkylsulphonylamino, arylsulphanyl, arylsulphinyl, arylsulphonyl, arylsulphonylamino, $C_{1-3}$-alkyl-carbonylamino, $C_{3-6}$-cycloalkyl-carbonylamino, arylcarbonylamino, $C_{1-3}$-alkyl-oxycarbonylamino, aminocarbonylamino, $C_{1-3}$-alkyl-aminocarbonylamino, di-($C_{1-3}$-alkyl)-aminocarbonylamino, amino, $C_{1-3}$-alkylamino, di-($C_{1-3}$-alkyl)-amino, pyrrolidin-1-yl, piperidin-1-yl, morpholin-4-yl, piperazin-1-yl or 4-($C_{1-3}$-alkyl)-piperazin-1-yl group, a $C_{3-6}$-cycloalkylamino or N—($C_{3-6}$-cycloalkyl)-N—($C_{1-3}$-alkyl)-amino group, a phenylamino or N-(phenyl)-N—($C_{1-3}$-alkyl)-amino group wherein the phenyl moiety is substituted in each case by $R^{10}$ to $R^{14}$, where $R^{10}$ to $R^{14}$ are as hereinbefore defined, a phenyl-$C_{1-6}$-alkylamino or N-(phenyl-$C_{1-6}$-alkyl)-N—($C_{1-3}$-alkyl)-amino group wherein the phenyl moiety is substituted in each case by $R^{10}$ to $R^{14}$, where $R^{10}$ to $R^{14}$ are as hereinbefore defined, a naphthylamino or N-(naphthyl)-N—($C_{1-3}$-alkyl)-amino group, a naphthyl-$C_{1-6}$-alkylamino or N-(naphthyl-$C_{1-6}$-alkyl)-N—($C_{1-3}$-alkyl)-amino group, a heteroarylamino or N-(heteroaryl)-N—($C_{1-3}$-alkyl)-amino group, a pyrrolidin-1-yl, piperidin-1-yl, homopiperidin-1-yl, morpholin-4-yl, homomorpholin-4-yl, piperazin-1-yl, 4-($C_{1-3}$-alkyl)-piperazin-1-yl, homopiperazin-1-yl or 4-($C_{1-3}$-alkyl)-homopiperazin-1-yl group, or a $C_{1-6}$-alkyloxy, $C_{3-6}$-cycloalkyloxy or $C_{3-6}$-cycloalkyl-$C_{1-6}$-alkyloxy group, a $C_{1-6}$-alkylsulphanyl, $C_{3-6}$-cycloalkylsulphanyl or $C_{3-6}$-cycloalkyl-$C_{1-6}$-alkylsulphanyl group, a phenyloxy or phenylsulphanyl group wherein the phenyl moiety is substituted in each case by $R^{10}$ to $R^{14}$, where $R^{10}$ to $R^{14}$ are as hereinbefore defined, a phenyl-$C_{1-6}$-alkyloxy or phenyl-$C_{1-6}$-alkylsulphanyl group wherein the phenyl moiety is substituted in each case by $R^{10}$ to $R^{14}$, where $R^{10}$ to $R^{14}$ are as hereinbefore defined, a naphthyloxy or a naphthylsulphanyl group wherein the naphthyl moiety is substituted in each case by $R^{10}$ to $R^{14}$, where $R^{10}$ to $R^{14}$ are as hereinbefore defined, a naphthyl-$C_{1-6}$-alkyloxy or naphthyl-$C_{1-6}$-alkylsulphanyl group wherein the naphthyl moiety is substituted in each case by $R^{10}$ to $R^{14}$, where $R^{10}$ to $R^{14}$ are as hereinbefore defined, a heteroaryloxy or heteroarylsulphanyl group or a heteroaryl-$C_{1-6}$-alkyloxy or heteroaryl-$C_{1-6}$-alkylsulphanyl group, $R^3$ denotes a $C_{1-8}$-alkyl group, a $C_{1-4}$-alkyl group substituted by the group $R_c$, where
$R_c$ denotes a $C_{3-7}$-cycloalkyl group optionally substituted by one or two $C_{1-3}$-alkyl groups,
a $C_{5-7}$-cycloalkenyl group optionally substituted by one or two $C_{1-3}$-alkyl groups,
an aryl group or
a furanyl, thienyl, oxazolyl, isoxazolyl, thiazolyl, isothiazolyl, pyridyl, pyridazinyl, pyrimidyl or pyrazinyl group, while the above-mentioned heterocyclic groups may each be substituted by one or two $C_{1-3}$-alkyl groups or by a fluorine, chlorine, bromine or iodine atom or by a trifluoromethyl, cyano or $C_{1-3}$-alkyloxy group, a $C_{3-8}$-alkenyl group, a $C_{3-6}$-alkenyl group substituted by a fluorine, chlorine or bromine atom or a trifluoromethyl group, a $C_{3-8}$-alkynyl group, an aryl group or an aryl-$C_{2-4}$-alkenyl group, and $R^4$ denotes an azetidin-1-yl or pyrrolidin-1-yl group which is substituted in the 3 position by an amino, $C_{1-3}$-alkylamino or di-($C_{1-3}$-alkyl)-amino group and may additionally be substituted by one or two $C_{1-3}$-alkyl groups, a piperidin-1-yl or hexahydroazepin-1-yl group which is substituted in the 3 position or in the 4 position by an amino, $C_{1-3}$-alkylamino or di-($C_{1-3}$-alkyl)amino group and may additionally be substituted by one or two $C_{1-3}$-alkyl groups, a 3-amino-piperidin-1-yl group wherein the piperidin-1-yl-moiety is additionally substituted by an aminocarbonyl, $C_{1-2}$-alkyl-aminocarbonyl, di-($C_{1-2}$-alkyl)-aminocarbonyl, pyrrolidin-1-yl-carbonyl, (2-cyano-pyrrolidin-1-yl-)carbonyl, thiazolidin-3-yl-carbonyl, (4-cyano-thiazolidin-3-yl)carbonyl, piperidin-1-ylcarbonyl or morpholin-4-ylcarbonyl group, a 3-amino-piperidin-1-yl group wherein the piperidin-1-yl moiety is additionally substituted in the 4 position or 5 position by a hydroxy or methoxy group, a 3-amino-piperidin-1-yl group wherein the methylene group is replaced in the 2 position or 6 position by a carbonyl group, a piperidin-1-yl or hexahydroazepin-1-yl- group substituted in the 3 position by an amino, $C_{1-3}$-alkylamino or di-($C_{1-3}$-alkyl)-amino group, wherein two hydrogen atoms on the carbon skeleton of the piperidin-1-yl or hexahydroazepin-1-yl group are each replaced by a straight-chain alkylene bridge, this bridge containing 2 to 5 carbon atoms if the two hydrogen atoms are on the same carbon atom, or 1 to 4 carbon atoms if the hydrogen atoms are on adjacent carbon atoms, or 1 to 4 carbon atoms if the hydrogen atoms are on carbon atoms which are separated by one atom, or 1 to 3 carbon atoms if the hydrogen atoms are on carbon atoms which are separated by two atoms, an azetidin-1-yl, pyrrolidin-1-yl, piperidin-1-yl or hexahydroazepin-1-yl group which is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, a piperazin-1-yl or [1,4]diazepan-1-yl group optionally substituted on the carbon skeleton by one or two $C_{1-3}$-alkyl groups, a 3-imino-piperazin-1-yl, 3-imino-[1,4]diazepan-1-yl or 5-imino-[1,4]diazepan-1-yl group optionally substituted on the carbon skeleton by one or two $C_{1-3}$-alkyl groups, a [1,4]diazepan-1-yl group optionally substituted by one or two $C_{1-3}$-alkyl groups, which is substituted in the 6 position by an amino group, a $C_{3-7}$-cycloalkyl group which is substituted by an amino, $C_{1-3}$-alkylamino or di-($C_{1-3}$-alkyl)-amino group, a $C_{3-7}$-cycloalkyl group which is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, a $C_{3-7}$-cycloalkyl-$C_{1-2}$-alkyl group wherein the cycloalkyl moiety is substituted by an amino, $C_{1-3}$-alkylamino or di-($C_{1-3}$-alkyl)-amino group, a $C_{3-7}$-cycloalkyl-$C_{1-2}$-alkyl group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, a $C_{3-7}$-cycloalkylamino group wherein the cycloalkyl moiety is substituted by an amino, $C_{1-3}$-alkylamino or di-($C_{1-3}$-alkyl)-amino group, while the two nitrogen atoms on the cycloalkyl moiety are separated from one another by at least two carbon atoms, an N—($C_{3-7}$-cycloalkyl)-N—($C_{1-3}$-alkyl)-amino group wherein the cycloalkyl moiety is substituted by an amino, $C_{1-3}$-alkylamino or di-($C_{1-3}$-alkyl)-amino group, while the two nitrogen atoms on the cycloalkyl moiety are separated from one another by at least two carbon atoms, a $C_{3-7}$-cycloalkylamino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, an N—($C_{3-7}$-cycloalkyl)-N—($C_{1-3}$-alkyl)-amino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, a $C_{3-7}$-cycloalkyl-$C_{1-2}$-alkyl-amino group wherein the cycloalkyl moiety is substituted by an amino, $C_{1-3}$-alkylamino or di-($C_{1-3}$-alkyl)-amino group, an N—($C_{3-7}$-cycloalkyl-$C_{1-2}$-alkyl)-N—($C_{1-2}$-alkyl)-amino group wherein the cycloalkyl moiety is substituted by an amino, $C_{1-3}$-alkylamino or di-($C_{1-3}$-alkyl)-amino group, a $C_{3-7}$-cycloalkyl-$C_{1-2}$-alkyl-amino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, an N—($C_{3-7}$-cycloalkyl-$C_{1-2}$-alkyl)-N—($C_{1-2}$-alkyl)-amino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, an $R^{19}$—$C_{2-4}$-alkylamino group wherein $R^{19}$ is separated from the nitrogen atom of the $C_{2-4}$-alkylamino moiety by at least two carbon atoms and $R^{19}$ denotes an amino, $C_{1-3}$-alkylamino or di-($C_{1-3}$-alkyl)-amino group, an $R^{19}$—$C_{2-4}$-alkylamino group wherein the nitrogen atom of the $C_{2-4}$-alkylamino moiety is substituted by a $C_{1-3}$-alkyl group and $R^{19}$ is separated from the nitrogen atom of the $C_{2-4}$-alkylamino moiety by at least two carbon atoms, where $R^{19}$ is as hereinbefore defined, an amino group substituted by the group $R^{20}$ wherein
$R^{20}$ denotes an azetidin-3-yl, azetidin-2-ylmethyl, azetidin-3-ylmethyl, pyrrolidin-3-yl, pyrrolidin-2-ylmethyl, pyrrolidin-3-ylmethyl, piperidin-2-ylmethyl, piperidin-3-ylmethyl or piperidin-4-ylmethyl group, while the groups mentioned for $R^{20}$ may each be substituted by one or two $C_{1-3}$-alkyl groups, an amino group substituted by the group $R^{20}$ and a $C_{1-3}$-alkyl group wherein $R^{20}$ is as hereinbefore defined, while the groups mentioned for $R^{20}$ may each be substituted by one or two $C_{1-3}$-alkyl groups, an $R^{19}$—$C_{3-4}$-alkyl group wherein the $C_{3-4}$-alkyl moiety is straight-chained and may additionally be substituted by one or two $C_{1-3}$-alkyl groups, where $R^{19}$ is as hereinbefore defined, a 3-amino-2-oxo-piperidin-5-yl or 3-amino-2-oxo-1-methyl-piperidin-5-yl group, a pyrrolidin-3-yl, piperidin-3-yl, piperidin-4-yl, hexahydroazepin-3-yl or hexahydroazepin-4-yl group which is substituted in the 1 position by an amino, $C_{1-3}$-alkylamino or di-($C_{1-3}$-alkyl)amino group, or an azetidin-2-yl-$C_{1-2}$-alkyl, azetidin-3-yl-$C_{1-2}$-alkyl, pyrrolidin-2-yl-$C_{1-2}$-alkyl pyrrolidin-3-yl, pyrrolidin-3-yl-$C_{1-2}$-alkyl, piperidin-3-yl, or piperidin-4-yl, while the above-mentioned groups may each be substituted by one or two $C_{1-3}$-alkyl groups, while by the aryl groups mentioned in the definition of the above groups are meant phenyl or naphthyl groups, which may be mono- or disubstituted by $R_h$ independently of one another, where the substituents are identical or different and $R_h$ denotes a fluorine, chlorine, bromine or iodine atom, a trifluoromethyl, cyano, nitro, amino, aminocarbonyl, aminosulphonyl, methylsulphonyl, acetylamino, methylsulphonylamino, $C_{1-3}$-alkyl, cyclopropyl, ethenyl, ethynyl, hydroxy, $C_{1-3}$-alkyloxy, difluoromethoxy or trifluoromethoxy group, by the heteroaryl groups mentioned in the definitions of the above-mentioned groups are meant a pyrrolyl, furanyl, thienyl, pyridyl, indolyl, benzofuranyl, benzothiophenyl, quinolinyl or isoquinolinyl group, or a pyrrolyl, furanyl, thienyl or pyridyl group wherein one or two methyne groups are replaced by nitrogen atoms, or an indolyl, benzofuranyl, benzothiophenyl, quinolinyl or isoquinolinyl group wherein one to three methyne groups are replaced by nitrogen atoms, or a 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 3,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, cumarinyl, 2,3-dihydro-benzo[1,4]dioxinyl or 3,4-dihydro-3-oxo-2H-benzo[1,4]oxazinyl group, while the above-mentioned heteroaryl groups may be substituted by $R^{10}$ to $R^{14}$, where $R^{10}$ to $R^{14}$ are as hereinbefore defined, and, unless otherwise stated, the above-mentioned alkyl, alkenyl and alkynyl groups may be straight-chain or branched, as well as the derivatives which are N-oxidised at the cyclic nitrogen atom in the 3 position or 9 position of the hypoxanthine skeleton, as well as the derivatives wherein the 6-oxo group of the hypoxanthine skeleton is replaced by a thioxo group, the tautomers, enantiomers, diastereomers, the mixtures thereof, the prodrugs thereof and the salts thereof.

2. The compound according to claim 1,
wherein $R^1$, $R^2$ and $R^3$ are defined as in claim 1 and
$R^4$ denotes a pyrrolidin-1-yl group which is substituted in the 3 position by an amino group,
a piperidin-1-yl group which is substituted in the 3 position by an amino group,
a piperidin-3-yl or piperidin-4-yl group,
a hexahydroazepin-1-yl group which is substituted in the 3 position or 4 position by an amino group,
a piperazin-1-yl or [1,4]diazepan-1-yl group,
a (2-aminocyclohexyl)amino group,
a cyclohexyl group which is substituted in the 3 position by an amino group,
or an N-(2-aminoethyl)-methylamino or an N-(2-aminoethyl)-ethylamino group,
the tautomers, enantiomers, diastereomers, the mixtures thereof, the prodrugs and the salts thereof.

3. The compound according to claim 1, wherein
$R^1$ denotes a hydrogen atom,
a $C_{1-6}$-alkyl group,
a $C_{3-6}$-alkenyl group,
a $C_{3-4}$-alkynyl group,
a $C_{3-6}$-cycloalkylmethyl group,
a phenyl-$C_{1-3}$-alkyl group wherein the phenyl moiety is substituted by $R^{10}$ and $R^{11}$, where
$R^{10}$ denotes a hydrogen atom, a fluorine, chlorine or bromine atom,
a methyl or trifluoromethyl group,
a cyano, aminocarbonyl, dimethylaminocarbonyl or methylsulphonyl group,
an amino, acetylamino or methylsulphonylamino group,
a hydroxy, methoxy, difluoromethoxy, trifluoromethoxy, carboxymethoxy, methoxycarbonylmethoxy, ethyloxycarbonylmethoxy, aminocarbonylmethoxy, methylaminocarbonylmethoxy, ethylaminocarbonylmethoxy or dimethylaminocarbonylmethoxy group and
$R^{11}$ denotes a hydrogen atom, a fluorine or chlorine atom,
or a methyl or methoxy group,
a naphthylmethyl group wherein the naphthyl moiety is substituted by $R^{10}$ and $R^{11}$, where $R^{10}$ and $R^{11}$ are as hereinbefore defined,
a heteroarylmethyl group where the term
heteroaryl denotes a furanyl, thienyl, oxazolyl, isoxazolyl, thiazolyl, pyridyl, pyrimidinyl, pyrazinyl, quinolinyl, isoquinolinyl or quinazolinyl group and the above-mentioned heteroaryl groups are substituted by $R^{10}$ and $R^{11}$, where $R^{10}$ and $R^{11}$ are as hereinbefore defined,
a phenylcarbonylmethyl group wherein the phenyl moiety is substituted by $R^{10}$ and $R^{11}$, where $R^{10}$ and $R^{11}$ are as hereinbefore defined,
a furanylcarbonylmethyl, thienylcarbonylmethyl or pyridylcarbonylmethyl group,
or a 2-oxo-propyl or cyclohexylcarbonylmethyl group,
$R^2$ denotes a hydrogen atom,
a $C_{1-6}$-alkyl group,
a $C_{3-6}$-alkenyl group,
a $C_{3-4}$-alkynyl group,
a $C_{3-6}$-cycloalkyl or $C_{3-6}$-cycloalkyl-$C_{1-3}$-alkyl group,
a phenyl group which is substituted by $R^{10}$ and $R^{11}$, where $R^{10}$ and $R^{11}$ are as hereinbefore defined,
a phenyl-$C_{1-3}$-alkyl group wherein the phenyl moiety is substituted by $R^{10}$ and $R^{11}$, where $R^{10}$ and $R^{11}$ are as hereinbefore defined,
a phenyl-$C_{2-3}$-alkenyl group wherein the phenyl moiety is substituted by $R^{10}$ and $R^{11}$, where $R^{10}$ and $R^{11}$ are as hereinbefore defined,
a phenylcarbonylmethyl group wherein the phenyl moiety is substituted by $R^{10}$ and $R^{11}$, where $R^{10}$ and $R^{11}$ are as hereinbefore defined,
a furanyl, thienyl or pyridyl group,
a furanyl-$C_{1-3}$-alkyl, thienyl-$C_{1-3}$-alkyl or pyridyl-$C_{1-3}$-alkyl group,
a cyano group,
an amino, $C_{1-4}$-alkylamino or di-($C_{1-4}$-alkyl)-amino group,
an amino group substituted by the groups $R^{15}$ and $R^{16}$ wherein
$R^{15}$ denotes a hydrogen atom or a methyl or ethyl group and
$R^{16}$ denotes a $C_{1-4}$-alkyl group which is substituted by a cyano, carboxy, methoxycarbonyl, ethyloxycarbonyl, aminocarbonyl, methylaminocarbonyl, dimethylaminocarbonyl, ethylaminocarbonyl, diethylaminocarbonyl, pyrrolidin-1-ylcarbonyl or morpholin-4-ylcarbonyl group,
an amino group substituted by the groups $R^{15}$ and $R^{17}$ wherein
$R^{15}$ is as hereinbefore defined and
$R^{17}$ denotes a straight-chain $C_{2-4}$-alkyl group which is terminally substituted in each case by an amino, methylamino, dimethylamino, acetylamino, ethyloxycarbonylamino, phenylcarbonylamino, methylsulphonylamino, phenylsulphonylamino, hydroxy, methoxy, phenyloxy, methylsulphanyl or phenylsulphanyl group, a pyrrolidin-1-yl, piperidin-1-yl, morpholin-4-yl, piperazin-1-yl or 4-methyl-piperazin-1-yl group, a $C_{3-6}$-cycloalkylamino or $C_{3-6}$-cycloalkyl-$C_{1-3}$-alkylamino group, a phenylamino group, a phenyl-$C_{1-3}$-alkylamino group wherein the phenyl moiety is substituted by $R^{10}$ and $R^{11}$, where $R^{10}$ and $R^{11}$ are as hereinbefore defined, a naphthylmethylamino group, a heteroaryl-$C_{1-2}$-alkylamino group, where the term heteroaryl is as hereinbefore defined, or a methylsulphanyl, benzylsulphanyl or (2-phenylethyl)sulphanyl group, $R^3$ denotes a $C_{4-6}$-alkenyl group, a $C_{3-4}$-alkenyl group which is substituted by a fluorine, chlorine or bromine atom or a trifluoromethyl group, a 2-butyl-1-yl group or a methyl group substituted by the group $R_c$, where $R_c$ denotes a 1-cyclopenten-1-yl-or 1-cyclohexen-1-yl group, a phenyl group optionally substituted by a fluorine, chlorine, bromine or iodine atom, by a methyl, trifluoromethyl, cyano, methoxy, difluoromethoxy or trifluoromethoxy group, a phenyl group which is substituted by two fluorine atoms, a naphthyl group or a furanyl, thienyl, or pyridyl group, and $R^4$ denotes a piperidin-1-yl group which is substituted in the 3 position by an amino group, a hexahydroazepin-1-yl group which is substituted in the 3 position or 4 position by an amino group, a (2-aminocyclohexyl)amino group, a cyclohexyl group which is substituted in the 3 position by an amino group, or an N-(2-aminoethyl)-methylamino or an N-(2-aminoethyl)-ethylamino group, while unless otherwise stated, the above-mentioned alkyl, alkenyl and alkynyl groups may be straight-chain or branched.

4. The compound according to claim 3, wherein $R^1$ denotes a hydrogen atom, a methyl, benzyl or 2-phenylethyl group, a naphthylmethyl or methoxynaphthylmethyl group or a phenylcarbonylmethyl group, $R^2$ denotes a hydrogen atom, a methyl or 2-phenylethyl group, a phenylcarbonylmethyl group, a cyano group, an amino, methylamino, dimethylamino, isopropylamino, cyclohexylamino- or (cyclohexylmethyl)amino group, a benzylamino, fluorobenzylamino or (2-phenylethyl)amino group or a piperidin-1-yl group, $R^3$ denotes a benzyl or 3-methyl-but-2-en-1-yl group and $R^4$ denotes a (3-amino-piperidin-1-yl) group.

5. A compound chosen from:
(1) 8-(3-amino-piperidin-1-yl)-7-benzyl-2-benzylamino-1-methyl-1,7-dihydro-purin-6-one,
(2) 8-(3-amino-piperidin-1-yl)-7-benzyl-2-(4-fluoro-benzylamino)-1-methyl-1,7-dihydro-purin-6-one,
(3) 8-(3-amino-piperidin-1-yl)-7-benzyl-1-methyl-2-[(2-phenylethyl)amino]-1,7-dihydro-purin-6-one,
(4) 8-(3-amino-piperidin-1-yl)-7-benzyl-2-isopropylamino-1-methyl-1,7-dihydro-purin-6-one,
(5) 8-(3-amino-piperidin-1-yl)-7-benzyl-1-methyl-2-methylamino-1,7-dihydro-purin-6-one,
(6) 8-(3-amino-piperidin-1-yl)-7-benzyl-2-cyclohexylamino-1-methyl-1,7-dihydro-purin-6-one,
(7) 8-(3-amino-piperidin-1-yl)-7-benzyl-2-[(cyclohexylmethyl) amino]-1-methyl-1,7-dihydro-purin-6-one,
(8) 8-(3-amino-piperidin-1-yl)-7-benzyl-1-methyl-2-(piperidin-1-yl)-1,7-dihydro-purin-6-one,
(9) 8-(3-amino-piperidin-1-yl)-7-benzyl-2-dimethylamino-1-methyl-1,7-dihydro-purin-6-one,
(10) 2-amino-8-(3-amino-piperidin-1-yl)-7-benzyl-1-methyl-1,7-dihydro-purin-6-one,
(11) 8-(3-amino-piperidin-1-yl)-2-benzylamino-1-methyl-7-(3-methyl-but-2-en-1-yl)-1,7-dihydro-purin-6-one,
(12) 8-(3-amino-piperidin-1-yl)-7-benzyl-1-methyl-2-methyl-1,7-dihydro-purin-6-one,
(13) 8-(3-amino-piperidin-1-yl)-1-methyl-7-(3-methyl-but-2-en-1-yl)-2-(2-phenyl-ethyl)-1,7-dihydro-purin-6-one,
(14) 8-(3-amino-piperidin-1-yl)-7-benzyl-1-methyl-1,7-dihydro-purin-6-one,
(15) 8-(3-amino-piperidin-1-yl)-7-benzyl-1-(2-oxo-2-phenyl-ethyl)-1,7-dihydro-purin-6-one,
(16) 8-(3-amino-piperidin-1-yl)-2-methyl-7-(3-methyl-but-2-en-1-yl)-1-[(naphthalen-1-yl)methyl]-1,7-dihydro-purin-6-one,
(17) 8-(3-amino-piperidin-1-yl)-7-(3-methyl-but-2-en-1-yl)-1-[(naphthalen-1-yl)methyl]-1,7-dihydro-purin-6-one and
(18) 8-(3-amino-piperidin-1-yl)-7-(3-methyl-but-2-en-1-yl)-1-[(4-methoxy-naphthalen-1-yl)methyl]-1,7-dihydro-purin-6-one as well as the tautomers, enantiomers, diastereomers, the mixtures thereof and the salts thereof.

6. A physiologically acceptable salt of a compound according to claim 1 with inorganic or organic acids or bases.

7. A pharmaceutical composition comprising a pharmaceutically effective amount of a compound according to claim 1 optionally together with one or more pharmaceutically acceptable inert carriers and/or diluents.

8. A method of treating or preventing type II diabetes mellitus or obesity, comprising administering to a patient in need thereof a pharmaceutically effective amount of a compound according to claim 1.

9. A method of treating type II diabetes mellitus, or obesity, comprising administering to a patient in need thereof a pharmaceutically effective amount of a compound according to claim 1, wherein the administering is of 1 to 100 mg of the compound by intravenous route, or of 1 to 1000 mg by oral route, in each case 1 to 4 times a day.

10. A method of treating type II diabetes mellitus, or obesity, comprising administering to a patient in need thereof a pharmaceutically effective amount of a compound according to claim 1, wherein the administering is of 1 to 30 mg of the compound by intravenous route, or of 1 to 100 mg by oral route, in each case 1 to 4 times a day.

11. A method of treating type II diabetes mellitus, or obesity, comprising administering to a patient in need thereof a pharmaceutically effective amount of a compound according to claim 2.

12. A method of treating type II diabetes mellitus, or obesity, comprising administering to a patient in need thereof a pharmaceutically effective amount of a compound according to claim 3.

13. A method of treating type II diabetes mellitus, or obesity, comprising administering to a patient in need thereof a pharmaceutically effective amount of a compound according to claim 4.

14. A method of treating type II diabetes mellitus, or obesity, comprising administering to a patient in need thereof a pharmaceutically effective amount of a compound according to claim 5.

* * * * *